(12) United States Patent
Wicha et al.

(10) Patent No.: US 9,327,023 B2
(45) Date of Patent: May 3, 2016

(54) HER2 TARGETING AGENT TREATMENT IN NON-HER2-AMPLIFIED CANCERS HAVING HER2 EXPRESSING CANCER STEM CELLS

(71) Applicant: The Regents of the University of Michigan, Ann Arbor, MI (US)

(72) Inventors: Max S. Wicha, Ann Arbor, MI (US); Hasan Korkaya, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 425 days.

(21) Appl. No.: 13/660,333

(22) Filed: Oct. 25, 2012

(65) Prior Publication Data

US 2013/0142785 A1    Jun. 6, 2013

Related U.S. Application Data

(60) Provisional application No. 61/551,106, filed on Oct. 25, 2011.

(51) Int. Cl.
| | | |
|---|---|---|
| *A61K 39/395* | (2006.01) | |
| *C12Q 1/68* | (2006.01) | |
| *C07K 16/28* | (2006.01) | |
| *C07K 16/32* | (2006.01) | |
| *C12N 15/113* | (2010.01) | |
| *A61K 31/337* | (2006.01) | |
| *A61K 31/685* | (2006.01) | |
| *A61K 39/00* | (2006.01) | |

(52) U.S. Cl.
CPC .......... *A61K 39/39558* (2013.01); *A61K 31/337* (2013.01); *A61K 31/685* (2013.01); *A61K 39/3955* (2013.01); *C07K 16/2866* (2013.01); *C07K 16/32* (2013.01); *C12N 15/113* (2013.01); *C12Q 1/6886* (2013.01); *A61K 2039/505* (2013.01); *A61K 2039/507* (2013.01); *C07K 2317/76* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,935,341 A | 6/1990 | Bargmann et al. |
| 4,968,603 A | 11/1990 | Slamon et al. |
| 4,981,785 A | 1/1991 | Nayak |
| 5,210,075 A | 5/1993 | Scholz et al. |
| 5,288,477 A | 2/1994 | Bacus |
| 5,358,691 A | 10/1994 | Clark et al. |
| 5,401,638 A | 3/1995 | Carney et al. |
| 5,514,554 A | 5/1996 | Bacus |
| 5,571,894 A | 11/1996 | Wels et al. |
| 5,587,458 A | 12/1996 | King et al. |
| 5,599,677 A | 2/1997 | Dowell et al. |
| 5,604,107 A | 2/1997 | Carney et al. |
| 5,648,237 A | 7/1997 | Carter |
| 5,672,480 A | 9/1997 | Dowell et al. |
| 5,677,171 A | 10/1997 | Hudziak et al. |
| 5,705,157 A | 1/1998 | Greene |
| 5,720,937 A | 2/1998 | Hudziak et al. |
| 5,720,954 A | 2/1998 | Hudziak et al. |
| 5,725,856 A | 3/1998 | Hudziak et al. |
| 5,747,261 A | 5/1998 | King et al. |
| 5,770,195 A | 6/1998 | Hudziak et al. |
| 5,772,997 A | 6/1998 | Hudziak et al. |
| 5,783,186 A | 7/1998 | Arakawa et al. |
| 5,783,404 A | 7/1998 | Koski |
| 5,804,396 A | 9/1998 | Plowman |
| 5,821,337 A | 10/1998 | Carter et al. |
| 5,824,311 A | 10/1998 | Greene et al. |
| 5,837,243 A | 11/1998 | Deo et al. |
| 5,846,749 A | 12/1998 | Slamon et al. |
| 5,856,089 A | 1/1999 | Wang et al. |
| 5,877,305 A | 3/1999 | Huston et al. |
| 5,885,530 A | 3/1999 | Babson et al. |
| 5,910,486 A | 6/1999 | Curiel et al. |
| 5,922,845 A | 7/1999 | Deo et al. |
| 5,925,519 A | 7/1999 | Jensen et al. |
| 5,939,531 A | 8/1999 | Wels et al. |
| 5,977,322 A | 11/1999 | Marks et al. |
| 5,985,553 A | 11/1999 | King et al. |
| 5,994,071 A | 11/1999 | Ross et al. |
| 6,015,567 A | 1/2000 | Hudziak et al. |

(Continued)

FOREIGN PATENT DOCUMENTS

| | | |
|---|---|---|
| EP | 0656367 | 6/1995 |
| EP | 0412116 | 11/1995 |

(Continued)

OTHER PUBLICATIONS

Paik et al, (Journal of the National Cancer institute, 2002, vol. 94, pp. 852-854).*

(Continued)

*Primary Examiner* — Karen Canella

(74) *Attorney, Agent, or Firm* — Casimir Jones SC; David W. Staple

(57) ABSTRACT

The present invention relates to compositions, methods, and kits for treating cancers with HER2 targeting agents and preventing resistance thereto. In particular embodiments, non-HER2-amplified cancers are treated with HER2 targeting agents, wherein the cancer stem cells in the cancer express HER2 and/or HER2 indicator marker. The present invention also relates to compositions, methods, and kits for detecting expression of HER2 and/or a HER2 indicator marker in non-HER2-amplified cancer samples from a subject, and identifying the subject as responsive to treatment with a HER2 targeting agent and/or treating the subject with a HER2 targeting agent.

17 Claims, 33 Drawing Sheets

(56) References Cited

U.S. PATENT DOCUMENTS

| | | |
|---|---|---|
| 6,028,059 A | 2/2000 | Curiel et al. |
| 6,054,297 A | 4/2000 | Carter et al. |
| 6,123,939 A | 9/2000 | Shawver et al. |
| 6,127,526 A | 10/2000 | Blank |
| 6,159,750 A | 12/2000 | Edmonds |
| 6,165,464 A | 12/2000 | Hudziak et al. |
| 6,172,042 B1 | 1/2001 | Chebath et al. |
| 6,214,388 B1 | 4/2001 | Benz et al. |
| 6,267,958 B1 | 7/2001 | Andya et al. |
| 6,270,765 B1 | 8/2001 | Deo et al. |
| 6,333,169 B1 | 12/2001 | Hudziak et al. |
| 6,333,348 B1 | 12/2001 | Vogel et al. |
| 6,333,398 B1 | 12/2001 | Blank |
| 6,339,142 B1 | 1/2002 | Basey et al. |
| 6,358,682 B1 | 3/2002 | Jaffee et al. |
| 6,387,371 B1 | 5/2002 | Hudziak et al. |
| 6,395,272 B1 | 5/2002 | Deo et al. |
| 6,399,063 B1 | 6/2002 | Hudziak et al. |
| 6,403,630 B1 | 6/2002 | Dannenberg et al. |
| 6,407,213 B1 | 6/2002 | Carter et al. |
| 6,417,335 B1 | 7/2002 | Basey et al. |
| 6,458,356 B1 | 10/2002 | Arakawa et al. |
| 6,489,447 B1 | 12/2002 | Basey et al. |
| 6,512,097 B1 | 1/2003 | Marks et al. |
| 6,573,043 B1 | 6/2003 | Cohen et al. |
| 6,582,919 B2 | 6/2003 | Danenberg et al. |
| 6,599,875 B1 | 7/2003 | Serlupi-Crescenzi et al. |
| 6,602,670 B2 | 8/2003 | Danenberg |
| 6,627,196 B1 | 9/2003 | Baughman et al. |
| 6,632,979 B2 | 10/2003 | Erickson et al. |
| 6,685,940 B2 | 2/2004 | Andya et al. |
| 6,719,971 B1 | 4/2004 | Carter et al. |
| 6,767,541 B2 | 7/2004 | Slamon et al. |
| 6,797,814 B2 | 9/2004 | Blank |
| 6,800,738 B1 | 10/2004 | Carter et al. |
| 6,821,515 B1 | 11/2004 | Cleland et al. |
| 6,838,433 B2 | 1/2005 | Serlupi-Crescenzi et al. |
| 6,841,533 B1 | 1/2005 | Hornik et al. |
| 6,984,522 B2 | 1/2006 | Clarke et al. |
| 7,115,360 B2 | 10/2006 | Clarke et al. |
| 7,723,112 B2 | 5/2010 | Clarke et al. |
| 7,939,263 B2 | 5/2011 | Clarke et al. |
| 2002/0031515 A1 | 3/2002 | Caligiuri et al. |
| 2002/0051785 A1 | 5/2002 | Slamon et al. |
| 2002/0064785 A1 | 5/2002 | Mass |
| 2002/0076408 A1 | 6/2002 | Buchsbaum |
| 2002/0076695 A1 | 6/2002 | Ross |
| 2002/0090662 A1 | 7/2002 | Ralph |
| 2002/0141993 A1 | 10/2002 | Ashkenazi et al. |
| 2002/0142328 A1 | 10/2002 | Danenberg |
| 2002/0155527 A1 | 10/2002 | Stuart et al. |
| 2002/0192211 A1 | 12/2002 | Hudziak et al. |
| 2002/0192652 A1 | 12/2002 | Danenberg |
| 2003/0022918 A1 | 1/2003 | Horak et al. |
| 2003/0059790 A1 | 3/2003 | Jaffee et al. |
| 2003/0068318 A1 | 4/2003 | O'Brien et al. |
| 2003/0086924 A1 | 5/2003 | Sliwkowski |
| 2003/0103973 A1 | 6/2003 | Rockwell et al. |
| 2003/0108545 A1 | 6/2003 | Rockwell et al. |
| 2003/0134344 A1 | 7/2003 | Mass |
| 2003/0144252 A1 | 7/2003 | Furr |
| 2003/0147884 A1 | 8/2003 | Paton |
| 2003/0152572 A1 | 8/2003 | Homma et al. |
| 2003/0152987 A1 | 8/2003 | Cohen et al. |
| 2003/0157097 A1 | 8/2003 | Noguchi et al. |
| 2003/0165840 A1 | 9/2003 | Danenberg |
| 2003/0170234 A1 | 9/2003 | Hellmann |
| 2003/0175845 A1 | 9/2003 | Kalbag et al. |
| 2003/0202973 A1 | 10/2003 | Pieczenik et al. |
| 2003/0211530 A1 | 11/2003 | Danenberg |
| 2003/0228663 A1 | 12/2003 | Lowman et al. |
| 2004/0013667 A1 | 1/2004 | Kelsey et al. |
| 2004/0082047 A1 | 4/2004 | Emery et al. |
| 2004/0106161 A1 | 6/2004 | Bossenmaier et al. |
| 2004/0138160 A1 | 7/2004 | Naito et al. |
| 2004/0236078 A1 | 11/2004 | Carter et al. |
| 2004/0258685 A1 | 12/2004 | Brunetta et al. |
| 2005/0002928 A1 | 1/2005 | Hellmann |
| 2005/0090453 A1 | 4/2005 | Carter et al. |
| 2006/0019256 A1 | 1/2006 | Clarke et al. |
| 2007/0010529 A1 | 1/2007 | Takahashi et al. |
| 2007/0099209 A1 | 5/2007 | Clarke et al. |
| 2008/0260734 A1 | 10/2008 | Clarke et al. |
| 2008/0261244 A1 | 10/2008 | Wicha et al. |
| 2009/0142359 A1 | 6/2009 | Arakawa et al. |
| 2010/0240041 A1 | 9/2010 | Matsunaga et al. |
| 2011/0191868 A1 | 8/2011 | Gupta et al. |

FOREIGN PATENT DOCUMENTS

| | | |
|---|---|---|
| EP | 0494135 | 4/1996 |
| EP | 0502812 | 8/1996 |
| EP | 0554441 | 1/1997 |
| EP | 0711565 | 8/1998 |
| EP | 0616812 | 11/1999 |
| EP | 1006194 | 6/2000 |
| EP | 0444181 | 10/2001 |
| EP | 1357132 | 10/2003 |
| WO | WO 87/07646 | 12/1987 |
| WO | WO 89/10412 | 11/1989 |
| WO | WO 91/02062 | 2/1991 |
| WO | WO 91/05264 | 4/1991 |
| WO | WO 93/03741 | 3/1993 |
| WO | WO 93/12220 | 6/1993 |
| WO | WO 93/16185 | 8/1993 |
| WO | WO 93/21232 | 10/1993 |
| WO | WO 93/21319 | 10/1993 |
| WO | WO 94/00136 | 1/1994 |
| WO | WO 94/22478 | 10/1994 |
| WO | WO 96/07321 | 3/1996 |
| WO | WO 96/16673 | 6/1996 |
| WO | WO 96/40789 | 12/1996 |
| WO | WO 97/00271 | 1/1997 |
| WO | WO 97/20858 | 6/1997 |
| WO | WO 97/38731 | 10/1997 |
| WO | WO 98/02463 | 1/1998 |
| WO | WO 98/17797 | 4/1998 |
| WO | WO 98/18489 | 5/1998 |
| WO | WO 98/33914 | 8/1998 |
| WO | WO 98/45479 | 10/1998 |
| WO | WO 99/31140 | 6/1999 |
| WO | WO 99/48527 | 9/1999 |
| WO | WO 99/55367 | 11/1999 |
| WO | WO 00/61145 | 10/2000 |
| WO | WO 00/61185 | 10/2000 |
| WO | WO 00/69460 | 11/2000 |
| WO | WO 00/78347 | 12/2000 |
| WO | WO 01/00238 | 1/2001 |
| WO | WO 01/00244 | 1/2001 |
| WO | WO 01/00245 | 1/2001 |
| WO | WO 01/05425 | 1/2001 |
| WO | WO 01/09187 | 2/2001 |
| WO | WO 01/15730 | 3/2001 |
| WO | WO 01/20033 | 3/2001 |
| WO | WO 01/21192 | 3/2001 |
| WO | WO 01/32155 | 5/2001 |
| WO | WO 01/53354 | 7/2001 |
| WO | WO 01/56604 | 8/2001 |
| WO | WO 01/64246 | 9/2001 |
| WO | WO 01/76586 | 10/2001 |
| WO | WO 01/76630 | 10/2001 |
| WO | WO 01/87334 | 11/2001 |
| WO | WO 01/87336 | 11/2001 |
| WO | WO 01/89566 | 11/2001 |
| WO | WO 02/05791 | 1/2002 |
| WO | WO 02/09754 | 2/2002 |
| WO | WO 02/11677 | 2/2002 |
| WO | WO 02/44413 | 6/2002 |
| WO | WO 02/45653 | 6/2002 |
| WO | WO 02/055106 | 7/2002 |
| WO | WO 02/070008 | 9/2002 |
| WO | WO 02/087619 | 11/2002 |
| WO | WO 02/089842 | 11/2002 |
| WO | WO 03/006509 | 1/2003 |

(56) References Cited

FOREIGN PATENT DOCUMENTS

| WO | WO 03/012072 | 2/2003 |
|---|---|---|
| WO | WO 03/028638 | 4/2003 |
| WO | WO 03/041736 | 5/2003 |
| WO | WO 03/086467 | 10/2003 |
| WO | WO 03/087131 | 10/2003 |
| WO | WO 2004/008099 | 1/2004 |
| WO | WO 2004/024866 | 3/2004 |
| WO | WO 2004/048525 | 6/2004 |
| WO | WO 2009/149306 | 12/2009 |
| WO | WO2010/006027 | * 1/2010 |

OTHER PUBLICATIONS

Riley et al (PLOS One, 2012, vol. 7, e46613).*
Shinriki et al (Clinical Cancer Research, 2009, vol. 15, pp. 5426-5434).*
Dent et al (Cancer Treatment Reviews, 2006, vol. 32, pp. 144-148).*
Lu et al (Clinical Cancer Research, 2007, vol. 13, pp. 5883-5888).*
Lal et al., "HER-2 testing in breast cancer using immunohistochemical analysis and fluorescence in situ hybridization: a single-institution experience of 2,279 cases and comparison of dual-color and single-color scoring," Am J Clin Pathol. 2004, 121(5):631-636.
Lan et al., "Mechanisms of trastuzumab resistance and their clinical implications," Ann NY Acad Sci, 2005, 1059: 70-75.
Lee et al., "Requirement for neuregulin receptor erbB2 in neural and cardiac development," Nature, 1995, 378: 394-398.
Lewis et al., "Differential responses of human tumor cell lines to anti-p185HER2 monoclonal antibodies," Cancer Immunol Immunother, 1993, 37: 255-263.
Lewis et al., "Growth regulation of human breast and ovarian tumor cells by heregulin: Evidence for the requirement of ErbB2 as a critical component in mediating heregulin responsiveness," Cancer Res, 1996, 56: 1457-1465.
Li et al., "Intrinsic resistance of tumorigenic breast cancer cells to chemotherapy," J Natl Cancer Inst, 2008, 100: 672-679.
Lipton et al., "Quantitative HER2 protein levels predict outcome in fluorescence in situ hybridization-positive patients with metastatic breast cancer treated with trastuzumab," Cancer, 2010, 116: 5168-5178.
Magnifico et al., "Tumor-initiating cells of HER2-positive carcinoma cell lines express the highest oncoprotein levels and are sensitive to trastuzumab," Clin Cancer Res, 2009, 15: 2010-2021.
Maier et al., "Requirements for the internalization of a murine monoclonal antibody directed against the HER-2/neu gene product c-erbB-2," Cancer Res, 1991, 51: 5361-5369.
Mani et al., "The epithelial-mesenchymal transition generates cells with properties of stem cells," Cell, 2008, 133: 704-715.
Mass et al., "Evaluation of clinical outcomes according to HER2 detection by fluorescence in situ hybridization in women with metastatic breast cancer treated with trastuzumab," Clin Breast Cancer, 2005, 6: 240-246.
McKenzie et al., "Generation and characterization of monoclonal antibodies specific for the human neu oncogene product, p185," Oncogene, 1989, 4: 543-548.
Morrison et al., "Targeting the mechanisms of resistance to chemotherapy and radiotherapy with the cancer stem cell hypothesis," J Oncol, 2011, 2011:941876.
Mueller et al., "Hyaluronan inhibits postchemotherapy tumor regrowth in a colon carcinoma xenograft model," Mol Cancer Ther, 2010, 9: 3024-3032.
Nagata et al., "PTEN activation contributes to tumor inhibition by trastuzumab, and loss of PTEN predicts trastuzumab resistance in patients," Cancer Cell, 2004, 6:117-127.
National Cancer Institute, "Cancer Stem Cell Biomarkers as a Predictor of Response to Trastuzumab in Samples from Patients with Breast Cancer Previously Treated in the NSABP-B-31 Trial," as accessed from ClinicalTrials.gov on Oct. 19, 2011.
Paik et al., "HER2 status and benefit from adjuvant trastuzumab in breast cancer," N Engl J Med, 2008, 358: 1409-1411.

Paul et al., "Effective expression of small interfering RNA in human cells," Nat Biotechnol, 2002, 20: 505-508.
Pegram et al., "Antibody dependent cell-mediated cytotoxicity in breast cancer patients in Phase III clinical trials of a humanized anti-HER2 antibody," Proc Am Assoc Cancer, 1997, 38: 602, Abstract 4044.
Perez et al., "HER2 and chromosome 17 effect on patient outcome in the N9831 adjuvant trastuzumab trial," J Clin Oncol, 2010, 28: 4307-4315.
Piccart-Gebhart et al., "Trastuzumab after adjuvant chemotherapy in HER2-positive breast cancer," N Engl J Med, 2005, 353: 1659-1672.
Pietras et al., "Antibody to HER-2/neu receptor blocks DNA repair after cisplatin in human breast and ovarian cancer cells," Oncogene, 1994, 1829-1838.
Press et al., "Her-2/neu expression in node-negative breast cancer: direct tissue quantitation by computerized image analysis and association of overexpression with increased risk of recurrent disease," Cancer Res, 1993, 53: 4960-4970.
Riley et al., "Breast cancer stem cell extinction models: Implications for HER2 targeted therapy," Am Assoc Cancer Res Annual Meeting, 2010, Abstract 104.
Roesler et al., "HER2 as a stem -cell target," Lancet Oncol, 2010, 11(3): 225-226, abstract.
Romond et al., "Trastuzumab plus adjuvant chemotherapy for operable HER2-positive breast cancer," N Engl J Med, 2005, 353:1673-1684.
Salgado et al., "Circulating interleukin-6 predicts survival in patients with metastatic breast cancer," Int J Cancer, 2003, 103: 642-646.
Sarup et al., "Characterization of an anti-p185HER2 monoclonal antibody that stimulates receptor function and inhibits tumor cell growth," Growth Regulation, 1991, 1:72-82.
Schaefer et al., "Gamma-heregulin: a novel heregulin isoform that is an autocrine growth factor for the human breast cancer cell line, MDA-MB-175," Oncogene, 1997, 15: 1385-1394.
Schoning et al., "Chemical etiology of nucleic acid structure: the alpha-threofuranosyl-(3'→2') oligonucleotide system," Science, 2000, 290: 1347-1351.
Scott et al., "p185HER2 signal transduction in breast cancer cells," J Biol Chem, 1991, 266: 14300-14305.
Shafee et al., "Cancer stem cells contribute to cisplatin resistance in Brca1/p53-mediated mouse mammary tumors," Cancer Res, 2008, 68: 3243-3250.
Shawver et al., "Ligand-like effects induced by anti-c-erbB-2 antibodies do not correlate with and are not required for growth inhibition of human carcinoma cells," Cancer Res, 1994, 1367-1373.
Shepard et al., "Monoclonal antibody therapy of human cancer: taking the HER2 protooncogene to the clinic," J Clin Immunol, 1991, 11(3): 117-127.
Silverman et al., "Multivalent avimer proteins evolved by exon shuffling of a family of human receptor domains," Nat Biotechnol, 2005, 23: 1556-1561.
Slamon et al., "Human breast cancer: correlation of relapse and survival with amplification of the HER-2/neu oncogene," Science, 1987, 235: 177-182.
Slamon et al., "Use of chemotherapy plus a monoclonal antibody against HER2 for metastatic breast cancer that overexpresses HER2," N Engl J Med, 2001, 344: 783-792.
Sliwkowski et al., "Coexpression of erbB2 and erbB3 proteins reconstitutes a high affinity receptor for heregulin," J Biol Chem, 1994, 269(20): 14661-14665.
Smith et al., "2-year follow-up of trastuzumab after adjuvant chemotherapy in HER2-positive breast cancer: a randomised controlled trial," Lancet, 2007, 369: 29-36.
Spielmann et al., "Trastuzumab for patients with axillary-node-positive breast cancer: results of the FNCLCC-PACS 04 trial," J Clin Oncol, 2009, 27: 6129-6134.
Stancovsk et al., "Mechanistic aspects of the opposing effects of monoclonal antibodies to the ERBB2 receptor on tumor growth," PNAS USA, 1991, 88: 8691-8695.
Susman, "AACR: Are Cancer Stem Cells Vulnerable to Trastuzumab?," MedPageToday, 2010, as accessed on Oct. 19, 2011 from MedPageToday.com.

(56) References Cited

OTHER PUBLICATIONS

Tagliabue et al., "Selection of monoclonal antibodies which induce internalization and phosphorylation of p185HER2 and growth inhibition of cells with HER2/NEU gene amplification," Int J Cancer, 1991, 47: 933-937.
Tai et al., "Antibody-Based Therapies in Multiple Myeloma," Bone Marrow Res, 2011: 924058.Published online 2011.
Takeda et al., "Synthetic retinoid Am80 reduces scavenger receptor expression and atherosclerosis in mice by inhibiting IL-6," Arterioscler Thromb Vasc Biol, 2006, 26: 1177-1183.
Tan-Chiu et al., "Assessment of cardiac dysfunction in a randomized trial comparing doxorubicin and cyclophosphamide followed by paclitaxel, with or without trastuzumab as adjuvant therapy in node-positive, human epidermal growth factor receptor 2-overexpressing breast cancer: NSABP B-31," J Clin Oncol, 2005, 7811-7819.
Vitetta et al., "Monoclonal antibodies as agonists: an expanded role for their use in cancer therapy," Cancer Res, 1994, 54: 5301-5309.
Vogel et al., "Efficacy and safety of trastuzumab as a single agent in first-line treatment of HER2-overexpressing metastatic breast cancer," J Clin Oncol, 2002, 20: 719-726.
Vogel et al., "First-line Herceptin monotherapy in metastatic breast cancer," Oncology, 2001, 61(Suppl 2): 37-42.
Wahlestedt et al., "Potent and nontoxic antisense oligonucleotides containing locked nucleic acids," Proc Natl Acad Sci USA, 2000, 97: 5633-5638.
Weissenbacher et al., "IL-6 is required for glioma development in a mouse model," Oncogene, 2004, 23: 3308-3316.
Wicha et al., "Cancer stem cells: an old idea—a paradigm shift," Cancer Res, 2006, 66: 1883-1890, discussion 1895-1886.
Wicha, "Targeting breast cancer stem cells," Breast, 2009, 18 Suppl 3:S56-8.
Wolff et al., "American Society of Clinical Oncology/College of American Pathologists guideline recommendations for human epidermal growth factor receptor 2 testing in breast cancer," J Clin Oncol, 2007, 25: 118-145.
Xu et al., "Antibody-induced growth inhibition is mediated through immunochemically and functionally distinct epitopes on the extracellular domain of the c-erbB-2 (HER-2/neu) gene product p185," Int J Cancer, 1993, 53: 401-408.
Yao et al., "TGF-beta IL-6 axis mediates selective and adaptive mechanisms of resistance to molecular targeted therapy in lung cancer," Proc Natl Acad Sci USA, 2010, 107: 15535-15540.
Yu et al., "A clinically relevant orthotopic xenograft model of ependymoma that maintains the genomic signature of the primary tumor and preserves cancer stem cells in vivo," Neuro Oncol, 2010, 12-580-594.
Zhang et al., "A simple glycol nucleic acid," J Am Chem Soc, 2005, 127: 4174-4175.
International Search Report and Written Opinion for Int'l Application No. PCT/US2012/061857, mailed Feb. 5, 2013.
Al-Hajj et al., "Prospective identification of tumorigenic breast cancer cells," Proc Natl Acad Sci USA, 2003, 100, 3983-3988.
Arteaga et al., "p185c-erbB-2 signal enhances cisplatin-induced cytotoxicity in human breast carcinoma cells: association between an oncogenic receptor tyrosine kinase and drug-induced DNA repair," Cancer Res, 1994, 54: 3758-3765.
Bachelot et al., "Prognostic value of serum levels of interleukin 6 and of serum and plasma levels of vascular endothelial growth factor in hormone-refractory metastatic breast cancer patients," Br J Cancer, 2003, 88: 1721-1726.
Bacus et al., "Differentiation of cultured human breast cancer cells (AU-565 and MCF-7) associated with loss of cell surface HER-2/neu antigen," Mol Carcinogen, 1990, 3: 350-362.
Bacus et al., "Tumor-inhibitory monoclonal antibodies to the HER-2/Neu receptor induce differentiation of human breast cancer cells," Cancer Res, 1992, 52: 2580-2589.
Baselga et al., "Recombinant humanized anti-HER2 antibody (Herceptin) enhances the antitumor activity of paclitaxel and doxorubicin against HER2/neu overexpressing human breast cancer xenografts," Cancer Res, 1998, 2825-2831.
Berns et al., "A functional genetic approach identifies the PI3K pathway as a major determinant of trastuzumab resistance in breast cancer," Cancer Cell, 2007, 12: 395-402.
Braasch et al., "Novel antisense and peptide nucleic acid strategies for controlling gene expression," Biochemistry, 2002, 41: 4503-4510.
Breast Cancer Research Foundation Online Profile of Max S. Wicha, MD, as accessed on Oct. 19, 2011.
Bromberg et al., "Inflammation and cancer: IL-6 and STAT3 complete the link," Cancer Cell, 2009, 15: 79-80.
Charafe- Jauffret et al., "Breast cancer cell lines contain functional cancer stem cells with metastatic capacity and a distinct molecular signature," Cancer Res, 2009, 69: 1302-1313.
Cicalese et al., "The tumor suppressor p53 regulates polarity of self-renewing divisions in mammary stem cells," Cell, 2009, 138: 1083-1095.
Clarke et al., "Cancer stem cells—perspectives on current status and future directions: AACR Workshop on cancer stem cells," Cancer Res, 2006, 66: 9339-9344.
D'Anello et al., "Epigenetic control of the basal-like gene expression profile via Interleukin-6 in breast cancer cells," Mol Cancer, 2010, 9: 300.
D'Souza et al., "Overexpression of ERBB2 in human mammary epithelial cells signals inhibition of transcription of the *E-cadherin* gene," Proc Natl Acad Sci USA, 1994, 91: 7202-7206,.
Diehn et al., "Association of reactive oxygen species levels and radioresistance in cancer stem cells," Nature, 2009, 458: 780-783.
Dontu et al., "In vitro propagation and transcriptional profiling of human mammary stem/progenitor cells," Genes Dev, 2003, 17: 1253-1270.
Fabi et al., "HER2 protein and gene variation between primary and metastatic breast cancer: significance and impact on patient care," Clin Cancer Res, 2011, 17: 2055-2064.
Fendly et al., "Characterization of murine monoclonal antibodies reactive to either the human epidermal growth factor receptor or HER2/neu gene product," Cancer Res, 1990, 50: 1550-1558.
Ginestier et al., "ALDH1 is a marker of normal and malignant human mammary stem cells and a predictor of poor clinical outcome," Cell Stem Cell, 2007, 1:555-567.
Ginestier et al., "CXCR1 blockade selectively targets human breast cancer stem cells in vitro and in xenografts," J Clin Invest, 2010, 120: 485-497.
Hambardzumyan et al., "Radiation resistance and stem-like cells in brain tumors," Cancer Cell, 2006, 10: 454-456.
Hancock et al., "A monoclonal antibody against the c-erbB-2 protein enhances the cytotoxicity of cis-diamminedichloroplatinum against human breast and ovarian tumor cell lines," Cancer Res, 1991, 51: 4575-4580.
Hannon et al., "Unlocking the potential of the human genome with RNA interference," Nature, 2004, 431: 371-378.
Hanvey et al., "Antisense and antigene properties of peptide nucleic acids," Science, 992, 258: 1481-1485.
Hartman et al., "HER2 overexpression elicits a proinflammatory IL-6 autocrine signaling loop that is critical for tumorigenesis," Cancer Res, 2011, 71: 4380-4391.
Harwerth et al., "Monoclonal antibodies against the extracellular domain of the erbB-2 receptor function as partial ligand agonists," J Biol Chem, 1992, 267: 15160-15167.
He et al., "High tumor levels of IL6 and IL8 abrogate preclinical efficacy of the y-secretase inhibitor, RO4929097," Mol Oncol, 2011, 5: 292-301.
Heasman et al., "Morpholino oligos: making sense of antisense?," Dev Biol, 2002, 243:209-214.
Hosokawa et al., "High-density microcavity array for cell detection: single-cell analysis of hematopoietic stem cells in peripheral blood mononuclear cells," Anal Chem, 2009, 81(13): 5308-5313.
Hudziak et al., "p185HER2 monoclonal antibody has antiproliferative effects in vitro and sensitizes human breast tumor cells to tumor necrosis factor," Mol Cell Biol, 1989, 9(3): 1165-1172.
Iliopoulos et al., "An epigenetic switch involving NF-kappaB, Lin28, Let-7 MicroRNA, and IL6 links inflammation to cell transformation," Cell, 2009, 139: 693-706.

(56) References Cited

OTHER PUBLICATIONS

Iliopoulos et al., "Inducible formation of breast cancer stem cells and their dynamic equilibrium with non-stem cancer cells via IL6 secretion," Proc Natl Acad Sci USA, 2011, 108: 1397-1402.

Iliopoulos et al., "STAT3 activation of miR-21 and miR-181b-1 via PTEN and CYLD are part of the epigenetic switch linking inflammation to cancer," Mol Cell, 2010, 39: 493-506.

Joensuu et al., "Adjuvant docetaxel or vinorelbine with or without trastuzumab for breast cancer," N Engl J Med, 2006, 354: 809-820.

Kasprzyk et al., "Therapy of an animal model of human gastric cancer using a combination of anti-erbB-2 monoclonal antibodies," Cancer Res, 1992, 52: 2771-2776.

Kennecke et al., "Metastatic behavior of breast cancer subtypes," J Clin Oncol, 2010, 28: 3271-3277.

Klapper et al., "A subclass of tumor-inhibitory monoclonal antibodies to ErbB-2/HER2 blocks crosstalk with growth factor receptors," Oncogene, 1997, 14: 2099-2109.

Korkaya et al., "Herceptin Targets Breast Cancer Stem Cells," Science Daily News, 2008, as accessed on Oct. 19, 2011 from ScienceDaily.com.

Korkaya et al., "HER2 regulates the mammary stem/progenitor cell population driving tumorigenesis and invasion," Oncogene, 2008, 27: 6120-6130.

Korkaya et al., "HER-2, notch, and breast cancer stem cells: targeting an axis of evil," Clin Cancer Res, 2009, 15: 1845-1847.

Korkaya et al., "Regulation of cancer stem cells by cytokine networks: attacking cancer's inflammatory roots," Clin Cancer Res, 2011, 17: 6125-6129.

Korkaya et al., "Regulation of mammary stem/progenitor cells by PTEN/Akt/beta-catenin signaling," PLoS Biol, 2009, 7: e1000121.

Kotts et al., "Differential Growth Inhibition of Human Carcinoma Cells exposed to Monoclonal Antibodies Directed against the Extracellular Domain of the HER2/ERBB2 Protooncogene.," In Vitro Cell & Dev Biol, Annual Meeting Abstracts, 1990, 26(3): 59A, Abstract 176.

Kumar et al., "Regulation of phosphorylation of the c-erbB-2/HER2 gene product by a monoclonal antibody and serum growth factor(s) in human mammary carcinoma cells," Mol Cell Biol, 1991, 11: 979-986.

* cited by examiner

HER2 TARGETING AGENT TREATMENT IN NON-HER2-AMPLIFIED CANCERS HAVING HER2 EXPRESSING CANCER STEM CELLS

This application claims priority to provisional patent application Ser. No. 61/551,106, filed Oct. 25, 2011, which is herein incorporated by reference in its entirety.

GOVERNMENT SUPPORT

This invention was made with government support under CA129765 awarded by the National Institutes of Health. The government has certain rights in the invention.

FIELD OF THE INVENTION

The present invention relates to compositions, methods, and kits for treating cancers with HER2 targeting agents and preventing resistance thereto. In particular embodiments, non-HER2-amplified cancers are treated with HER2 targeting agents, wherein the cancer stem cells in the cancer express HER2 and/or HER2 indicator marker. The present invention also relates to compositions, methods, and kits for detecting expression of HER2 and/or a HER2 indicator marker in non-HER2-amplified cancer samples from a subject, and identifying the subject as responsive to treatment with a HER2 targeting agent and/or treating the subject with a HER2 targeting agent.

BACKGROUND OF THE INVENTION

Approximately 20% of breast cancers display amplification of the HER2 gene, a genotype historically associated with an aggressive course and poor outcome (Slamon, D. J., et al. Science 235, 177-182 (1987); herein incorporated by reference in its entirety). The development of agents such as trastuzumab and lapatinib that are capable of targeting HER2 represents one of the greatest achievements in clinical oncology providing a prime example for the effectiveness of molecularly targeted therapeutics (Vogel, C. L., et al. J Clin Oncol 20, 719-726 (2002); herein incorporated by reference in its entirety). In women with advanced metastatic breast cancer, the addition of trastuzumab to cytotoxic chemotherapy increases the response rate, time to tumor progression and survival (Vogel, C. L., et al. J Clin Oncol 20, 719-726 (2002); Slamon, D. J., et al. N Engl J Med 344, 783-792. (2001); Vogel, C. L., et al. Oncology 61 Suppl 2, 37-42 (2001); herein incorporated by reference in their entireties). The beneficial effects of trastuzumab in this setting appear to be limited to breast tumors with HER2 amplification (Mass, R. D., et al. Clin Breast Cancer 6, 240-246 (2005); Wolff, A. C., et al. J Clin Oncol 25, 118-145 (2007); herein incorporated by reference in their entireties). These clinical findings supported earlier preclinical data utilizing cell lines and xenografts models which demonstrated that the beneficial effects of HER2 blockade were limited to HER2 amplified breast cancers (Mueller, B. M., et al. Mol Cancer Ther 9, 3024-3032 (2010); herein incorporated by reference in its entirety). The results of these studies prompted the development of standardized laboratory tests to assess HER2 expression. Although treatment decisions are usually based on the HER2 status obtained on the primary tumor, a number of studies have demonstrated discordance between HER2 expression in the primary tumor and at metastatic sites. This discordance is significantly greater when HER2 is analyzed by immunohistochemistry at the protein level then when analyzed for HER2 gene HER2 amplification by FISH (Fabi, A., et al. Clin Cancer Res 17, 2055-2064 (2011); Lipton, A., et al. Cancer 116, 5168-5178 (2010); herein incorporated by reference in their entireties).

Based on the demonstrated clinical efficacy of HER2 blockade in the advanced setting, a number of large randomized clinical trials were initiated to determine whether administration of HER2 blocking agents in the adjuvant setting would prevent recurrence. Reflecting the observation in advanced disease trials that the benefit of HER2 blockade was limited to women whose tumors displayed HER2 amplification, inclusion of patients into adjuvant trials was limited to this patient population. These adjuvant trials demonstrated a remarkable 50% reduction in recurrence rate with the addition of trastuzumab to chemotherapy compared to chemotherapy alone (Joensuu, H., et al. N Engl J Med 354, 809-820 (2006); Piccart-Gebhart, M. J., et al. N Engl J Med 353, 1659-1672 (2005); Romond, E. H., et al. N Engl J Med 353, 1673-1684 (2005); Smith, I., et al. Lancet 369, 29-36 (2007); Spielmann, M., et al. J Clin Oncol 27, 6129-6134 (2009); herein incorporated by reference in their entireties). Long term followings of these patients have confirmed the long term benefits of adjuvant trastuzumab (JCO, 2011). Since HER2 amplified breast cancers have an aggressive natural course, most recurrences occur within 5-7 years suggesting that the flat survival curves after this period may reflect dramatic increase in the cure rates.

SUMMARY OF THE INVENTION

The present invention provides compositions, methods, and kits for treating non-HER2-amplified cancer with HER2 targeting agents (e.g., Trastuzumab), where the cancer stem cells in the cancer express HER2 and/or HER2 indicator marker. In certain embodiments, the present invention further provides administering IL6R targeting agents (e.g., anti-IL6R antibody (e.g., Tocilizumab), alone or in combination with HER2 targeting agents. The present invention also provides compositions, methods, and kits for detecting expression of HER2 and/or a HER2 indicator marker in non-HER2-amplified cancer samples from a subject, and identifying the subject as responsive to treatment with a HER2 targeting agent and/or treating the subject with a HER2 targeting agent.

In particular embodiments, the present invention provides administering: a HER2 targeting agent (e.g., anti-HER2 antibody (e.g., Trastuzumab)), an IL6R targeting agent (e.g., anti-IL6R antibody (e.g., Tocilizumab)), an Akt targeting agent (e.g., Akt inhibitor (e.g., perifosine)), and/or co-administrating a combinations thereof to a subject (e.g., a subject suffering from cancer (e.g., non-HER2 amplified cancer (e.g., non-HER2 amplified cancer with cancer stem cells expressing HER2))).

In some embodiments, the present invention provides methods comprising: treating a subject with a HER2 targeting agent (e.g., anti-HER2 antibody (e.g., Trastuzumab)), wherein the subject has or has been identified as having: 1) non-HER2-amplified cancer (e.g., non-tumorigenic cells in a sample do not have amplified HER2), and 2) cancer stem cells that express HER2 and/or a HER2 indicator marker. In further embodiments, the methods further comprise, prior to the treating, receiving information that the subject, or a sample from the subject, has been identified as having: 1) the non-HER2-amplified cancer, and 2) the cancer stem cells that express HER2 and/or a HER2 indicator marker. In other embodiments, the subject is treated with the HER2 targeting agent as adjuvant therapy. In some embodiments, the subject is treated with the HER2 targeting agent as well as an IL6R targeting agent (e.g., Tocilizumab). In some embodiments, the subject is treated with perifosine, alone or in addition to the other agents. In certain embodiments, the IL6R targeting agent prevents formation of resistance to the HER2 targeting agent. In particular embodiments, after the treating, a sample from the subject is assayed to detect the expression of HER2 and/or a HER2 indicator marker, by cancer stem cells in a sample from the subject (e.g., a non-HER2-amplified cancer sample from a subject) to determine, for example, the effectiveness of treatment and/or to determine if further HER2 targeting agent treatment is needed. In additional embodiments, such additional treatment is provided (e.g., such that the patient is originally treated, then tested, and then treated again). In further embodiments, the subject is then further tested again for HER-2 amplification and HER2/HER2 indicator expression in the cancer stem cells.

In some embodiments, the present invention provides compositions and methods for preventing resistance of cancer cells and/or cancer stem cells to HER2 targeting agents (e.g., Trastuzumab). In some embodiments, an IL6R targeting agent (e.g., anti-IL6R antibody (e.g., Tocilizumab)) is administered to prevent resistance to HER2 targeting agents. In some embodiments, an Akt targeting agent (e.g., perifosine) is administered to prevent resistance to HER2 targeting agents. In some embodiments, perifosine and/or an IL6R targeting agent is co-administered with a HER2 targeting agent (e.g., Trastuzumab).

In some embodiments, the present invention provides compositions and methods for the treatment of cancer that interrupt and/or inhibit an IL6 inflammatory loop. In some embodiments, an IL6 inflammatory loop is responsible (or partially responsible) for resistance to HER2 targeting agents, expanding the cancer stem cell population, tumor growth, metastasis, etc. In such embodiments, compositions or methods that inhibit or interrupt the IL6 inflammatory loop further serve to prevent and/or inhibit the downstream effects thereof (e.g., resistance to HER2 targeting agents, expanding the cancer stem cell population, tumor growth, metastasis, etc.). In some embodiments, compositions that interrupt and/or inhibit the IL6 inflammatory loop include IL6R targeting agents agent (e.g., anti-IL6R antibody (e.g., Tocilizumab)), IL6 targeting agent, agent targeting an upstream or downstream actor in the IL6 inflammatory loop, etc. In certain embodiments, an agent that inhibits/interrupts the IL6 inflammatory pathway is coadministered with another agent. In particular embodiments, methods for treatment of cancer comprise coadministration of: (a) administration of an agent to interrupt/inhibit an IL6 inflammatory loop (e.g., an IL6R targeting agent (e.g., anti-IL6R antibody (e.g., Tocilizumab))), and (b) a cancer therapeutic agent (e.g., a HER2 targeting agent (e.g., Trastuzumab)). In other embodiments, an agent that inhibits/interrupts the IL6 inflammatory pathway is administered alone.

In certain embodiments, an IL6R targeting agent (e.g., anti-IL6R antibody (e.g., Tocilizumab)) is administered to a subject suffering from cancer (e.g., non-HER2-amplified cancer, HER2-amplified cancer, cancer comprising HER2-expressing cancer stem cells, etc.) to: reduce the cancer stem cell population, inhibit cancer stem cell population growth, reduce tumor size, slow tumor growth, inhibit tumor growth, prevent tumor growth, treat cancer while maintaining the body weight of the subject, block growth of therapeutic-resistant tumors (e.g., HER2 targeting agent resistant tumor), prevent tumor metastasis, etc. IL6 may be administered alone or in combination with one or more additional therapeutic agents (e.g., a HER2 targeting agent (e.g., Trastuzumab), Akt targeting agent (e.g., perifosine)).

In additional embodiments, the present invention provides methods comprising: a) detecting expression of HER2, and/or a HER2 indicator marker, by cancer stem cells in a non-HER2-amplified cancer sample from a subject, and b) administering a HER2 targeting agent to the subject, and/or identifying and/or reporting the subject as responsive to treatment with the HER2 targeting agent. In certain embodiments, the HER2 targeting agent is administered as adjuvant therapy to the subject. In some embodiments, the subject is treated with the HER2 targeting agent as well as an IL6R targeting agent. In certain embodiments, the IL6R targeting agent prevents formation of resistance to the HER2 targeting agent. In some embodiments, the subject is treated with perifosine, alone or in addition to the other agents. In particular embodiments, after the treating, a sample from the subject is assayed again to detect the expression of HER2 and/or a HER2 indicator marker, by cancer stem cells in a sample from the subject (e.g., a non-HER2-amplified cancer sample from a subject) to determine, for example, the effectiveness of treatment and/or to determine if further HER2 targeting agent treatment is needed. In additional embodiments, such additional treatment is provided (e.g., such that the patient is originally tested, then treated, then tested again, and then treated again).

In certain embodiments, the cancer sample from the subject is tested for HER2 amplification and HER2/HER2 indicator marker expression during the course of treatment (e.g., with HER2 targeting agent, with IL6R targeting agent, etc.), or immediately following a course of treatment, to determine if treatment should be continued or discontinued. In some embodiments, the testing lab provides such results and provides a recommendation on continuing or discontinuing treatment. In other embodiments, the attending physician receives the results and orders a continuation or discontinuation of treatment.

In particular embodiments, the non-HER2-amplified cancer sample is classified as Stage 1. In further embodiments, the subject has had any discernable tumors removed by surgery prior to the administering (e.g., all non-microscopic breast tumors have been removed). In further embodiments, the non-HER2-amplified cancer sample comprises a non-HER2-amplified breast cancer sample. In other embodiments, the non-HER2-amplified cancer sample comprises a non-HER2-amplified gastric cancer sample. In other embodiments, the cancer stem cells are breast cancer stem cells or gastric cancer stem cells. In other embodiments, the subject does not have any palpable tumors.

In certain embodiments, the HER2 indicator marker comprises ALDH1. In other embodiments, the non-HER2-amplified cancer sample comprises luminal breast cancer cells (e.g., ER positive). In further embodiments, the luminal breast cancer cells are ER positive. In additional embodiments, the methods further comprise: testing an initial cancer sample from the subject and determining that the initial cancer sample is a non-HER2-amplified cancer sample. In additional embodiments, the methods further comprise isolating the cancer stem cells from the non-HER2-amplified cancer sample prior to the detecting.

In some embodiments, the present invention provides kits or systems comprising: a) at least one amplification reagent for detecting HER2 amplification status in a cancer sample; and b) at least one expression reagent for detecting HER2, or HER2 indicator marker, expression in cancer stem cells. In other embodiments, the cancer sample comprises a breast cancer sample. In further embodiments, cancer sample comprises a gastric cancer sample or any other type of cancer sample. In particular embodiments, the cancer stem cells are breast cancer stem cells. In additional embodiments, the cancer stem cells are gastric cancer stem cells. In further embodiments, the at least one amplification reagent comprises an in-situ hybridization probe (e.g., FISH or CISH probe) for the HER2 gene. In certain embodiments, the at least one expression reagent comprises an anti-HER2 antibody or antigen-binding portion thereof. In additional embodiments, the at least one expression reagent comprises an anti-ALDH1 antibody or antigen-binding portion thereof. In certain embodiments, the kits or systems further comprise a buffer, instructions for performing the methods of the present invention, a packaging container, antibodies directed to cancer stem cell markers (e.g., CD44, CD24, or others discussed below). In certain embodiments, the HER2 targeting agent comprises a monoclonal antibody, chimeric antibody, humanized antibody, or antibody fragment. In particular embodiments, the HER2 targeting agent comprises HERCEPTIN.

In certain embodiments, the cancer sample is taken from the subject (e.g., at the point of care) and set to a testing lab (e.g., a remote testing lab or a lab within the same hospital or clinic setting as the patient). In certain embodiments, the cancer stem cells are purified from the cancer sample prior to being sent to (or being received by) the testing lab. In other embodiments, the cancer stem cells are not purified from the cancer sample before being sent to the testing lab (e.g., the testing lab purifies the cancer stem cells with cancer stem cell markers and detects expression of HER2 or a HER2 indicator marker in the purified cancer stem cells). In certain embodiments, the testing lab determines if the cancer sample is a non-HER2-amplified cancer sample and determines if the cancer stem cells express HER2 or a HER2 indicator protein. In particular embodiments, the cancer sample the HER2 amplification status is determined prior to sending to (or being received by) the testing lab (e.g., it is determined that the cancer sample is non-HER2 amplified prior to sending to the testing lab).

In particular embodiments, the testing lab sends results (e.g., written results) back to the point of care of the subject (e.g., to the hospital, clinic, attending physician, or subject) via electronic or paper communication. In certain embodiments, the electronic communication is an email, text message, or upload to a secured web site. In certain embodiments, the results of the HER amplification and HER2/HER2 indicator marker testing are stored in a computer system and optionally processed by the computer system to determine a recommendation for treating the subject. In particular embodiments, the testing lab determines that said subject is suitable for treatment for a HER2 targeting agent after determining that the cancer sample is non-HER2-amplified and that the cancer stem cells in the sample express HER2. In other embodiments, the treating physician receives the results from the testing lab regarding HER2 amplification status and cancer stem cell HER2/HER2 indicator expression status and determines whether the subject should be treated with a HER2 targeting agent. In certain embodiments, one testing lab determines the HER2 amplification status of the cancer sample and a different (separate) testing lab determines if the cancer stem cells in the cancer sample express HER2 or a HER2 indicator marker.

In certain embodiments, the HER2/HER2 indicator marker status is determined without purifying the cancer stem cells away from the bulks of the cancer cells in a cancer sample. In other embodiments, the cancer stem cells are purified away from the bulk of the cancer stem cells (e.g., by FACS type sorting, or in a single-cell array type analysis where each cell is present in its own well). In other embodiments, single-cell analysis is employed to assay both the cancer stem cells and the non-cancer stem cells in a sample (see, e.g., U.S. Pat. Pub. 201000240041 entitled "Microfluidic Device for Trapping Single Cells", and Hosokawa et al., Anal. Chem. 2009, July, 1:81(13):5308-13, entitled "High-Density Microcavity Array for Cell Detection: single-cell analysis of hematopoietic stem cells in peripheral blood mononuclear cells," both of which are herein incorporated by reference in their entireties. Single-cell analysis can determine for example, based on the results from the population of cells in the array, whether the bulk cancer stem cells are HER2 amplified and whether the cancer stem cells express HER2 or a HER2 indicator marker (e.g., using antibodies to cancer stem cell markers, such as CD44 and CD24, and antibodies to HER2 and/or ALDH1).

In some embodiments, the present invention provides compositions and methods for treatment or prevention of resistance to HER2 targeting agents (e.g., anti HER2 antibodies (e.g., trastuzumab)). In some embodiments, an anti-resistance agent (e.g., an IL6R targeting agent (e.g., anti-IL6R antibody (e.g., Tocilizumab)), Akt targeting agent (e.g., an Akt inhibitor (e.g., perifosine))) is administered to a subject to treat or prevent resistance to a HER2 targeting agent. In some embodiments, resistance to HER2 targeting agents is induced by administration of a HER2 targeting agent. In some embodiments, resistance to HER2 targeting agents is inherent to a cell, tumor, or cancer-type (e.g., de novo resistance). In some embodiments, an anti-resistance agent is co-administered with a HER2 targeting agent. In some embodiments, an anti-resistance agent and/or HER2 targeting agent is administered to subject with a non-HER2-amplified cancer that contains HER2 expressing cancer stem cells. In some embodiments, an anti-resistance agent and/or HER2 targeting agent is administered to subject with a HER2-amplified cancer. In some embodiments, an anti-resistance agent is administered before, during, or after treatment with a HER2 targeting agent.

In certain embodiments, the present invention provides administering an IL6R targeting agent (e.g., anti-IL6R antibody (e.g., Tocilizumab)) to a subject (e.g., a subject suffering from cancer). In some embodiments, administration of an IL6R targeting agent prevents and/or treats resistance to anti-cancer drugs (e.g., HER2 targeting agents), prevents tumor growth, reduces tumor size, decreases (or prevents increase of) the cancer stem cell population, prevents metastasis, and/or inhibits the IL6 inflammatory loop.

Examples of types of cancers that are treated and types of cancer samples tested include, but are not limited to, sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, gastric cancer, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

DESCRIPTION OF THE FIGURES

FIGS. 1c and 1d show Aldefluor activity overlaps with HER2 overexpression in HER2 non-amplified breast cancer cell lines. Mean of three independent experiment shows the percentage of HER2 overexpressing cells within Aldefluor population (c) and shows higher Aldelfuor activity in highest 10%-HER2 overexpressing cell population (d) in luminal cell lines (*p<0.05). Higher HER2 overexpression (green) demonstrated by immunofluorescence in Aldefluor-positive (f) compared with Aldefluor negative MCF7 (e).

DEFINITIONS

Figure 1:
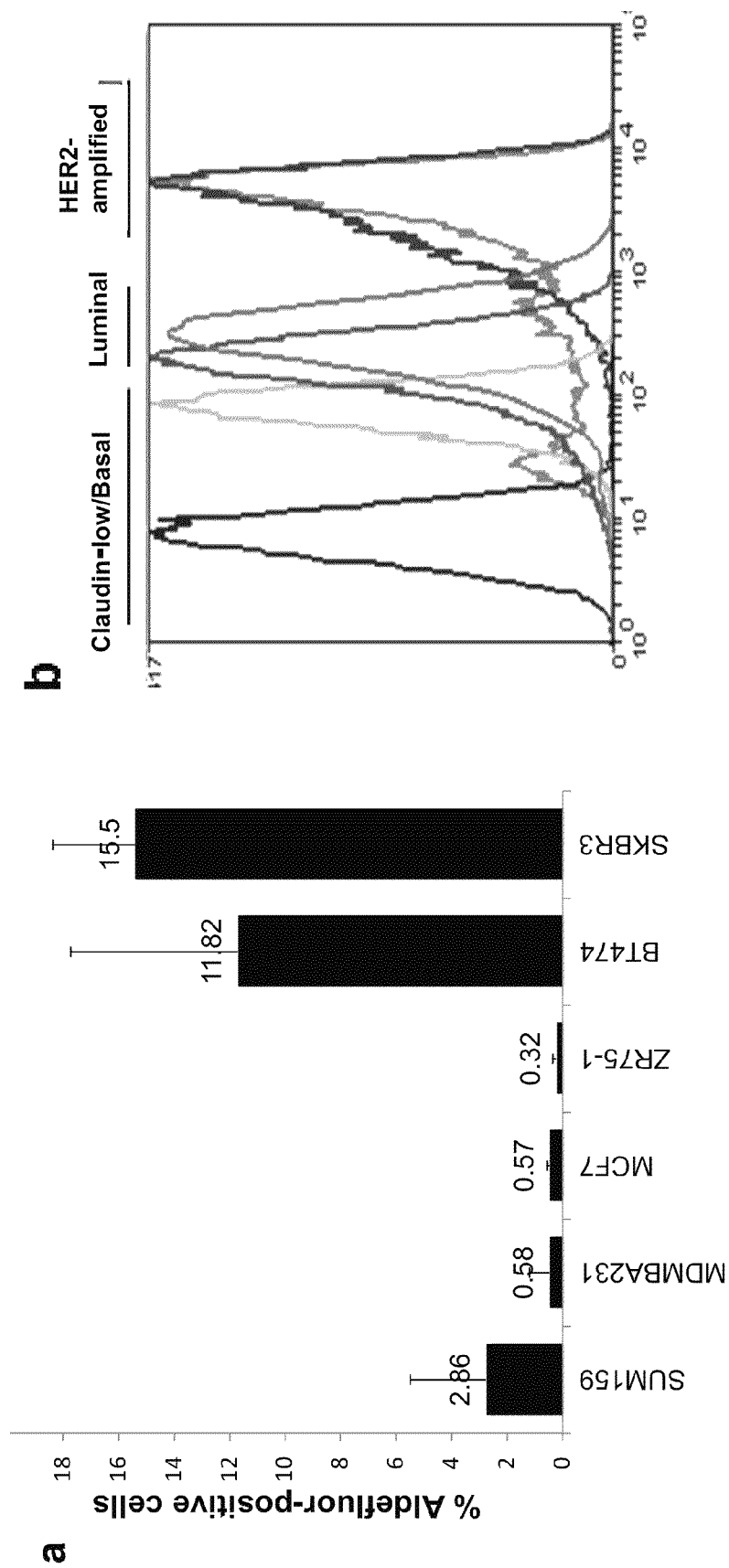
FIGS. 1a-f show the mean of three independent experiments which showed the percentage of Aldefluor positive cells in HER2 amplified (BT474, SKBR3), luminal (MCF7, ZR75-1) and basal (SUM159, MDMBA231) cell lines (a). (b), representative fluorescence-activating cell sorting analysis of MCF7, ZR75-1, SUM159, MDMBA231, BT474 and SKBR3 by using anti-HER2 antibody. There are lowest fluorescent intensity of HER2 in claudin-low/basal cell line (SUM159 in dark-blue line and MDMBA231 in light-blue line), followed by luminal cell lines (red: MCF7, pink: ZR75-1) and the extremely high HER2 expression in SKBR3 (light-grey) and BT474 (dark-grey).
Figure 1:
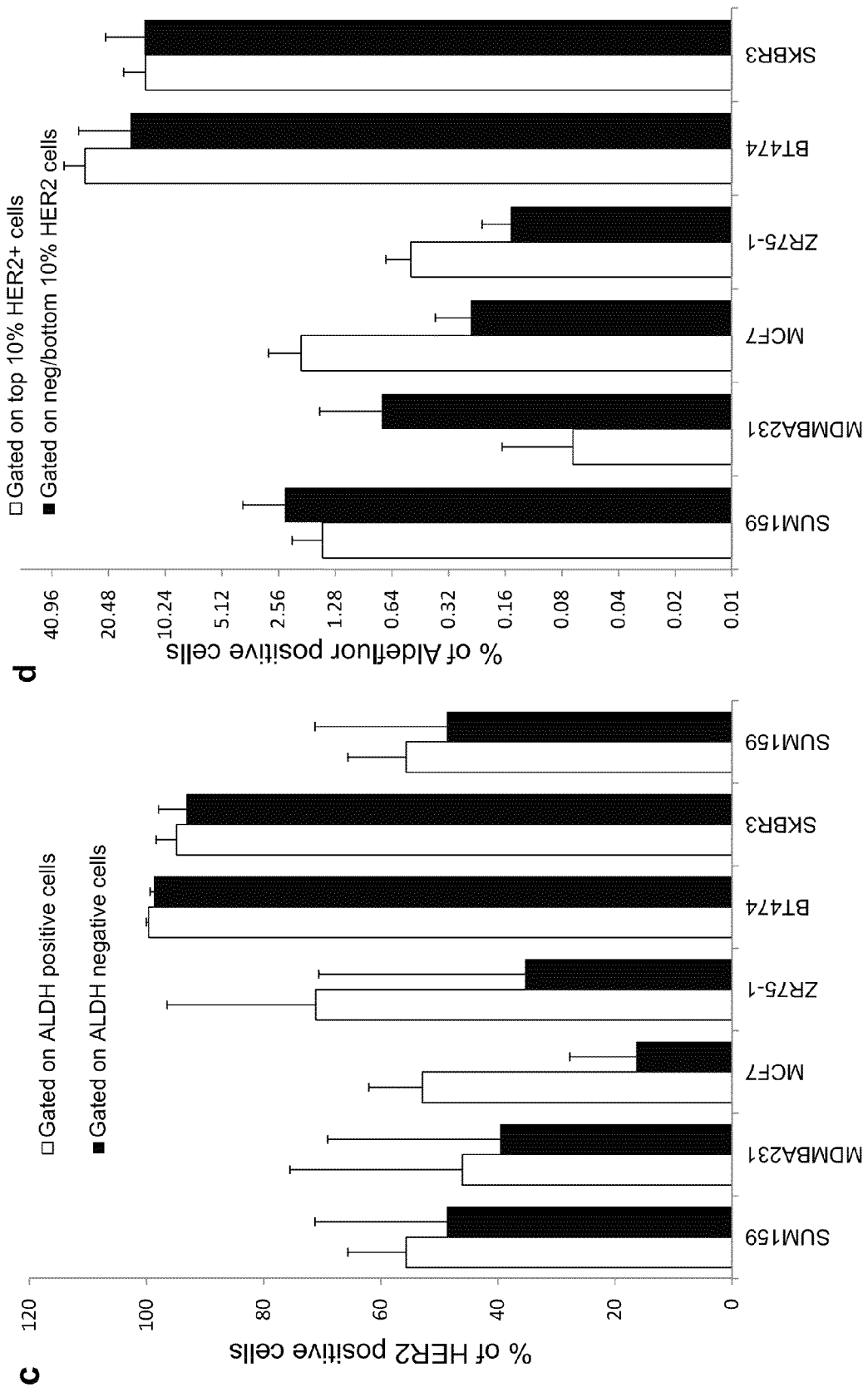
Figure 1:
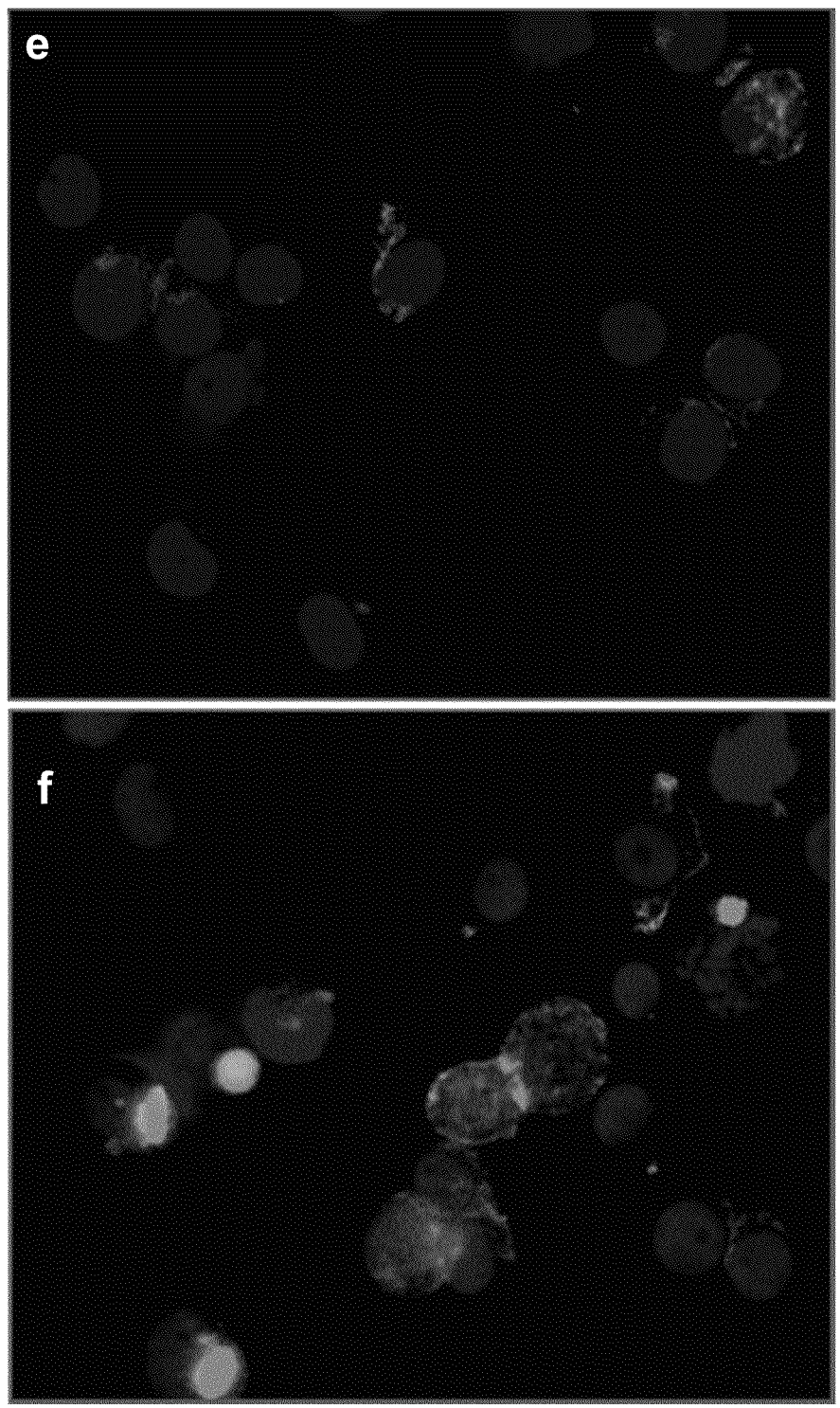

To facilitate an understanding of the present invention, a number of terms and phrases are defined below.

As used here, the term "antibody" includes monoclonal antibodies (including full length monoclonal antibodies), polyclonal antibodies, multispecific antibodies (e.g., bispecific antibodies), and antibody fragments so long as they exhibit the desired biological activity (e.g. able to bind to HER2 or protein in HER2 pathway, able to bind to IL6R or protein in IL6R pathway, etc.).

As used herein, the term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

As used herein, "humanized" forms of non-human (e.g., murine) antibodies are chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody can also comprise at least a portion of an immunoglobulin constant region (Fc), typically that of a human immunoglobulin. Examples of methods used to generate humanized antibodies are described in U.S. Pat. No. 5,225,539 to Winter et al. (herein incorporated by reference).

"Enriched," as in an enriched population of cells, can be defined phenotypically based upon the increased number of cells having a particular marker in a fractionated set of cells as compared with the number of cells having the marker in the unfractionated set of cells (e.g., an enriched population of cancer stem cells). However, the term "enriched can be defined functionally by tumorigenic function as the minimum number of cells that form tumors at limit dilution frequency in test mice. For example, if 500 tumor stem cells form tumors in 63% of test animals, but 5000 unfractionated tumor cells are required to form tumors in 63% of test animals, then the solid tumor stem cell population is 10-fold enriched for tumorigenic activity. Stem cell cancer markers can be used to generate enriched populations of cancer stem cells. In some embodiments, the stem cell population is enriched at least 1.4 fold relative to unfractioned tumor cells (e.g. 1.4 fold, 1.5 fold, 2 fold, 5 fold, 10 fold, . . . , 20 fold, . . . ).

"Isolated" in regard to cells, refers to a cell that is removed from its natural environment (such as in a solid tumor) and that is isolated or separated, and is at least about 30%, 50%, 75% free, or about 90% free, from other cells with which it is naturally present, but which lack the marker based on which the cells were isolated. The stem cell cancer markers of the present invention can be used to generate isolated populations of cancer stem cells.

As used herein, the terms "low levels," "decreased levels," "low expression," "reduced expression" or "decreased expression" in regards to gene expression are used herein interchangeably to refer to expression of a gene in a cell or population of cells, particularly a cancer stem cell or population of cancer stem cells, at levels less than the expression of that gene in a second cell or population of cells, for example normal breast epithelial cells. "Low levels" of gene expression can refer to expression of a gene in a cancer stem cell or population of cancer stem cells at levels: 1) half that or below expression levels of the same gene in normal breast epithelial cells and 2) at the lower limit of detection using conventional techniques. "Low levels" of gene expression can be determined by detecting decreased to nearly undetectable amounts of a polynucleotide (mRNA, cDNA, etc.) in cancer stem cells compared to normal breast epithelium by, for example, quantitative RT-PCR or microarray analysis. Alternatively "low levels" of gene expression can be determined by detecting decreased to nearly undetectable amounts of a protein in cancer stem cells compared to normal breast epithelium by, for example, ELISA, Western blot, or quantitative immunofluorescence.

The terms "high levels," "increased levels," "high expression," "increased expression" or "elevated levels" in regards to gene expression are used herein interchangeably to refer to expression of a gene in a cell or population of cells, particularly a cancer stem cell or population of cancer stem cells, at levels higher than the expression of that gene in a second cell or population of cells, for example normal breast epithelial cells. "Elevated levels" of gene expression can refer to expression of a gene in a cancer stem cell or population of cancer stem cells at levels twice that or more of expression levels of the same gene in normal breast epithelial cells. "Elevated levels" of gene expression can be determined by detecting increased amounts of a polynucleotide (mRNA, cDNA, etc.) in cancer stem cells compared to normal breast epithelium by, for example, quantitative RT-PCR or microarray analysis. Alternatively "elevated levels" of gene expression can be determined by detecting increased amounts of a protein in cancer stem cells compared to normal breast epithelium by, for example, ELISA, Western blot, quantitative immunofluorescence, etc.

The term "undetectable levels" or "loss of expression" in regards to gene expression as used herein refers to expression of a gene in a cell or population of cells, particularly a cancer stem cell or population of cancer stem cells, at levels that cannot be distinguished from background using conventional techniques such that no expression is identified. "Undetectable levels" of gene expression can be determined by the inability to detect levels of a polynucleotide (mRNA, cDNA, etc.) in cancer stem cells above background by, for example, quantitative RT-PCR or microarray analysis. Alternatively "undetectable levels" of gene expression can be determined by the inability to detect levels of a protein in cancer stem cells above background by, for example, ELISA, Western blot, or immunofluorescence.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The term "epitope" as used herein refers to that portion of an antigen that makes contact with a particular antibody.

When a protein or fragment of a protein is used to immunize a host animal, numerous regions of the protein can induce the production of antibodies which bind specifically to a given region or three-dimensional structure on the protein; these regions or structures are referred to as "antigenic determinants". An antigenic determinant can compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer can also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental exposure, previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers can be characterized by the identification of the expression of one or more cancer marker genes, including but not limited to, the cancer markers disclosed herein.

The terms "cancer stem cell," "tumor stem cell," or "solid tumor stem cell" are used interchangeably herein and refer to a population of cells from a solid tumor that: (1) have extensive proliferative capacity; (2) are capable of asymmetric cell division to generate one or more kinds of differentiated progeny with reduced proliferative or developmental potential; and (3) are capable of symmetric cell divisions for self-renewal or self-maintenance. These properties of "cancer stem cells," "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur.

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor.

As used herein, the terms "stem cell cancer marker(s)," "cancer stem cell marker(s)," "tumor stem cell marker(s)," or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the term "a reagent that specifically detects expression levels" refers to reagents used to detect the expression of one or more genes. Examples of suitable reagents include but are not limited to, nucleic acid probes capable of specifically hybridizing to the gene of interest, aptamers, PCR primers capable of specifically amplifying the gene of interest, and antibodies capable of specifically binding to proteins expressed by the gene of interest. Other non-limiting examples can be found in the description and examples below.

As used herein, "providing a diagnosis" or "diagnostic information" refers to any information that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

As used herein, the terms "providing a prognosis," "prognostic information," or "predictive information" refer to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the terms "biopsy tissue," "patient sample," "tumor sample," and "cancer sample" refer to a sample of cells, tissue or fluid that is removed from a subject for the purpose of determining if the sample contains cancerous tissue, including cancer stem cells that express HER2. In some embodiment, biopsy tissue or fluid is obtained because a subject is suspected of having cancer. The biopsy tissue or fluid is then examined for the presence or absence of cancer and cancer stem cells (e.g., examined to determine that the bulk non-tumorigenic cancer cells are non-HER2 amplified, and that the cancer stem cells express HER2).

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

As used herein, the term "sample" includes a specimen or culture obtained from any source, as well as biological and environmental samples. Biological samples can be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION OF THE INVENTION

The present invention relates to compositions, methods, and kits for treating cancers with HER2 targeting agents and preventing resistance thereto. In particular embodiments, non-HER2-amplified cancers are treated with HER2 targeting agents, wherein the cancer stem cells in the cancer express HER2 and/or HER2 indicator marker. The present invention also relates to compositions, methods, and kits for detecting expression of HER2 and/or a HER2 indicator marker in non-HER2-amplified cancer samples from a subject, and identifying the subject as responsive to treatment with a HER2 targeting agent and/or treating the subject with a HER2 targeting agent.

I. Detection and Treatment of HER2 Expressing Cancer Stem Cells

The cancer stem cell hypothesis posits that many tumors, including human breast cancer, are hierarchically organized and driven by a cellular subcomponent that displays stem cell properties (Wicha, M. S., Liu, S. & Dontu, G. Cancer Res 66, 1883-1890; discussion 1895-1886 (2006); herein incorporated by reference in its entirety). These cells drive tumor growth and metastasis and by virtue of their relative resistance to traditional therapies such as cytotoxic chemotherapy and radiation may contribute to treatment resistance (Shafee, N., et al. Cancer Res 68, 3243-3250 (2008); Hambardzumyan, D., Squatrito, M. & Holland, E. C. Cancer Cell 10, 454-456 (2006); Korkaya, H., et al. PLoS Biol 7, e1000121 (2009); Diehn, M., et al. Nature 458, 780-783 (2009); Li, X., et al. J Natl Cancer Inst 100, 672-679 (2008).); herein incorporated by reference in their entireties). Approximately 20% of human breast cancers display HER2 amplification, a molecular subtype associated with aggressive clinical behavior. The development of HER2-targeted therapeutics, such as trastuzumab, has had a dramatic impact on the natural history of HER2-positive disease. The current dogma that the benefit of HER2-targeted therapy is limited to breast cancers with HER2 amplification was based on both preclinical and clinical data. In early studies, it was demonstrated that trastuzumab inhibited growth in vitro and mouse xenografts of HER2 amplified breast cancer cell lines but had no demonstrable effects on luminal or basal breast cancer cell lines that did not display HER2 amplification (Slamon, D. J., et al. Science 235, 177-182 (1987); Mass, R. D., et al. Clin Breast Cancer 6, 240-246 (2005); Wolff, A. C., et al. J Clin Oncol 25, 118-145 (2007); herein incorporated by reference in their entireties). Furthermore, in women with advanced breast cancer, addition of trastuzumab to cytotoxic chemotherapy significantly increased the response rate, an effect that was limited to HER2 amplified tumors.

Based on these preclinical and clinical data suggesting that the efficacy of HER2 blockade was limited to HER2 amplified breast cancers, the expression of HER2 has been treated as a dichotomous variable. Determination of HER2 amplification by fluorescence in situ hybridization (FISH) is considered the gold standard for identifying this subset. In addition, it has been demonstrated that tumors that display high levels (3+) of HER2 expression are almost always associated with HER2 gene amplification and, thus, this has also been utilized as a surrogate for HER2 amplification. The development of technologies such as AQUA quantitative immunofluorescence assay, have enabled assessment of HER2 expression as a continuous variable.

In Example 1 below, the present application demonstrates heterogeneous expression of HER2 within luminal cell lines with HER2 preferentially expressed in the CSC populations as assessed by ALDH expression, mammosphere formation and tumor initiation in NOD/SCID mice. Furthermore, Example 1 confirmed the association of HER2 and ALDH1 expression at the individual cell level in human primary breast cancer tissues. To assess the role of HER2 in tumor growth, worked conducted during the development of embodiments of the present invention determined the effect of trastuzumab on tumor growth in HER2 amplified and non-amplified cell lines in vitro and in xenograft models. As had previously been reported, under standard culture conditions, inhibition of cell growth by trastuzumab was limited to HER2 amplified cell lines. Although it had no discernable effect on bulk tumor populations, trastuzumab was able to target the CSC populations in the luminal cell lines in MCF7 and ZR75-1 as assessed by mammosphere formation and Aldehyde dehydrogenase expression. This effect was not seen in basal cell lines.

Work conducted during the development of embodiments of the present invention demonstrated the important role of HER2 in the regulation of CSCs in luminal tumors using mouse tumor xenografts. HER2 expressing MCF7 cells had significantly greater tumor initiating capacity than HER2 non-expressing cells. To assess the functional role of HER2 in tumor growth, the effects of trastuzumab on the growth of luminal MCF7 and ZR75-1 were compared to the HER2 amplified BT474 cells. The Example provided below compared the effects of trastuzumab alone, the cytotoxic chemotherapy docetaxel or the combination on tumor growth in these xenograft models. It was found that the effects of trastuzumab were highly dependent on the timing of administration. When trastuzumab treatments were begun after palpable tumors had been established (late treatments) trastuzumab effects on tumor growth were limited to HER2 amplified tumors. However, when treatment was started one day after inoculation (early treatment) simulating adjuvant therapy, trastuzumab significantly reduced the growth of both luminal ZR75-1 and MCF7 cells, as well as the HER2 amplified BT474 tumors. Furthermore, the combination of adjuvant trastuzumab to cytotoxic chemotherapy, but not cytotoxic chemotherapy alone completely prevented tumor growth in these luminal tumors. These results support the cancer stem cell model which holds that tumor shrinkage in the advanced setting as assessed by the RECIST criteria largely reflect effects on bulk tumor populations. In HER2 amplified breast cancers virtually all of the cells express HER2 and so trastuzumab facilitates tumor regression reflected in an increased response rate. Furthermore, work conducted during the development of embodiments of the present invention indicate that in HER2 amplified cancers, although all cells express some level of HER2, Aldefluor-expressing CSCs have the highest level of expression. This suggests that in addition to amplification, HER2 protein expression is regulated by other pathways related to the CSS phenotype. These results suggest that trastuzumab will provide benefit in this setting in luminal non-HER2 amplified breast cancer in which HER2 is expressed in the cancer stem cell population.

Work conducted during the development of embodiments of the present invention demonstrates that HER2 expression may be regulated by the tumor microenvironment. Previous studies that have examined discordance between HER2 expression in primary tumors and at metastatic sites have suggested a discordance rate of 8-50%. Interestingly, discordance is higher when utilizing immunohistochemistry than FISH. Although a number of components within the bone microenvironment may favor tumor growth, evidence indicates that HER2 regulation may be an important factor.

MCF7 cells which express HER2 have increased capacity to grow in mouse femurs compared to those that do not express HER2. Furthermore, MCF7 cells growing in bone display higher levels of ALDH1 expression than those growing in the mammary fat pad. In order to demonstrate that components within the bone microenvironment are able to directly regulate HER2 expression, the Examples below employed a co-culture system utilizing mesenchymal stem cells derived bone osteocytes. It was demonstrated that co-culture of MCF7 cells with these human osteocytes induces greater than a three-fold increase in HER2 expression, an effect blocked by the RANK ligand inhibitor denosumab. Additionally, knockdown of HER2 utilizing a siRNA reduced the ability of MCF7 cells to grow in the femur as well as reducing the percent of ALDH expressing CSCs. As was the case with the fat pad model, the effects of trastuzumab on tumor growth within the femur are dependent on the time of administration. Although trastuzumab had little effect on established bone tumors, treatments were initiated on the day after inoculation trastuzumab dramatically reduced tumor growth in bone. It has been reported that approximately 30% of women with early stage breast cancer harbor occult micrometastasis in their bone marrow at the time of diagnosis, a state associated with a worse prognosis. In addition, work conducted during the development of embodiments of the present invention found that requirement of estrogen for tumor growth of MCF7 cells was dependent on the site of tumor growth. In the mammary fat pad MCF7 growth was dependent on estrogen supplementation. However, when inoculated in the femur, MCF7 cells grew in the absence of estrogen supplementation. These results are consistent with the known reciprocal regulation of ER and HER2 growth factor signaling.

The present invention provides an important advancement for therapeutic treatment in humans, particularly in the adjuvant setting. The development of adjuvant therapy strategies usually are composed of utilizing agents that have been demonstrated to cause tumor regression in advanced disease, after removal of primary disease. These strategies assume homogeneity of tumor cell populations. However, the CSC model and that data in this application question this assumption. Tumor regression in advanced disease reflects effects on bulk tumor populations whereas recurrence after adjuvant therapy may reflect effects on the CSC populations. As such, then effective adjuvant treatments will need to target and eliminate the cancer stem cell population.

II. Cancer Stem Cell Markers and Use in Purification

In certain embodiments, cancer stem cells are isolated from a sample prior to detecting the expression of HER2 or a HER2 indicator protein (e.g., ALDH1) in the cancer stem cells. Any type of cancer stem cell marker can be used, depending on the type of cancer, to purify/isolate cancer stem cells. Examples include, but are not limited to, CD44, CD24, ESA, CD20, CD105, CD90, CD326 (EpCAM), CD34, CD133, CD117, Sca-1, HES6, ALDH1, CD166, CEACAM6, CD59, and CD49f. Additional markers and methods of using such markers, are found in the following references: U.S. Pat. No. 6,984,522; U.S. Pat. No. 7,115,360; U.S. Pat. Pub. 2008/0260734; U.S. Pat. Pub. US 2006/0019256; U.S. Pat. Pub. 2007/0099209; U.S. Pat. No. 7,939,263; U.S. Pat. No. 7,723,112; and U.S. Pat. Pub. 2008/0261244, all of which are herein incorporated by reference as if fully set forth herein. In certain embodiments, the cancer stem cell markers are used as part of a FACS purification. In other embodiments, the cancer stem cell markers are used in any type of single-cell analysis, such as a single-cell array that detects on a single-cell and population basis whether a particular array cancer sample is non-HER-2 amplified in the non-cancer cells and expresses HER2 in the cancer stem cells (see, e.g., U.S. Pat. Pub. 201000240041 entitled "Microfluidic Device for Trapping Single Cells", and Hosokawa et al., Anal. Chem. 2009, July, 1:81(13):5308-13, entitled "High-Density Microcavity Array for Cell Detection: single-cell analysis of hematopoietic stem cells in peripheral blood mononuclear cells," both of which are herein incorporated by reference in their entireties.

The detection of cancer stem cell markers (e.g., for purification) and the detection of HER2 expression in cancer stem cells can be performed in any suitable manner, including FACS and the methods described below.

1. Detection of RNA

In some embodiments, detection of solid tumor stem cell cancer markers (e.g., for cancer stem cell purification) are detected by measuring the expression of corresponding mRNA in a tissue sample (e.g., breast cancer tissue). mRNA expression can be measured by any suitable method, including but not limited to, those disclosed below.

In some embodiments, RNA is detection by Northern blot analysis. Northern blot analysis involves the separation of RNA and hybridization of a complementary labeled probe.

In still further embodiments, RNA (or corresponding cDNA) is detected by hybridization to an oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S.

Pat. Nos. 5,639,606, 5,643,765, and 5,876,978 (each of which is herein incorporated by reference) is utilized.

2. Detection of Protein

In other embodiments, gene expression of stem cell cancer markers, and detection of HER2 expression in cancer stem cells, is detected by measuring the expression of the corresponding protein or polypeptide. Protein expression can be detected by any suitable method. In some embodiments, proteins are detected by immunohistochemistry. In other embodiments, proteins are detected by their binding to an antibody raised against the protein. In certain embodiment, the antibodies are used as part of a FACS purification. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In some embodiments, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981, 785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

III. HER2 Targeting Agents

The present invention is not limited by the HER2 targeting agent that is employed. Any agent that interferes with the activity (e.g., function or activation) of HER2 may be used as a HER2 targeting agent. For example, HER2 targeting agents may include, for example, small molecule HER2 antagonists, antisense molecules, siRNA molecules, and antibodies, antibody fragments (antigen binding fragments, such as Fv or Fab fragments).

Antibodies directed against the rat p185neu and human HER2 protein products have been described. Hudziak et al., Mol. Cell Biol. 9(3):1165-1172 (1989) describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-alpha. See also U.S. Pat. No. 5,677,171 issued Oct. 14, 1997. The HER2 antibodies discussed in Hudziak et al. are further characterized in Fendly et al. Cancer Research 50:1550-1558 (1990); Kotts et al. In Vitro 26(3):59A (1990); Sarup et al. Growth Regulation 1:72-82 (1991); Shepard et al. J. Clin. Immunol. 11(3):117-127 (1991); Kumar et al. Mol. Cell. Biol. 11(2):979-986 (1991); Lewis et al. Cancer Immunol. Immunother 37:255-263 (1993); Pietras et al. Oncogene 9:1829-1838 (1994); Vitetta et al. Cancer Research 54:5301-5309 (1994); Sliwkowski et al. J. Biol. Chem. 269(20): 14661-14665 (1994); Scott et al. J. Biol. Chem. 266:14300-5 (1991); D'souza et al. Proc. Natl. Acad. Sci. 91:7202-7206 (1994); Lewis et al. Cancer Research 56:1457-1465 (1996); and Schaefer et al. Oncogene 15:1385-1394 (1997); all of which are herein incorporated by reference.

A recombinant humanized version of the murine HER2 antibody 4D5 (huMAb4D5-8, rhuMAb HER2 trastuzumab or HERCEPTIN; U.S. Pat. No. 5,821,337, herein incorporated by reference). Trastuzumab received marketing approval from the Food and Drug Administration Sep. 25, 1998 for the treatment of patients with metastatic breast cancer whose tumors overexpress the HER2 protein. In November 2006, the FDA approved HERCEPTIN (trastuzumab) as part of a treatment regimen containing doxorubicin, cyclophosphamide and paclitaxel, for the adjuvant treatment of patients with HER2-positive, node-positive breast cancer. See also, Press et al., Cancer Res. 53:4960-4970 (1993); Baselga et al., Cancer Res. 58:2825-2831 (1998); Pegram et al., Proc. Am. Assoc. Cancer 38:602 (1997), Abstract 4044; Slamon et al., N. Engl. Med. 344:783-792 (2001); Lee et al., Nature 378:394-396 (1995); Romond et al., N. Engl. J. Med. 353:1673-1684 (2005); Ta-Chiu et al., J. Clin. Oncol. 7811-7819 (2005); all of which are herein incorporated by reference.

Other HER2 antibodies with various properties have been described in Tagliabue et al. Int. J. Cancer 47:933-937 (1991); McKenzie et al. Oncogene 4:543-548 (1989); Maier et al. Cancer Res. 51:5361-5369 (1991); Bacus et al. Molecular Carcinogenesis 3:350-362 (1990); Stancovsk et al. PNAS (USA) 88:8691-8695 (1991); Bacus et al. Cancer Research 52:2580-2589 (1992); Xu et al. Int. J. Cancer 53:401-408 (1993); WO94/00136; Kasprzyk et al. Cancer Research 52:2771-2776 (1992); Hancock et al. Cancer Res. 51:4575-4580 (1991); Shawver et al. Cancer Res. 54:1367-1373 (1994); Arteaga et al. Cancer Res. 54:3758-3765 (1994); Harwerth et al. J. Biol. Chem. 267:15160-15167 (1992); U.S. Pat. No. 5,783,186; and Klapper et al. Oncogene 14:2099-2109 (1997); all of which are herein incorporated by reference.

Additional patent publications related to HER antibodies include: U.S. Pat. No. 5,677,171, U.S. Pat. No. 5,720,937, U.S. Pat. No. 5,720,954, U.S. Pat. No. 5,725,856, U.S. Pat. No. 5,770,195, U.S. Pat. No. 5,772,997, U.S. Pat. No. 6,165, 464, U.S. Pat. No. 6,387,371, U.S. Pat. No. 6,399,063, US2002/0192211A1, U.S. Pat. No. 6,015,567, U.S. Pat. No. 6,333,169, U.S. Pat. No. 4,968,603, U.S. Pat. No. 5,821,337, U.S. Pat. No. 6,054,297, U.S. Pat. No. 6,407,213, U.S. Pat. No. 6,719,971, U.S. Pat. No. 6,800,738, US2004/0236078A1, U.S. Pat. No. 5,648,237, U.S. Pat. No. 6,267, 958, U.S. Pat. No. 6,685,940, U.S. Pat. No. 6,821,515, WO98/17797, U.S. Pat. No. 6,127,526, U.S. Pat. No. 6,333, 398, U.S. Pat. No. 6,797,814, U.S. Pat. No. 6,339,142, U.S. Pat. No. 6,417,335, U.S. Pat. No. 6,489,447, WO99/31140, US2003/0147884A1, US2003/0170234A1, US 2005/0002928A1, U.S. Pat. No. 6,573,043, US2003/0152987A1, WO99/48527, US2002/0141993A1, WO01/00245, US2003/0086924, US2004/0013667A1, WO00/69460, WO01/00238, WO01/15730, U.S. Pat. No. 6,627,196B1, U.S. Pat.

No. 6,632,979B1, WO01/00244, US2002/0090662A1, WO01/89566, US2002/0064785, US2003/0134344, WO 04/24866, US2004/0082047, US2003/0175845A1, WO03/087131, US2003/0228663, WO2004/008099A2, US2004/0106161, WO2004/048525, US2004/0258685A1, U.S. Pat. No. 5,985,553, U.S. Pat. No. 5,747,261, U.S. Pat. No. 4,935,341, U.S. Pat. No. 5,401,638, U.S. Pat. No. 5,604,107, WO 87/07646, WO 89/10412, WO 91/05264, EP 412,116 B1, FP 494,135 B1, U.S. Pat. No. 5,824,311, EP 444,181 B1, EP 1,006,194 A2, US 2002/0155527A1, WO 91/02062, U.S. Pat. No. 5,571,894, U.S. Pat. No. 5,939,531, EP 502,812 B1, WO 93/03741, EP 554,441 B1, EP 656,367 A1, U.S. Pat. No. 5,288,477, U.S. Pat. No. 5,514,554, U.S. Pat. No. 5,587,458, WO 93/12220, WO 93/16185, U.S. Pat. No. 5,877,305, WO 93/21319, WO 93/21232, U.S. Pat. No. 5,856,089, WO 94/22478, U.S. Pat. No. 5,910,486, U.S. Pat. No. 6,028,059, WO 96/07321, U.S. Pat. No. 5,804,396. U.S. Pat. No. 5,846,749, EP 711,565, WO 96/16673, U.S. Pat. No. 5,783,404, U.S. Pat. No. 5,977,322, U.S. Pat. No. 6,512,097, WO 97/00271, U.S. Pat. No. 6,270,765, U.S. Pat. No. 6,395,272, U.S. Pat. No. 5,837,243, WO 96/40789, U.S. Pat. No. 5,783,186, U.S. Pat. No. 6,458,356, WO 97/20858, WO 97/38731, U.S. Pat. No. 6,214,388, U.S. Pat. No. 5,925,519, WO 98/02463, U.S. Pat. No. 5,922,845, WO 98/18489, WO 98/33914, U.S. Pat. No. 5,994,071, WO 98/45479, U.S. Pat. No. 6,358,682 B1, US 2003/0059790, WO 99/55367, WO 01/20033, US 2002/0076695 A1, WO 00/78347, WO 01/09187, WO 01/21192, WO 01/32155, WO 01/53354, WO 01/56604, WO 01/76630, WO02/05791, WO 02/11677, U.S. Pat. No. 6,582,919, US2002/0192652A1, US 2003/0211530A1, WO 02/44413, US 2002/0142328, U.S. Pat. No. 6,602,670 B2, WO 02/45653, WO 02/055106, US 2003/0152572, US 2003/0165840, WO 02/087619, WO 03/006509, WO03/012072, WO 03/028638, US 2003/0068318, WO 03/041736, EP 1,357,132, US 2003/0202973, US 2004/0138160, U.S. Pat. No. 5,705,157, U.S. Pat. No. 6,123,939, EP 616,812 B1, US 2003/0103973, US 2003/0108545, U.S. Pat. No. 6,403,630 B1, WO 00/61145, WO 00/61185, U.S. Pat. No. 6,333,348 B1, WO 01/05425, WO 01/64246, US 2003/0022918, US 2002/0051785 A1, U.S. Pat. No. 6,767,541, WO 01/76586, US 2003/0144252, WO 01/87336, US 2002/0031515 A1, WO 01/87334, WO 02/05791, WO 02/09754, US 2003/0157097, US 2002/0076408, WO 02/055106, WO 02/070008, WO 02/089842 and WO 03/86467—all of which are herein incorporated by reference in their entireties.

IV. PTEN and IL6 Roles in Expansion of CSC Population

Experiments conducted during development of embodiments of the present invention demonstrated that PTEN deletion in multiple HER2-amplified breast cancer cell lines resulted in substantial increases in production of several cytokines, including IL6. IL6, in turn, was necessary to maintain a positive feedback loop that also expanded the CSC population as assessed by the Aldefluor assay or by expression of the cancer stem cell markers $CD44^+/CD24^-$. When HER2-amplified PTEN-deleted cells were cultured in the presence of the HER2− blocking antibody, trastuzumab, they demonstrated progressive increase in cytokine production as well as in the proportion of CSCs. LTT with trastuzumab of BT474-PTEN⁻ cells resulted in a several 100-fold increase in IL6 production associated with an increase in the $CD44^+/CD24^-$ cells from less than 1% to over 70%. In addition to increasing the CSC population, these cells assumed a mesenchymal appearance with increased expression of EMT markers such as vimentin, TGF-b, and Twist and decreased expression of epithelial markers including E-cadherin, EpCAM, and Claudin. IL6 has previously been reported to be an inducer of EMT, a state also associated with CSCs (Mani et al., 2008). Experiments conducted during development of embodiments of the present invention demonstrated that an IL6 receptor blocking antibody was able to prevent the increase in CSCs, EMT, and cytokine production, demonstrating a critical role for IL6 in maintaining this feedback loop. Long-term trastuzumab-treated cells became resistant to anti-IL6R antibody, suggesting that these cells may have undergone additional epigenetic changes.

Experiments conducted during development of embodiments of the present invention demonstrated that the IL6 inflammatory loop is dependent on NF-kB signaling. This transcription factor is known to regulate the production of a number of cytokines including IL6, IL8, and CCL5 (Yu et al., 2010). Although combined inhibition of Akt and STAT3 pathways was required to completely inhibit production of these cytokines, blocking IL6 or inhibiting the NF-kB pathway with Bay11 almost completely blocked cytokine production. An NF-kB reporter was used to demonstrate that there was an increase of greater than 3-fold in the proportion of NF-kB-activated cells upon PTEN downregulation. The aforementioned experiments suggest that activation of an IL6 inflammatory loop plays an important role in both de novo and acquired trastuzumab resistance. Activation of this inflammatory loop was dependent upon PTEN downregulation. However, experiments demonstrated that when parental BT474 cells were co-cultured with BT474/PTEN⁻/LTT (cultured long term in the presence of trastuzumab), the IL6 inflammatory loop was activated in parental BT474 cells with wild-type PTEN expression via an IL6-dependent paracrine mechanism. These experiments indicate that once the IL6 inflammatory loop is activated in PTEN-deleted cells, paracrine factors, including IL6, are able to activate similar loops in neighboring cells, even in the absence of genetic alterations. Suppression of PTEN expression by IL6 has previously been shown to be mediated by the microRNA miR21 (Iliopoulos et al., 2010). Consistent with this, experiments show that IL6 activates the Akt, Stat3, and NF-kB pathways while suppressing PTEN expression. Furthermore, IL6 has been shown to induce epigenetic alterations such as methylation in a number of genes including CD44, which is induced by IL6-mediated hypomethylation, resulting in basal/stem cell phenotype (D'Anello et al., 2010). This may explain stable phenotypic changes in parental BT474 or SKBR3 cells upon IL6 treatment.

The role of an IL6-mediated inflammatory loop in trastuzumab resistance was further demonstrated utilizing NOD/SCID xenograft models. Both SUM159/HER2⁺/PTEN⁻ and HER2 amplified BT474/PTEN⁻ cells generated rapidly growing highly metastatic tumors in NOD/SCID mice that exhibited de novo resistance to trastuzumab treatment. Furthermore, the addition of anti-IL6R antibody to trastuzumab prevented development of acquired trastuzumab resistance in mice bearing parental BT474 xenografts. As was the case in vitro, trastuzumab treatment of mice actually accelerated BT474-PTEN⁻ tumor growth and CSC frequency, as well as markedly increasing the level of secreted cytokines IL6 and IL8 as demonstrated by a human specific ELISA. This suggests that the IL6 inflammatory loop not only mediates de novo trastuzumab resistance, but also that further amplification of this loop is involved in acquired trastuzumab resistance.

The functional importance of this inflammatory loop was demonstrated, indicating that the IL6R antibody, alone or in combination with trastuzumab or the Akt inhibitor perifosine, not only decreased the population of CSCs in primary tumor but also completely inhibited development of distant metastasis. Furthermore, primary tumors treated with anti-IL6R alone or in combination with trastuzumab reduced the frequency of CSCs, while trastuzumab treatment alone resulted in enrichment of CSCs as demonstrated by serial dilution reimplantation assays. These results are consistent with our findings that IL6 regulates the CSC population, as well as the process of EMT, both of which have been linked to tumor metastasis.

V. IL6R Targeting Agents

The present invention is not limited by the IL6R targeting agent that is employed. Any agent that interferes with the activity (e.g., function or activation) of IL6R may be used as an IL6R targeting agent. For example, IL6R targeting agents may include, for example, small molecule IL6R antagonists, antisense molecules, siRNA molecules, and antibodies, antibody fragments (antigen binding fragments, such as Fv or Fab fragments). In fact, in some embodiments described herein as requiring an IL6R targeting agent, other agents that achieve the same end may be employed (e.g., IL6 targeting agent).

In some embodiments, IL6R targeting agents may include any composition that prevents, inhibits, or lessens the effect(s) of IL6R signaling. In certain embodiments, such agents may reduce the levels or activity of IL-6, IL-6 receptor alpha, IL6R, gp130, or a molecule involved in IL-6 or IL6R signal transduction, or may reduce the levels or activity complexes between the foregoing (e.g., reducing the activity of an IL-6/IL6R receptor complex). IL6R targeting agents include antisense nucleic acids, including DNA, RNA, or a nucleic acid analogue such as a peptide nucleic acid, locked nucleic acid, morpholino (phosphorodiamidate morpholino oligo), glycerol nucleic acid, or threose nucleic acid. See Heasman, Dev Biol. 2002 Mar. 15; 243(2):209-14; Hannon and Rossi, Nature. 2004 Sep. 16; 431(7006):371-8; Paul et al., Nat. Biotechnol. 2002 May; 20(5):505-8; Zhang et al., J Am Chem. Soc. 2005 Mar. 30; 127(12):4174-5; Wahlestedt et al., Proc Natl Acad Sci USA. 2000 May 9; 97(10):5633-8; Hanvey et al., 1992 Nov. 27; 258(5087):1481-5; Braasch et al., Biochemistry. 2002 Apr. 9; 41(14):4503-10; Schoning et al., Science. 2000 Nov. 17; 290(5495):1347-51; each of which is herein incorporated by reference in its entirety. In addition IL6R targeting agents specifically include peptides that block IL-6 signaling such as those described in any of U.S. Pat. Nos. 6,599,875; 6,172,042; 6,838,433; 6,841,533; 5,210,075 et al. Also, IL6R targeting agents according to the invention may include p38 MAP kinase inhibitors such as those reported in US20070010529 et al. Further, in some embodiments, IL6R targeting agents according to the invention include the glycoalkaloid compounds reported in US20050090453 as well as other IL-6 antagonist compounds isolatable using IL6R antagonist screening assays. Other IL6R targeting agents include antibodies, such as anti-IL-6 antibodies, anti-IL-6 receptor alpha antibodies, anti-IL6R antibodies, anti-gp130 antibodies, and anti-p38 MAP kinase antibodies including (but not limited to) the antibodies disclosed herein, ACTEMRA (Tocilizumab), REMICADE, ZENAPAX (daclizumab), or any combination thereof. Other IL6R targeting agents include portions or fragments of molecules involved in IL6R signaling, such as IL-6, IL-6 receptor alpha, and gp130, which may be native, mutant, or variant sequence, and may optionally be coupled to other moieties (such as half-life-increasing moieties, e.g. an Fc domain). For example, an IL6R targeting agents may be a soluble IL-6 or fragment, a soluble IL-6:Fc fusion protein, a small molecule inhibitor of IL6R, an anti-IL-6 receptor antibody or antibody fragment, antisense nucleic acid, etc. Other IL6R targeting agents include avemirs, such as C326 (Silverman et al., Nat. Biotechnol. 2005 December; 23(12):1556-61) and small molecules, such as synthetic retinoid AM80 (tamibarotene) (Takeda et al., Arterioscler Thromb Vasc Biol. 2006 May; 26(5):1177-83). Such IL6R targeting agents may be administered by any means known in the art, including contacting a subject with nucleic acids which encode or cause to be expressed any of the foregoing polypeptides or antisense sequences.

Anti-IL6R (Tocilizumab) is currently approved by the Food and Drug Administration for the treatment of rheumatoid arthritis, a condition in which IL6 plays a role in joint inflammation. Experiments conducted during development of embodiments of the present invention indicate that addition of agents targeting the IL6 pathway, such as anti-IL6R antibody, are a valuable addition to HER2-targeted agents for treatment of HER2+ breast cancer.

EXPERIMENTAL

The following examples are provided in order to demonstrate and further illustrate certain some embodiments and aspects of the present invention and are not to be construed as limiting the scope thereof.

EXAMPLE 1

HER2 is Expressed in Cancer Stem Cells in Non-Her2-Amplified Breast Cancer

Utilizing breast cancer cell lines, mouse xenograft models and human primary and metastatic tissue, this Example demonstrated that HER2 is selectively expressed in the cancer stem cell population in ER-positive luminal breast cancers. Although trastuzumab has no effects on the growth of established mouse xenograft administration after tumor inoculation, it blocks subsequent tumor growth. In luminal tumors, HER2 expression is induced in the bone microenvironment in mouse xenografts, as well in matched primary and bone metastases from patients. This Example indicates that the clinical efficacy of adjuvant trastuzumab (and other HER2 targeting agents) may relate to the ability of this agent to target the cancer stem cell population in a process that does not require HER2 amplification. This Example highlights the importance of targeting cancer stem cell populations in the development of adjuvant treatment strategies.

Material and Methods

Cell Culture and Treatment

Human breast cancer cell lines, MCF7, ZR75-1, BT474, SKBR3 and SUM159 were employed. The MCF-7 cell line was obtained from ATCC and fingerprinting was done on the MCF-7shHER-2 and MCF-7shVector cell lines, validating that they were MCF-7 prior to injections into tibiae. Cell lines were grown using recommended culture condition. Trastuzumab was obtained from the Pharmacy, University of Michigan Comprehensive Cancer Center. Trastuzumab at dosage of 20 μg/μl was added to monolayer or mammosphere culture on following day after plating and maintained for 7-day treatment.

Flow Cytometry and Aldefluor Assay

The Aldefluor kit (Stemcells Technology) was used according to the manufacturer's protocol to identify and isolate the population with high Aldehyde dehydrogenase activities using flow cytometry. To distinguish between ALDH-positive and ALDH-negative cells, a fraction of cells were incubated under identical condition in the presence of 10-fold molar excess of ALDH inhibitor, diethylaminobenzaldehyde (DEAB). Both samples and negative control were incubated in 37° C. for 40 minutes. For FACS analysis the gates were normalized with the Aldefluor-stained cells treated with DEAB.

Preparation of cells for FACS analysis and sorting was described as followings. Cells were collected and rinsed twice in 1×PBS containing 2% FBS and a fraction of cells were added with human immunoglobulin to identify nonspecific binding and use these cells as a gate for negative control. Cells were incubated with appropriate antibody dilution as manufacture's guidelines. The antibody included anti-HER2/neu APC (Biosciences, Cat#340554), anti-HER2/neu PE (Biosciences, Cat#340552).

Immunostaining

Sorted Aldefluor positive and negative population were prepared using cytospin technique of 700 rpm in 7 minutes and then fixed with cold 95% methanol stored at −20° C. Cells were rehydrated with PBS and incubated using HER2 mouse antihuman antibody (diluted 1:200, Neomarkers) at room temperature for 1 hour. Then, slides were washed and incubated with FITC conjugated donkey anti-mouse secondary antibody (1:250, Jackson Immuno Research Laboratories Inc.) for 30 minutes. The nuclei were counterstained with DAPI antifade reagent (Invitrogen, Lot 838018) and coverslipped. The slides were examined under fluorescent microscope.

For all IHC, 4.0μ sections were cut for staining. Mouse and human sections stained for HER-2 with anti-HER-2/Neu (Ab 17) (Labvision), anti-HER-2/Neu (Ab 17) (Labvision) and anti-HER-2/Neu (Dako), anti-Estrogen Receptor, and Aldehyde dehydrogenase 1. Staining was done using an Invitrogen kit and counterstained with hematoxylin. Diagnoses of low vs. high levels of HER-2 protein in BrCa is graded on a scale of (0 to 3+) in clinical laboratories, where 2+ and 3+ staining is believed to be an indicator of HER-2 overexpression of the HER-2 gene, signifying a HER-2-positive cancer. This same measure of staining was utilized in all cases in this Example (in vitro and in vivo) and employed the HER-2 FISH assay on all tissues described herein.

For bone decalcification process prior to immunostaining, bones were decalcified in Decalcifier II (Leica Biosystems) for three hours at room temperature. Decalcified bones and soft tissue tumors were paraffin embedded; histological sections were cut at 4 μm thickness and stained with hematoxylin and eosin (H & E). All soft tissues analyzed were fixed in formalin and then in 70% ETOH prior to embedding and sectioning.

ALDH-1 and HER-2 Quantitation

IHC was carried out for HER-2 and ALDH-1 as described above. Tumor area was determined based on cytokeratin staining and areas of interest were identified. Photomicrographs were generated and either 200 or 500 cells per case were counted at 60× magnification. Results were reported as percentage of positive cells per total number of cells counted.

Mammosphere Assay and Dissociation

Mammosphere assay of cells with or without trastuzumab treatment were performed following established protocol. Single cells were initially plated on ultralow attachment plate at a density of 100,000 cells/ml with serum-free mammary epithelial basal medium (Mammocult, Stemcell Technologies). Mammosphere were counted manually under light microscope on the 7th day. Then, mammosphere dissociation was performed and re-cultured with the density of 10,000 cells/ml and further assessed for secondary and tertiary mammosphere formation. Efficiency of sphere forming was analyzed from at least 3 independent repeats.

Proliferation Assay

MTT (3-(4,5-Dimethylthiazol-2-yl)-2,5-diphenyltetrazolium bromide) assay was used to determine the effect of trastuzumab to cell growth under attached condition. Five thousand cells were plated on 96-well plate under regular media with or without trastuzumab treatment of 20 μg/μl. On day 3, 20 μl of 5 mg/ml MTT solution was added to each well and incubate for 3.5 hours at 37° c. After removing media, add MTT solvent (4 mM HCl, 0.1% Nondet P-40 in isopropanol) and read absorbance at 590 nm using spectrophotometry. The absorbance of treatment groups were calculated as percentage of viable cells compared to control groups.

Lentivirus Infection

For luciferase gene transduction, MCF7, ZR75-1, BT474 were incubated overnight with mixture of lentivirus supernatants Lenti-LUC-VSVG in culture medium (Vector Core). After that, cells were subcultured as regular basis and tested to confirm luciferase activity prior to inoculation into mice.

Western Blot

Western blot was done to confirm efficacy of HER2 knockdown MCF7 cells. MCF7shHER2 and MCF7shVector were harvested by mechanical disruption with cell scrapers followed by centrifugation. Cell lysates were prepared by lysing the cell pellets in RIPA buffer (Millipore) as per the instructions of the manufacturer. Protein estimation was done by Bradford protein assay reagent (Bio-Rad, Hercules, Calif.) and equal amount of proteins were loaded on (10%) SDS-PAGE followed by transfer to 0.2 μm nitrocellulose membrane (Optitran BA-S 83). After overnight incubation of the membrane with anti HER-2 primary antibody and necessary washings, secondary HRP labeled antibody (Bio-Rad) were added. Membranes were developed on X-ray film using ECL reagent (Millipore, WBKLSO) as described by the manufacturer. Actin (Sigma) was used as internal control. Secondary antibodies from BioRad Goat anti-rabbit and anti-mouse were used, respectively.

Mice and Xenograft Models, Treatment and Monitoring

Five-week old NOD/SCID mice from breeding colony, University of Michigan, Harland and Jackson Laboratory were used throughout the experiments. All experiments involving live mice were conducted in accordance with standard operating procedures approved by University Committee on the Use and Care of Animals at the University of Michigan (ULAM). An estrogen pellet was subcutaneously implanted in each mouse with the fat pad injection of MCF7 or ZR75-1 cells. Mice were sacrificed when tumor reached 1-1.2 CM.

Tumorigenicity of HER2 expressing versus HER2 nonexpressing MCF7 was assessed in 10 NOD/SCID mice. Sorted HER2 positive and negative cells were washed with serum-free PBS and were then resuspended in metrigel. Fat pads were cleared and injected with sorted HER2 positive or negative MCF7 cells at a dilution of 10,000 and 200,000 cells. To further determine the importance of HER2 in tumorgenicity addition to known CSC property, serial dilution of 1,000 and 5,000 cells of MCF7 subpopulation sorted by Aldefluor and HER2 status; Aldefluor−/HER2−, ALDH−/HER2+, ALDH+/HER2− and ALDH+/HER2+, were then injected into mammary fat pad with 12-week of tumor monitoring. Tumor initiation capacity in each subgroup was compared using limiting dilution analysis.

A xenograft model was used to simulate clinical disease in adjuvant (early treatment) and advanced (late treatment) setting. 5 mice per treatment group were used. For adjuvant setting, 50,000 cells of BT474, ZR75-1 and MCF7 were injected into fat pads and began treatment immediately after inoculation. To simulate advanced disease, 1 million cells of BT474, ZR75-1 and MCF7 were inoculated into fat pads and tumors allowed to reach a size of approximately 0.4 cm. Then, treatment described below was initiated and continued along with assessment of tumor growth for 6-week period. Animals were sacrificed right after completion of 6-week treatment and cancer stem cells were analyzed by Aldefluor assay as described previously.

For tibia injection, 7-8 weeks old NOD/SCID mice were firstly punctured at right tibia with 27 gauge needles in order to create a guide hold in knee cap, and then 1 million cells of MCF7 in 50 μl of saline were injected into their right tibia using 1 ml tuberculin syringe. Uninjected left tibia served as a control. Mice were then followed for 4 to 8 weeks. Females were sacrificed at 8 weeks or when a tibial tumor was apparent by sight or Faxitron radiography (Faxitron x-ray Corp., Wheeling, Ill.), whichever came first. Tibiae were surgically isolated and fixed in 10% buffered formalin followed by 70% EtOH. After fixation, tibiae were de-calcificafied, paraffin embedded and subjected to IHC for bone tumor analysis. Each tibia bone was fixed and scanned on the p-Dexa machine, prior to decalcification. Readings were taken for all tibiae injected and control (non-injected left legs) was also analyzed.

Treatment

NOD/SCID mice implanted with luciferase-labeled cells received 6-week of treatment in both advanced and adjuvant setting. This Example first determined the effect of trastuzumab (20 mg/kg) in both early- and late-treatment to MCF7 xenograft in both mammary fat pad and tibia. Then, to simulate current clinical setting using trastuzumab combined with chemotherapy, this example further tested the following treatment groups for BT474 and ZR75-1 xenografts: 1) control; 2) trastuzumab of 4 mg/kg intraperitoneal injection (IP) twice a week; 3) docetaxel of 10 mg/kg IP once a week; 4) trastuzumab plus docetaxel.

Tumor Monitoring

Fat pad tumor diameter was measured by caliper weekly. Tumor volumes were calculated using the formula: volume=width$^2$×length/2. Luciferase-labeled tumor growth was monitored at least every 2 weeks using in vivo imaging system (ISVS, Caliper Life Science). Mice were injected with luciferin (Caliper), anesthetized and imaged according to manufacturer's protocols. For photon flux counting, a charge-coupled device camera system (Xenogen) with a nose-cone isofluorane delivery system and heated stage for maintaining body temperature was used. Results were analyzed after 10 minutes of exposure using the Living Image software provided with the Xenogen imaging system.

Tumors and Patients

Formalin-fixed, paraffin-embedded tissue blocks (FFPE) of primary and bone metastatic breast cancers were obtained from the files of the Department of Pathology, University of Michigan Medical Center, Ann Arbor, Mich. IRB approval was obtained and the diagnosis was confirmed by morphology. Serial sections were cut and stained using routine immuno-histochemical methods for ER (DAKO, Carpinteria, Calif., clone 1D5, M7047, 1:50), PgR (DAKO, clone PgR636, M3569, 1:50), HER2 (DAKO, A0485, 1:100), Ki-67 (DAKO, clone MIB-1, M7240, 1:100). Stained slides were digitized and scored using an APERIO digital system. Intrinsic subtype was assigned as follows: LumA (ER>5%, any PgR, HER2−, Ki-67<13%), LumB (ER>5%, any PgR, HER2+, Ki-67>13%), HER2 (ER−, PgR−, HER2+, any Ki-67) and Basal (triple negative, ER−, PgR−, HER2−, any Ki-67) as described by Nielson et al (2010) Clin. Canc. Res. 16(21): 5222-5232 (herein incorporated by reference).

Immunohistochemical Staining and AQUA Analysis.

Triple immunofluorescence staining was performed as previously described (Neumeister et al (2010) Am. J. Pathol. 176(5): 2131-2138). Briefly, after deparaffinization and rehydration, slides were subjected to microwave epitope retrieval in 7.5 mM sodium citrate buffer, pH6. After rinsing several times in 10 mM Tris HCL buffer, pH 8 containing 0.154 M NaCl (TBS), endogenous peroxidase activity was blocked with 2.5% (v/v) H2O2 in methanol for 30 mins Non-specific binding of the antibodies was extinguished by a 30 min incubation with "Background Sniper" (BioCare Medical, Concord, Calif.). The slides were then incubated with the tumor specific antibody, CK8 (NOVUS, Cambridge, Mass., NB600-1117, Chicken polyclonal antibody, 1:1000) and ALDH1 (BD Transduction, San Jose, Calif., cat #611195, clone 44, 1:500) overnight at 4 C. The slides are then washed with TBST twice for 5 minutes and then once with TBS for 5 minutes. The slides are then incubated with the antibody to HER2 (DAKO, A0485, rabbit polyclonal antibody, 1:1000) for 60 mins at room temperature. Slides are then washed as described above and incubated with a combination of goat anti chicken IgY conjugated to AF555 (Molecular probes, Carpinteria, Calif., A21437, 1:200), goat anti-rabbit IgG conjugated to AF488 (Molecular probes, Carpinteria, Calif., A11008, 1:200) in goat anti mouse Envision+ (DAKO) for 60 minutes at room temperature in a dark humidity tray. The slides were then washed as described above and the target images were developed by a catalyzed signal amplification reaction of Cy5 labeled tyramide (PerkinElmer, Waltham, Mass., 1:50). The slides were washed with 3 changes of TBS and stained with the DNA staining dye 4',6-diaminodo-2-phenylindole (DAPI) in a non-fading mounting media (ProLong Gold, Molecular probes, Carpinteria, Calif.). The slides were allowed to dry overnight in a dark dry chamber and the edges are sealed. A cell line microarray containing cell lines known to be HER− (MCF7), normal expression of HER2 (HS578T) and amplified for HER2 (SKBR3 and MBA-361) were included in each run to ensure minimal run to run variability.

The AQUA system (HistoRx, New Haven, Conn.) was used for the automated image acquisition and analysis. Briefly, each scanned whole section is divided into segments, so that the whole section is covered irrespective of the segments tumor cell concentration. Each segment's images were captured with an Olympus BX51 microscope at 4 different extinction/emission wavelengths. Within each segment, the area of tumor is distinguished from stromal and necrotic areas by creating a tumor specific mask from the anti-CK8 protein, which is visualized from Alexafluor 555 signal. The DAPI image is then used to differentiate between the cytoplasmic and nuclear staining within the tumor mask. Finally, the fluorescence pixel intensity of the HER2 and ALDH1 protein/antibody complex is obtained from the AF488 and Cy5 signals respectively and reported as the AQUA score for each segment, corrected for the degradation of the light source over time. In order to compensate for the heterogeneity and concentration of tumor cells across a section, the sum of the AQUA scores for ALDH1 and HER2 were divided by the sum of the CK8 pixel intensity across the whole section.

Statistical Analysis

Results are presented as mean±standard deviation or mean±standard error of mean for at least 3 repeated individual in vitro or in vivo experiments, respectively, for each group. Student t-test was used comparing continuous variables. Median time to tumor formation was analyzed using Log rank test and Kaplan Meier method. SPSS version 13 was used for statistical analysis. P-value of less than 0.05 was considered statistically significant.

Results

Figure 7:
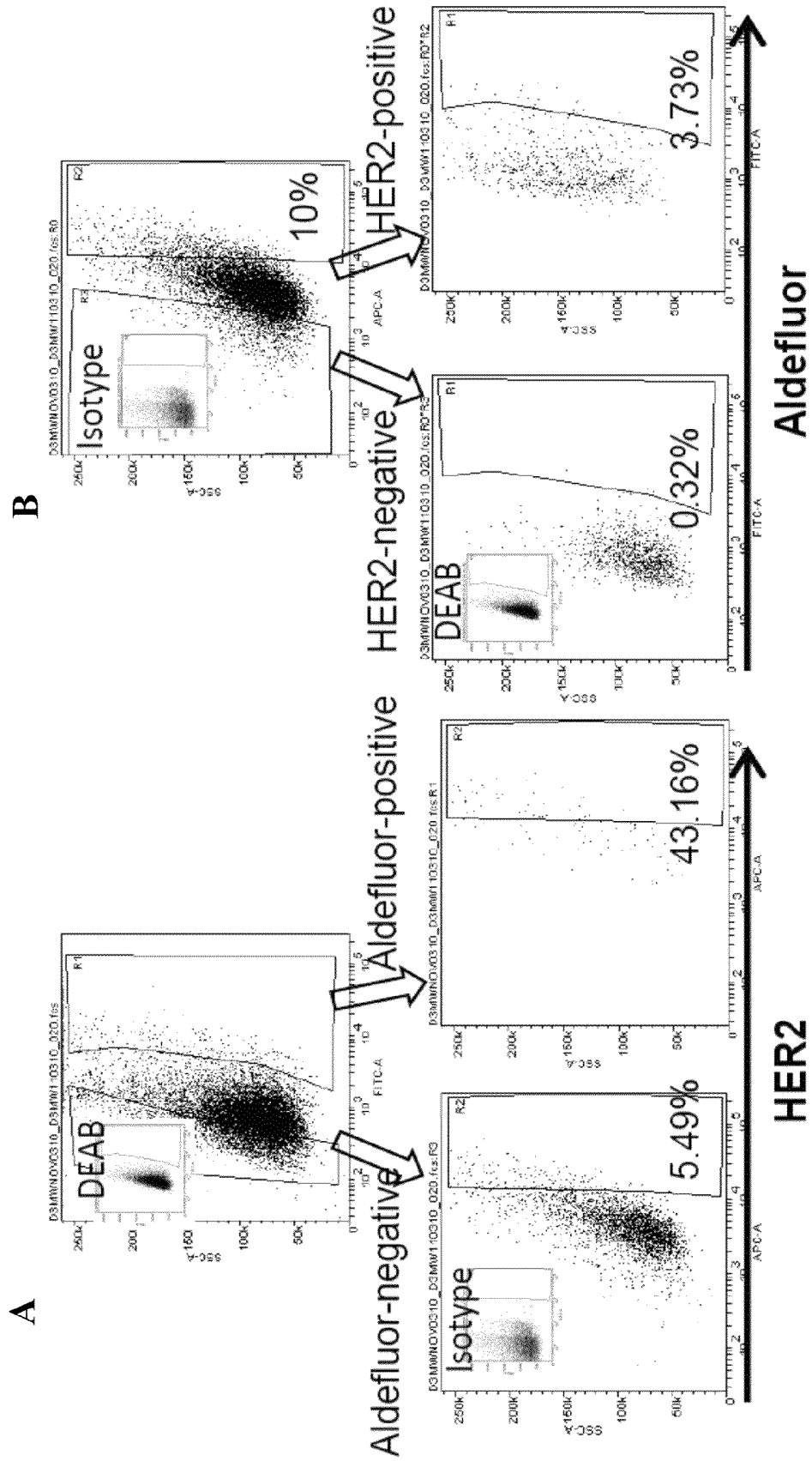
FIGS. 7a and 7b show MCF7 cells are co-labeled with anti-HER2-APC antibodies and Aldefluor and then analyzed by flow cytometry. Aldefluor-positive cells also co-expressed higher HER2 protein (a) and cells with higher HER2 expression enriched the Aldefluor-positive population (b)

Expression of HER2 Correlates with Expression of the CSC Marker Aldehyde Dehydrogenate (ALDH) in Luminal Breast Cancer Cell Lines It was previously demonstrated that normal and malignant breast cancer stem cells are characterized by expression of ALDH as assessed by the Aldefluor assay[20]. Furthermore, established breast cancer cell lines show a similar hierarchical organization with aldehyde dehydrogenase expressing cells displaying tumor initiating characteristics[21]. This Example utilized the Aldefluor assay to assess the percentage of aldehyde dehydrogenase expressing cells in luminal, basal and HER2 amplified breast cancer cell lines. As shown in FIG. 1a, luminal breast cancer cell lines, MCF7 and ZR75-1, displayed the lowest level of aldehyde dehydrogenase expression with less than 1% of cells Aldefluor-positive. In contrast, the HER2 amplified BT474 and SKBR3 displayed greater than 10% Aldefluor positivity. Basal breast cancer cell lines, SUM159 and MDA-MB231, displayed an intermediate level of Aldefluor positivity. The level of HER2 expression was assessed in these cell lines by flow cytometry. HER2 expression was heterogeneous both within and between cells lines. However, different molecular subtypes of breast cancer represented by these cell lines expressed quantitatively different levels of cell membrane HER2 (FIG. 1b). As expected, the HER2 amplified BT474 and SKBR3 cell lines expressed the highest levels of HER2. Basal/Claudin-low, SUM159 and MDA-MB231 cell lines expressed the lowest levels of HER2 and the luminal estrogen receptor-positive cell lines MCF7 and ZR75-1 displayed an intermediate level of HER2 expression. Flow cytometry was utilized to determine the relationship between HER2 and ALDH expression at the individual cell level. Virtually all of the cells within the BT474 and SKBR3, HER2 amplified populations, displayed HER2 expression. However, when cells expressing the highest levels of HER2 were compared to those expressing the lowest levels of HER2 within these populations there was an enrichment for high HER2 expression in the Aldefluor-positive populations. In luminal cells lines MCF7 and ZR75-1, the level of HER2 expression was considerably lower than in amplified cell lines. However, Aldefluor-positive cells were enriched in HER2 expression 2-3 fold compared to Aldefluor-negative cells (FIG. 1c). This association was seen when cells were first gated on the ALDH-positive population or, conversely when HER2-high and -negative/low cells were separated and assessed for ALDH expression (FIG. 1d, FIG. 7). In contrast to the association between HER2 and ALDH expression in luminal and HER2 amplified cell lines, the basal cell lines SUM159 and MDA-MB231 showed no association between HER2 and ALDH expression (FIGS. 1c and 1d). Flow cytometry results showing a concordance between HER2 and ALDH1 expression in MCF7 luminal cells at the individual cell level was confirmed by immunofluorescence (FIGS. 1e and 1f).

Figure 2:
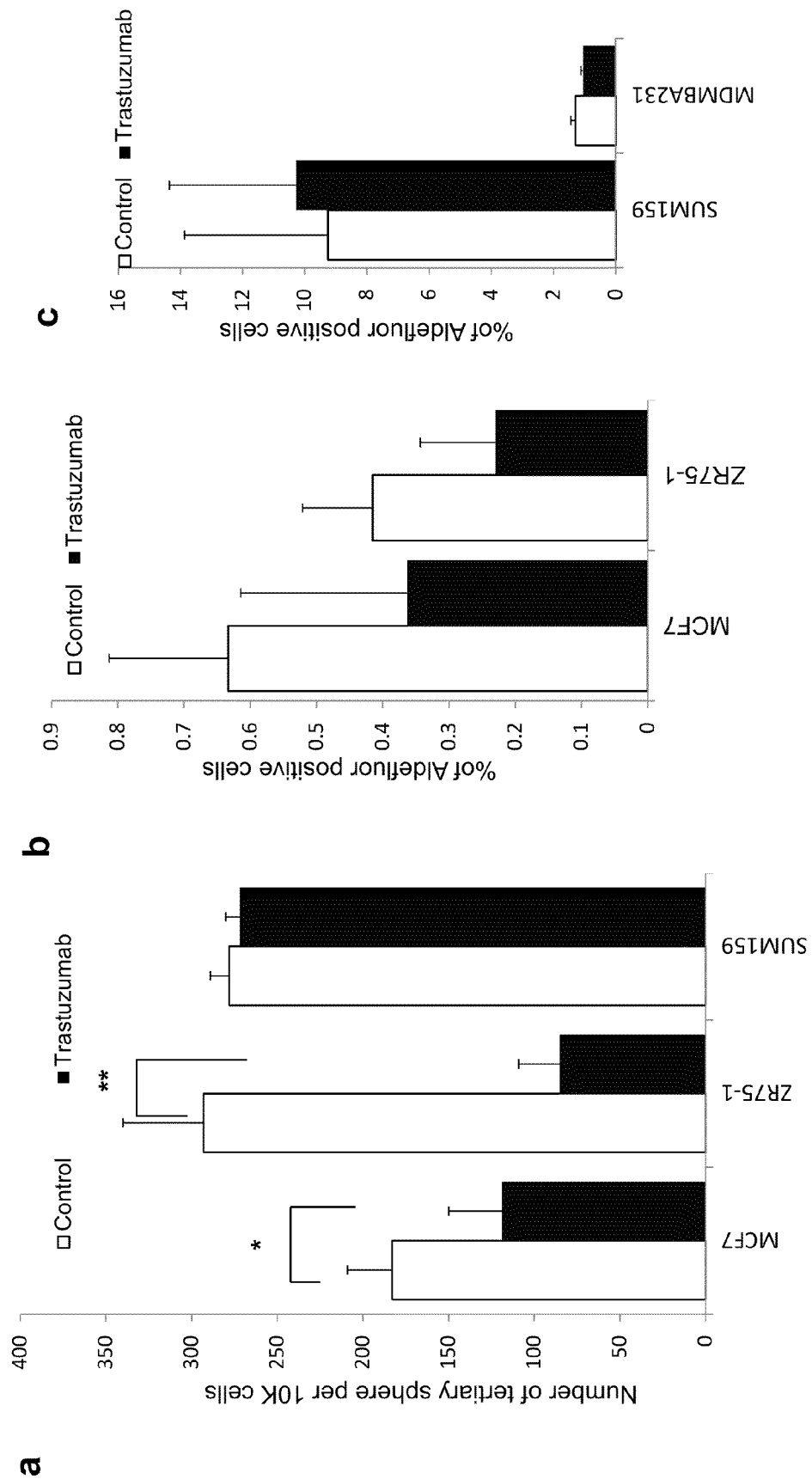
FIGS. 2a-f show the effects of trastuzumab on CSC in vitro. Trastuzumab suppressed mammosphere formation in luminal cell lines. MCF7 and ZR75-1 cells with 1-week of trastuzumab treatment generated significantly lower number of tertiary mammosphere compared to cells without treatment (a), (*p=0.05, **p<0.01). Mean of three independent experiments showed lower percentage of Aldefluor positive MCF7 and ZR75-1 after treating with trastuzumab (b), whereas trastuzumab does not have suppressive effect to Alfluour positive cells in SUM159 and MDMBA231 (c). To determine the effect of HER2 expressing cells in terms of tumor initiation, HER2 positive and negative MCF7 were sorted using flow cytometry and inoculate into mouse fat pad. Tumor volumes generated by 10,000 cells of HER2-positive are significantly higher compared with tumor from HER2-negative MCF7 (d). In addition to the established role of Aldefluor positive cells in tumor initiation, HER2 is another important factor in tumor formation in luminal breast cancer. The four populations of MCF7 (Aldefluor–/HER2–, Aldefluor–/HER2+, Aldefluor+/HER2– and Aldefluor+/HER2+) were sorted by flow cytometry, then inoculation 1,000 cells into mammary fat pad. HER2-positive MCF7 has significantly greater tumor forming ability compared with HER2-negative MCF7, regardless of Aldefluor status. Moreover, HER2 positivity is essential for tumor growth in population of Aldefluor negative MCF7 (e,f).
Figure 2:
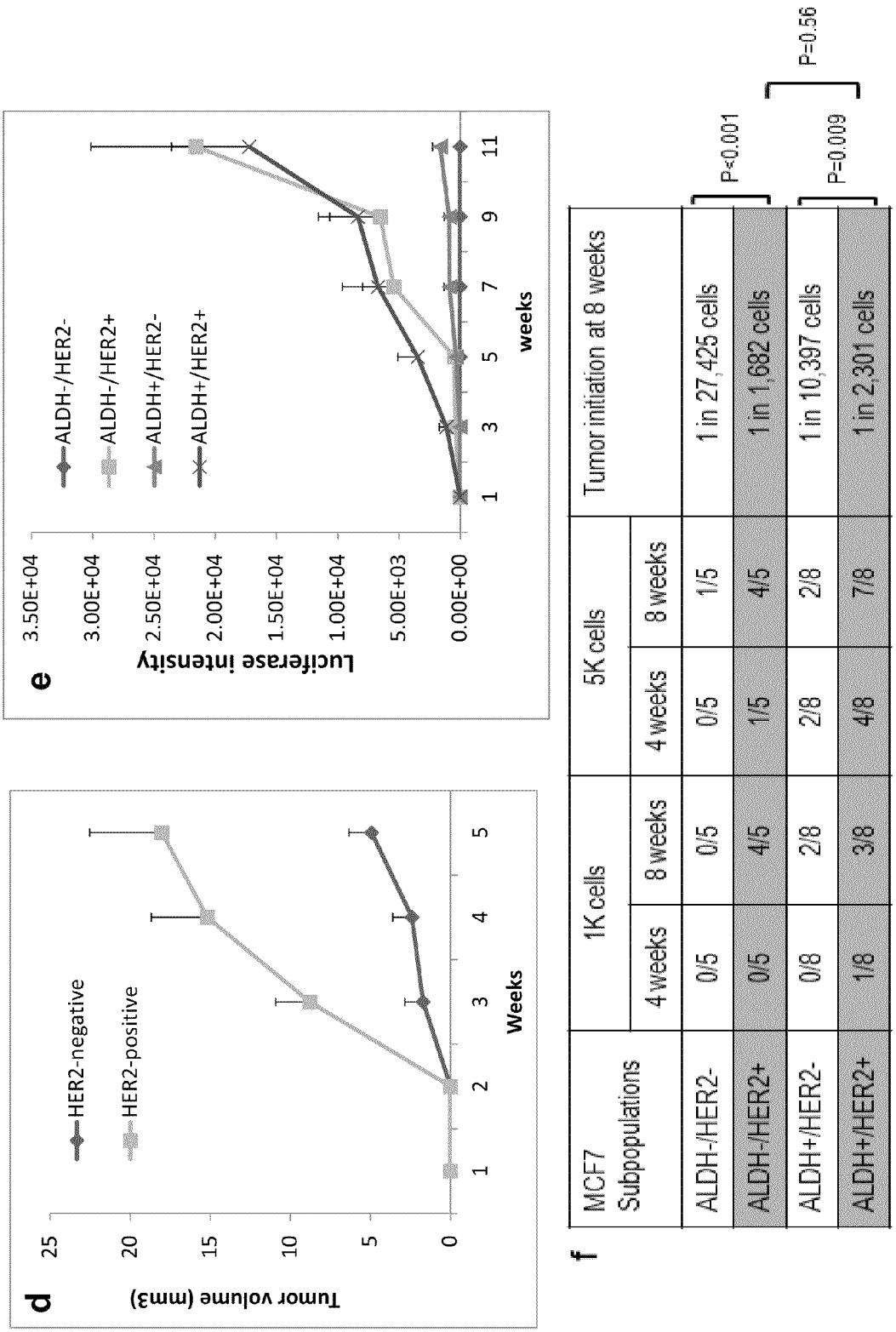
Figure 8:
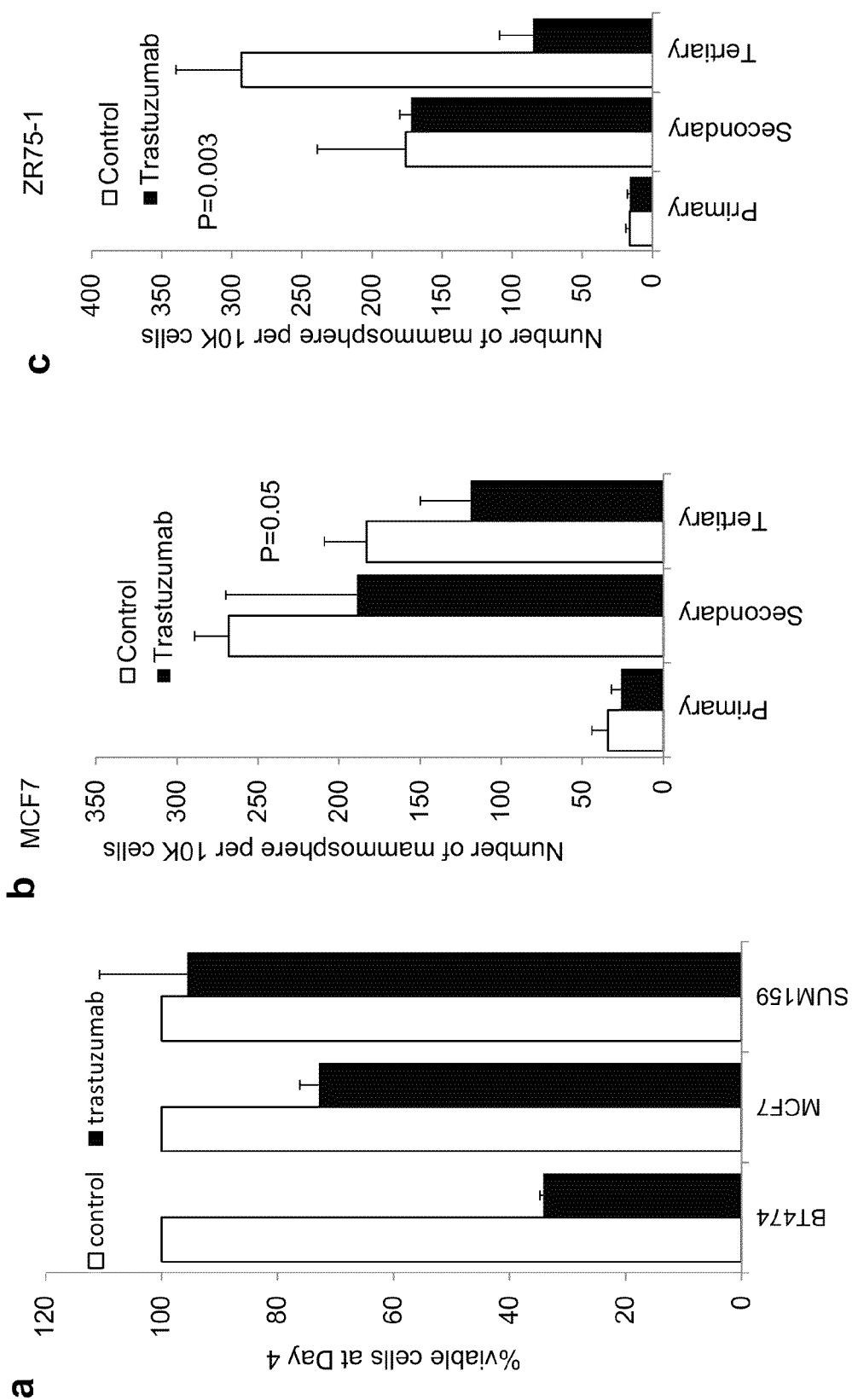
FIGS. 8a-c show (a) MTT analysis for tumor growth in 2-D culture. (b,c) Effects of trastuzumab in mammosphere formation from MCF7 and ZR75-1, respectively.
Figure 9:
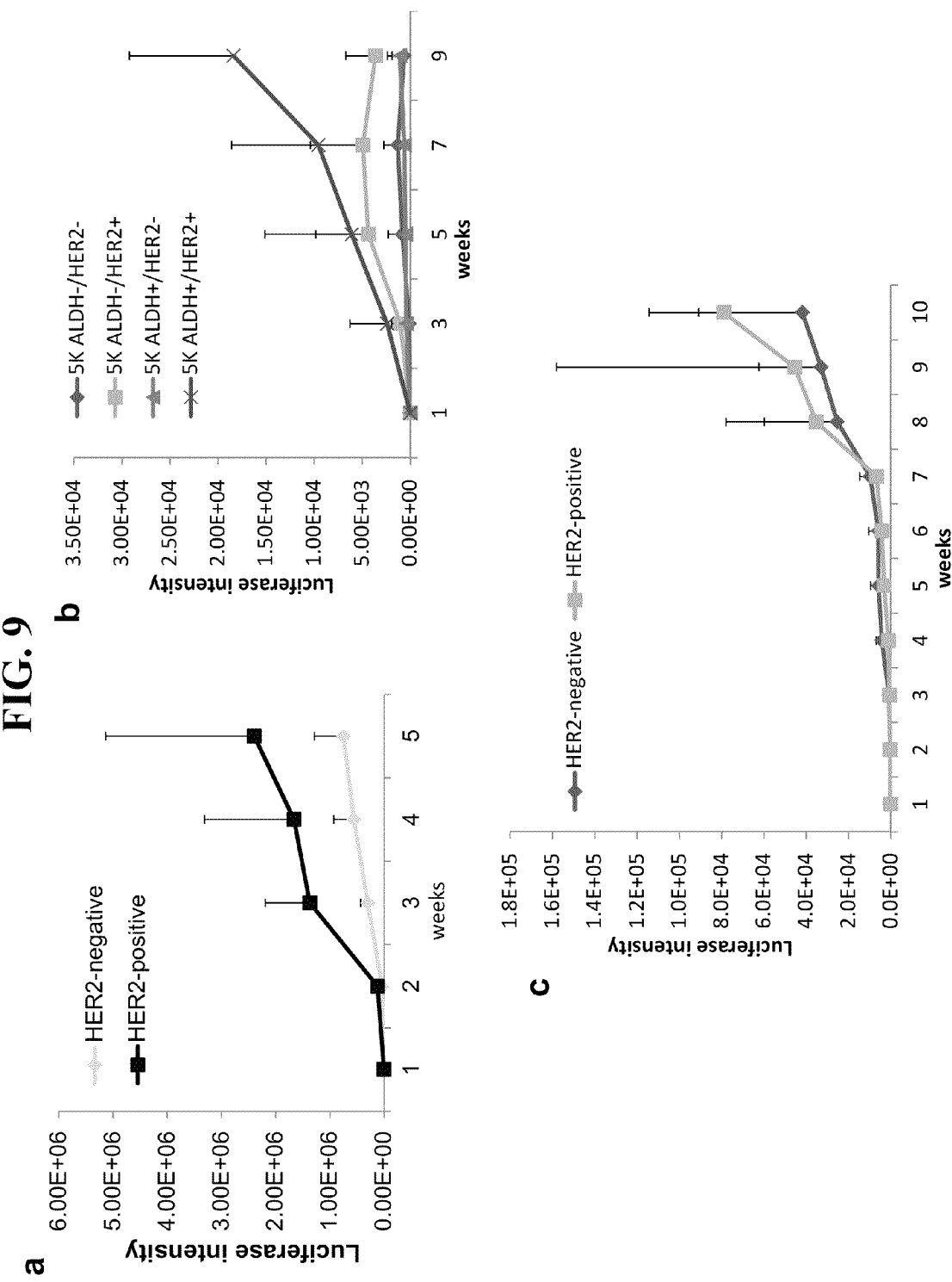
FIGS. 9a-c show (a) Luciferase intensity of sorted HER2-positive and negative MCF7 inoculation into fat pad. (b) MCF7 subpopulation according to ALDH and HER2 status of 5K cell into mouse fat pad.
Figure 10:
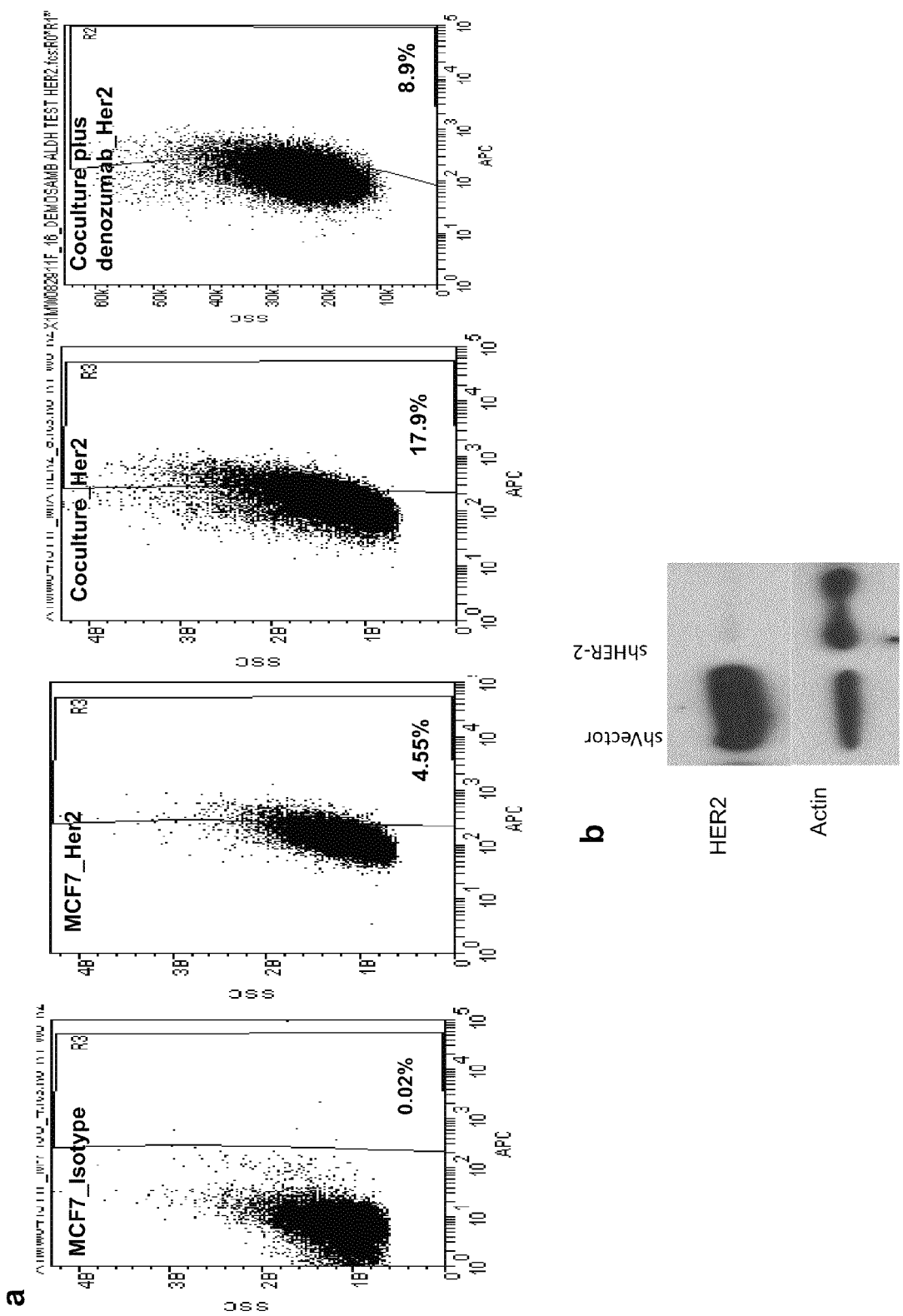
FIGS. 10a and 10b show (a) representative of flow cytometry data of increasing HER2 expression in MCF7 when coculture with osteocyte and denosumab can suppress this effect. Efficacy of siRNA to knock down HER2 in MCF7 is shown by western blot (b).

Trastuzumab (HERCEPTIN) Reduces the CSC Population of Luminal Breast Cancer Cells in vitro In order to determine the functional role of HER2, in vitro and in vivo assays were utilized. The effects of the HER2-blocking antibody trastuzumab were first assessed on cell growth in vitro. As previously reported, the effects of trastuzumab on inhibiting cell growth were limited to cells lines that displayed HER2 amplification (FIG. 8a) when these cells were cultured under standard conditions. Since CSCs represent a small component of the total cell population, growth in vitro is largely determined by the proliferative potential of the bulk tumor populations. In contrast to growth under attached conditions, CSCs are able to form mammospheres when grown in serum-free conditions on hydrophobic surfaces[22]. Formation of secondary and tertiary mammospheres upon serial passage has been utilized as an in vitro surrogate marker of CSCs[17]. In contrast to the absence of effects in standard culture conditions, trastuzumab significantly reduced tertiary mammosphere formation of MCF7 and ZR75-1 luminal mammary carcinoma cells but had no effect on mammosphere formation in basal/claudin low SUM159 cells (FIG. 2a). The effects of trastuzumab on the CSC population were further assessed utilizing the Aldefluor assay. Consistent with the mammosphere formation assays, trastuzumab significantly reduced the percent of Aldefluor-positive cells in luminal MCF7 and ZR25-1 cells but had no effect on the Aldefluor-positive populations in basal/claudin low SUM159 or MDA-MB231 cells (FIG. 2c).

HER2 Drives the Cancer Initiating Population in Luminal Breast Cancer Xenografts The previous in vitro studies suggested that HER2 plays an important role in the regulation of cancer stem cell populations. However, a more definitive test of cancer stem cell characteristics is the ability to initiate tumors in NOD/SCID mice. To determine the relationship between HER2 expression and tumor initiating capacity, luciferase-labeled MCF7 cells were sorted for HER2 expression and introduced into the fat pads of NOD/SCID mice. The median time to develop a palpable tumor following injection of 10K cells was significantly less in HER2 expressing than in HER2 non-expressing cells (p=0.05). Furthermore, the rate of tumor growth and resulting tumor size was significantly greater in HER2-positive compared to HER2-negative cells. HER2 expression was compared to that of Aldehehyde dehydrogenase (ALDH) to identify tumor initiating cell populations. Luciferase labeled MCF7 cells were sorted by flow cytometry into four subgroups based on expression of these markers (Aldefluor-negative, HER2-negative, Aldefluor-negative/HER2-negative, Aldefluor-negative/HER2-positive, Aldefluor-positive/HER2-negative and Aldefluor-positive/HER2-positive) and 5,000 cells from each group were injected into NOD/SCID mice. Tumor growth curves as assessed by luciferase emission are shown in FIG. 2E. The proportion of tumor initiating cells in each population was calculated based on the percentage of mice developing tumors at eight weeks as previously described. Tumor initiation, as well as growth rate, were significantly higher in HER2 expressing compared to HER2 non-expressing cells regardless of the cellular ALDH status. Within the ALDH-negative population HER2 overexpressing cells had greater than a 10-fold increase in tumor initiating capacity compared to HER2 non-expressing cells (p<0.001). Similarly, for the ALDH-positive populations, HER2 overexpressing cells were significantly enriched in HER2-positive compared to HER2-negative populations (p=0.009, FIG. 2g). These results support the in vitro studies suggesting that HER2 is expressed in the tumor initiating CSC population in luminal breast cancer cells.

Figure 3:
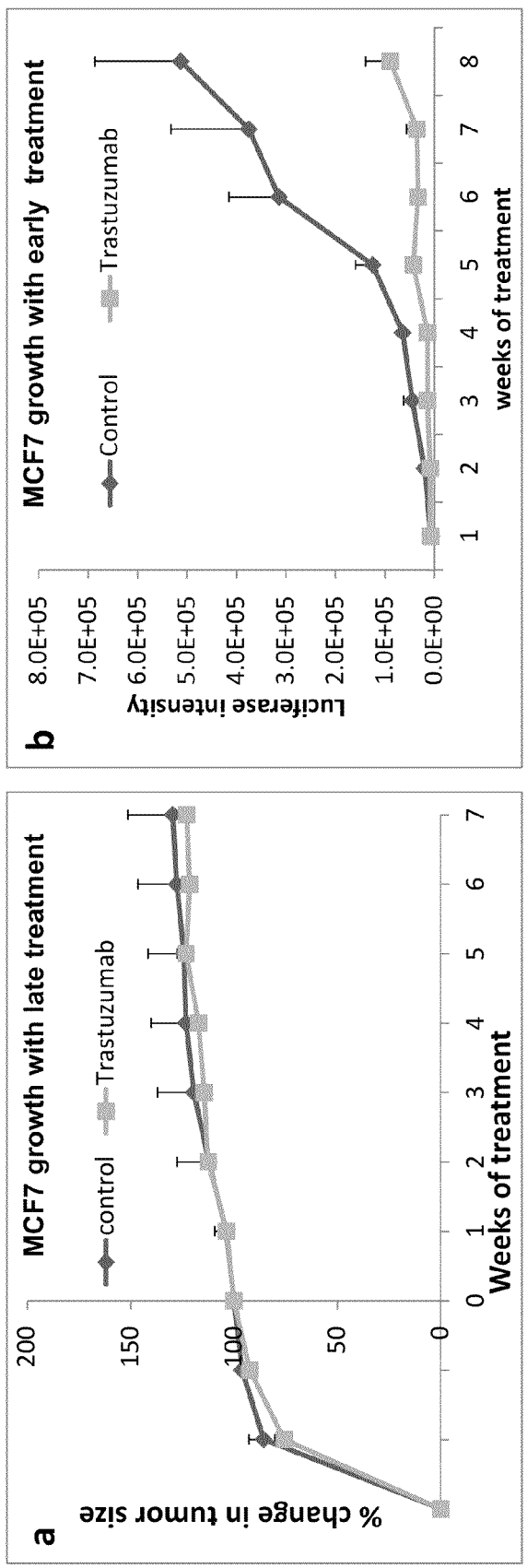
FIGS. 3a-g show the effects of trastuzumab on breast xenograft growth in late- and early-treatment. Trastuzumab has no suppressive effect to MCF7 tumor in mouse mammary fat pad (a). For late treatment, trastuzumab treatment was started at the time of established tumor (4 weeks after inoculation) and continued as 6-week treatment. In contrast, trastuzumab was able to suppress MCF7 tumor growth in mouse mammary fat pad if administered at the time of inoculation (b). Effects of trastuzumab and docetaxel in early-versus late-treatment setting in BT474 and ZR75-1 xenograft are shown in FIG. 3c-g. Docetaxel with or without trastuzumab had highest efficacy to shrink tumors in late-treatment setting in BT474 (c) and ZR75-1(e). In late-treatment setting, trastuzumab alone provided some tumor suppression in BT474, but not ZR75-1(c, e). Early treatment of docetaxel suppressed tumor formation in both BT474 and ZR75-1 (d,f). Interestingly, adding trastuzumab to docetaxel as early treatment was able to delay tumor formation of ZR75-1 tumor compared with docetaxel alone (g).
Figure 3:
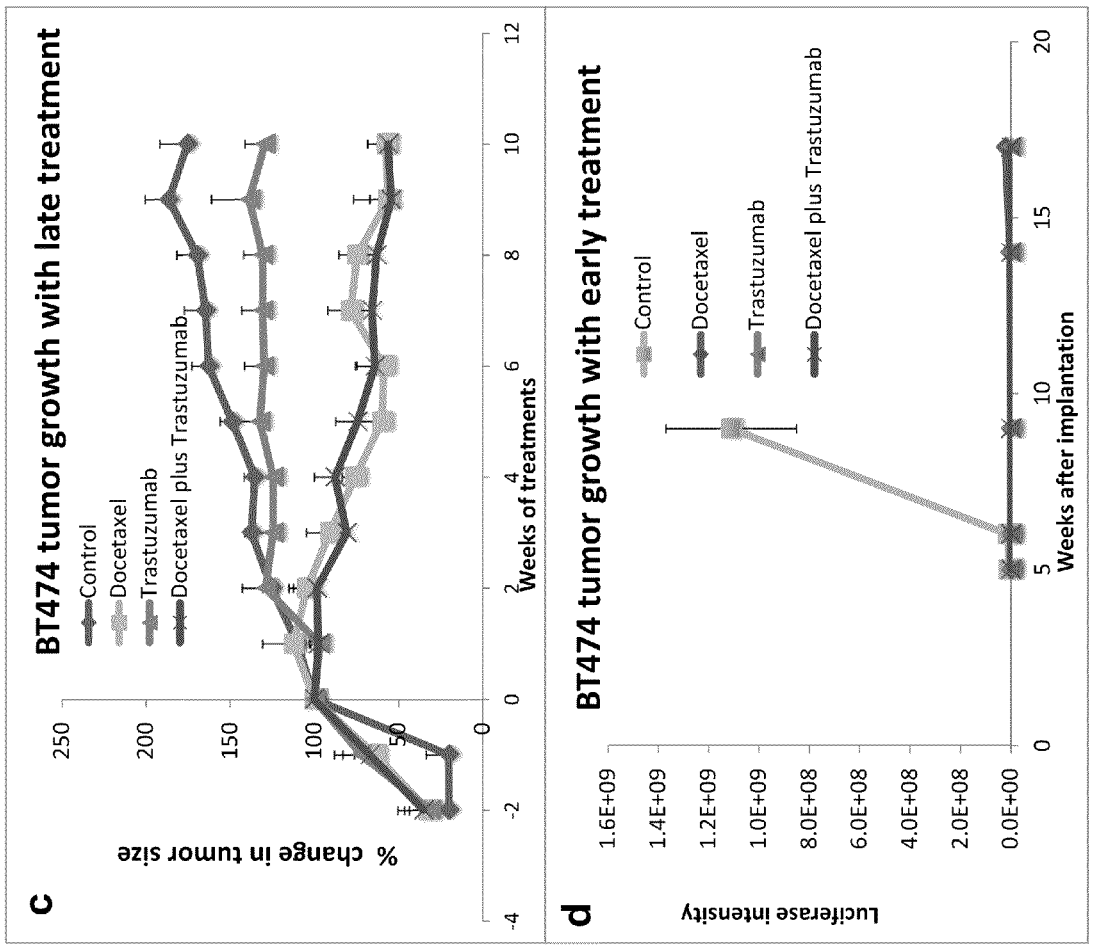
Figure 3:
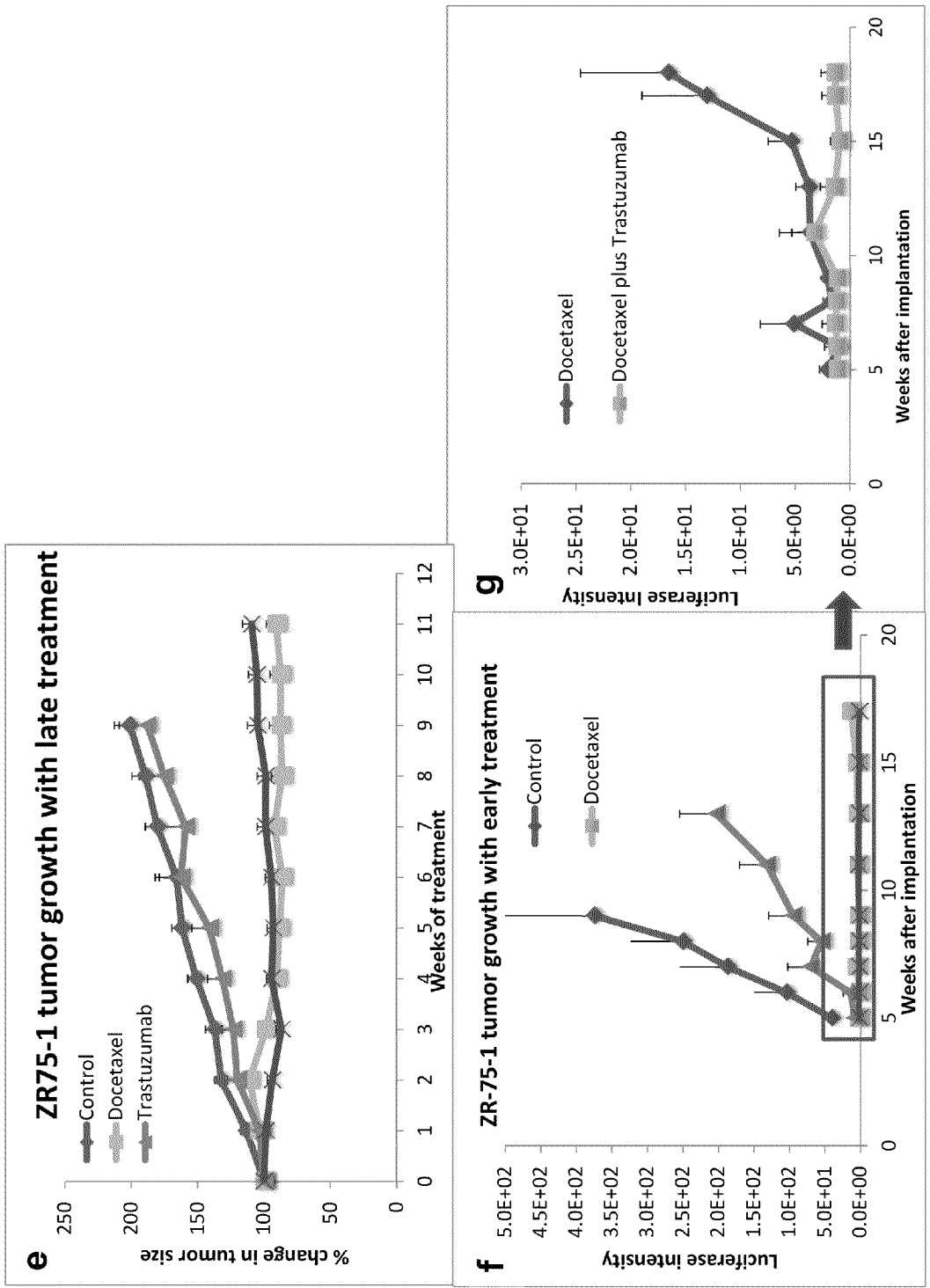

Effects of Trastuzumab on Growth of Luminal Breast Cancer Xenografts Generally Depends on the Timing of Administration The HER2 blocking antibody trastuzumab was utilized to determine the functional role of HER2 expression on tumor growth in mouse xenografts. Cancer stem cell models predict that in advance cancers, stem cell targeting agents would have little effect on tumor shrinkage since these cells constitute only a small fraction of the total cell population. In contrast, growth of tumors from microscopic disease at primary or metastatic to sites depends on cancer stem cells which have uniquely high self-renewal capacity compared to bulk tumor populations (21, 23). This Example therefore compared the effects of trastuzumab administered immediately after tumor inoculation (early disease) to administration after establishment of measurable tumors (late treatment). As shown in FIG. 3a, trastuzumab had little effect on the growth of established MCF7 xenografts. In contrast, administration of trastuzumab starting immediately after injection of MCF7 cells into the mammary fat pad significantly blocked tumor growth compared to control animals (FIG. 3b).

The standard treatment for women with HER2 amplified breast cancers is the combination of trastuzumab with cytotoxic chemotherapy. In order to simulate the use of this regimen in the early (adjuvant) versus advanced disease setting, this Example determined the effect of trastuzumab, the cytotoxic chemotherapy docetaxel, or both on the growth of HER2 amplified BT474 or luminal ZR75-1 tumor xenografts. These therapies were administered immediately after tumor injection (early disease) or after the establishment of palpable tumors (late disease). As shown in FIGS. 3c and 3d, administration of trastuzumab had a significant effect on reducing the growth of established HER2 amplified BT474 tumors, whereas it had no significant effect on the growth of the luminal ZR75-1 cells which do not have HER2 amplification. In contrast, the cytotoxic chemotherapy docetaxel reduced tumor growth of both xenografts. Whereas the effects of trastuzumab on tumor growth in the advanced settings were limited to HER2 amplified BT474 cells, when administered in the early (adjuvant) setting trastuzumab significantly reduced growth of luminal ZR75-1 which do not display HER2 amplification cells as well as HER2 amplified BT474 cells (FIG. 3d, 3f). Administration of trastuzumab plus docetaxel in the early setting completely eliminated tumor growth (FIG. 3g). Together, these experiments demonstrate that in HER2 amplified cells trastuzumab has a significant effect on tumor growth when administered in either the advanced or early settings. In contrast in HER2 non-amplified luminal tumors, trastuzumab's effects are seen only when it is administered in the early (adjuvant) setting.

HER2 and ALDH are Co-Expressed in Human Luminal Breast Cancers and are Preferentially Located at the Tumor Invasive Front Immunohistochemistry was utilized, as well as AQUA® analysis, to provide qualitative and quantitative information on the relationship of HER2 and ALDH expression in primary and metastatic breast cancers. As was the case in breast cancer cell lines, primary and metastatic breast cancers showed a significant association between expression of HER2 and ALDH at the individual cell level. Furthermore, in tumors without HER2 amplification, HER2-positive/ALDH-positive tumor cells were preferentially found at the tumor invasive front at tumor stromal interfaces.

The Bone Microenvironment Induces the HER2 Expression in Luminal Tumor Cells

Figure 4:
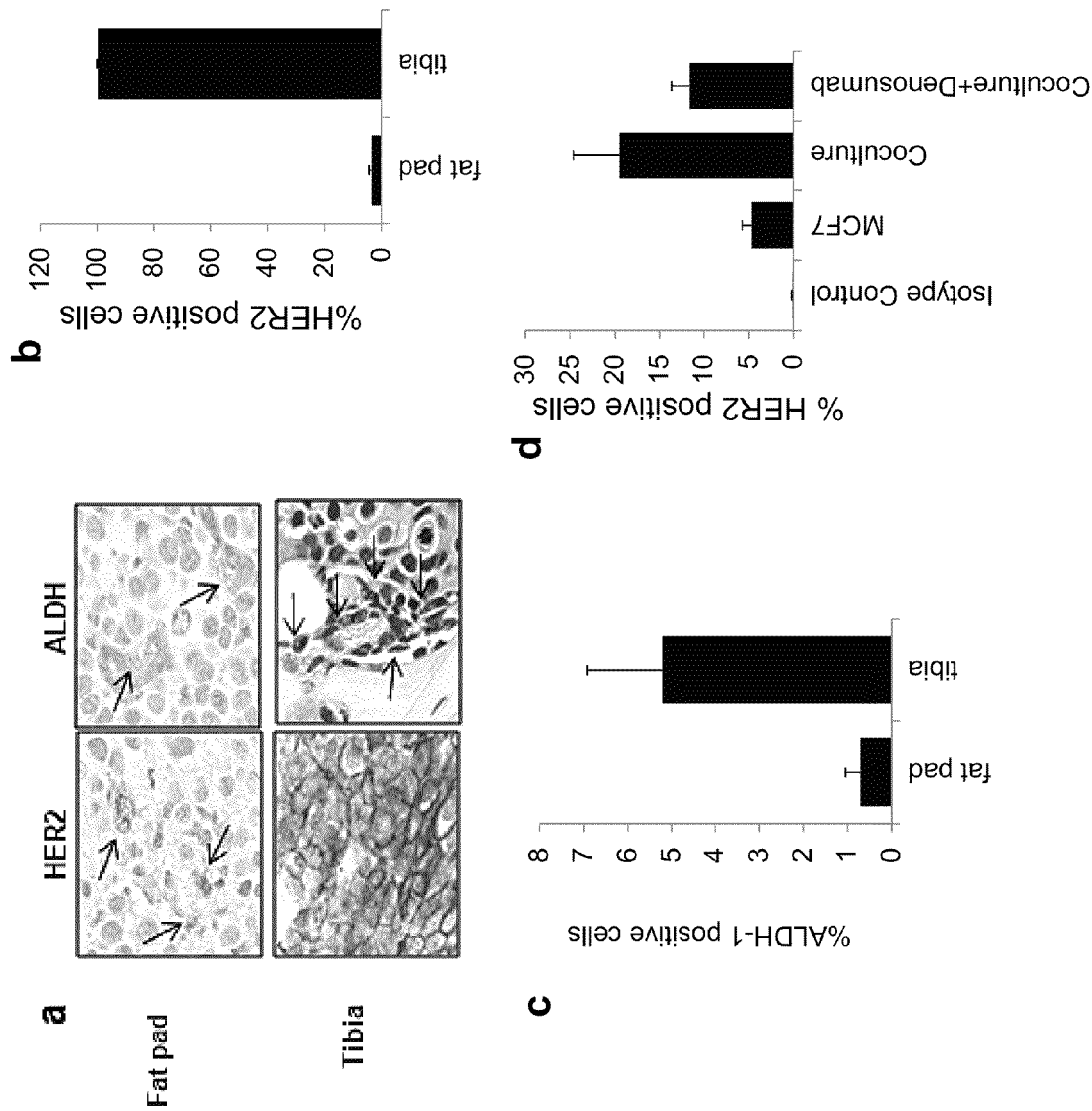
FIGS. 4a-k show bone microenvironment increase HER2 expression along with increasing cells with ALDH1. HER2 expression and percentage of cells with positive ALDH1, assessed by immunohistochemistry, was significantly increased in tumor generated by MCF7 in bone compared to mammary fat pad inoculation (a,b,c). Coculture of MCF7 with human osteocyte, simulating bone microenvironment in vitro, induced significantly higher HER2 expression (d). Denosumab, a RANK ligand inhibitor, was able to suppress effect of increase HER2 in bone microenvironment. HER2 positivity plays an important role in tumor-initiating capacity in bone. The functional role of HER2 was determined using HER2 knockdown MCF7 cells inoculation into tibia. The efficacy of HER2 knockdown by western blot is shown (SEE FIG. 10b). Knockdown of HER2 reduced ability to form tumor in bone compared with MCF7 shVector (e). In addition, small tumors grew from MCF7 shHER2 had lower percentage of ALDH1-positive cells (f). Trastuzumab effectively inhibits MCF7 tumor growth in bone and fat pad when use as early-treatment setting. MCF7 tumor in bone was almost completely blocked with early trastuzumab treatment at the time of inoculation (h). In contrast, trastuzumab was not able to suppress tumor in bone (g) when treatment was started at the time of established tumor (arrow). (i) represents picture of immunohistochemistry of HER2 and ALDH1 in tibia tumor with and without trastuzumab treatment. Tumor area (j) and percentage of ALDH-positive cells (k) decreased in group with early-treated trastuzumab.
Figure 4:
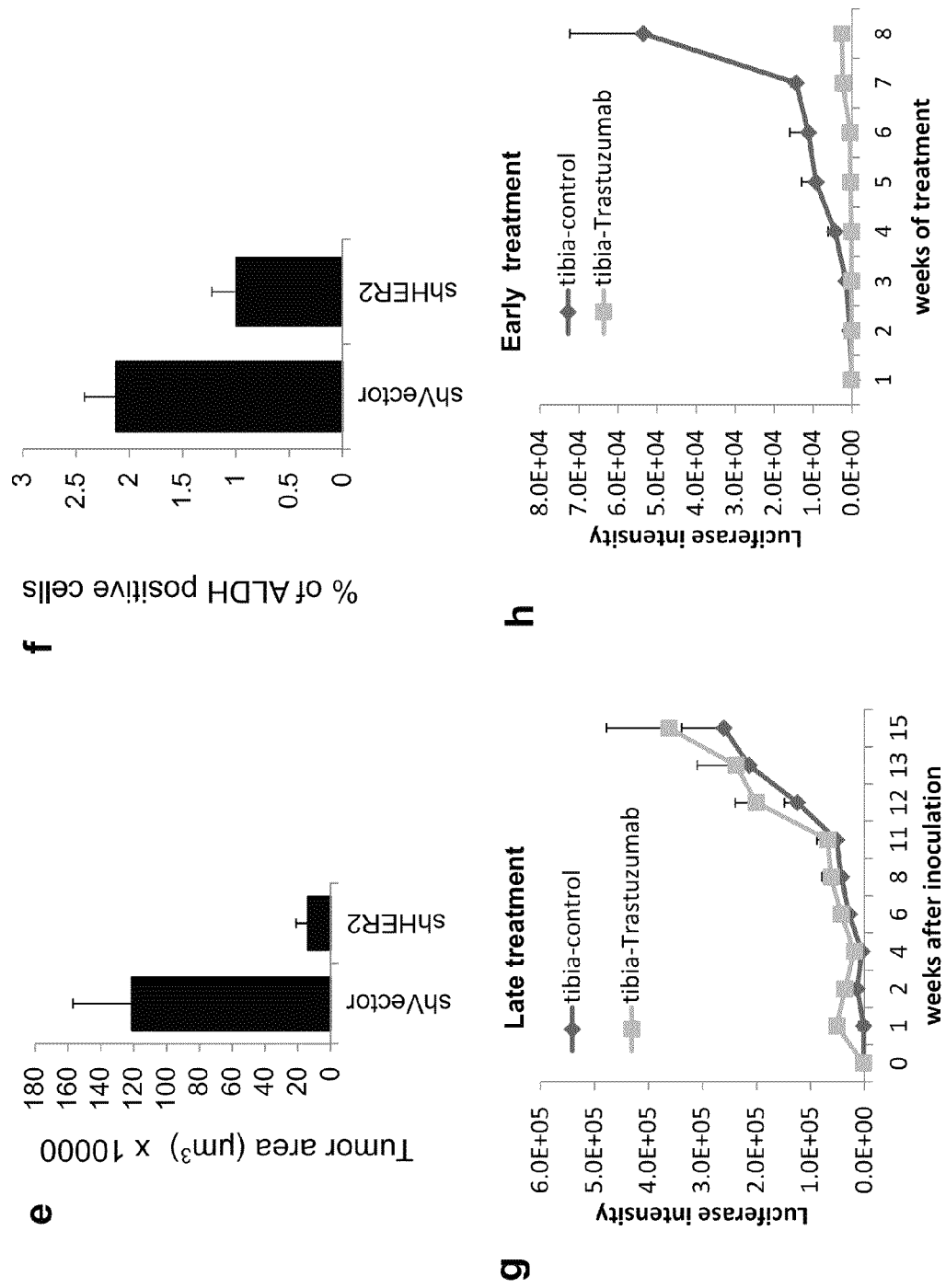
Figure 4:
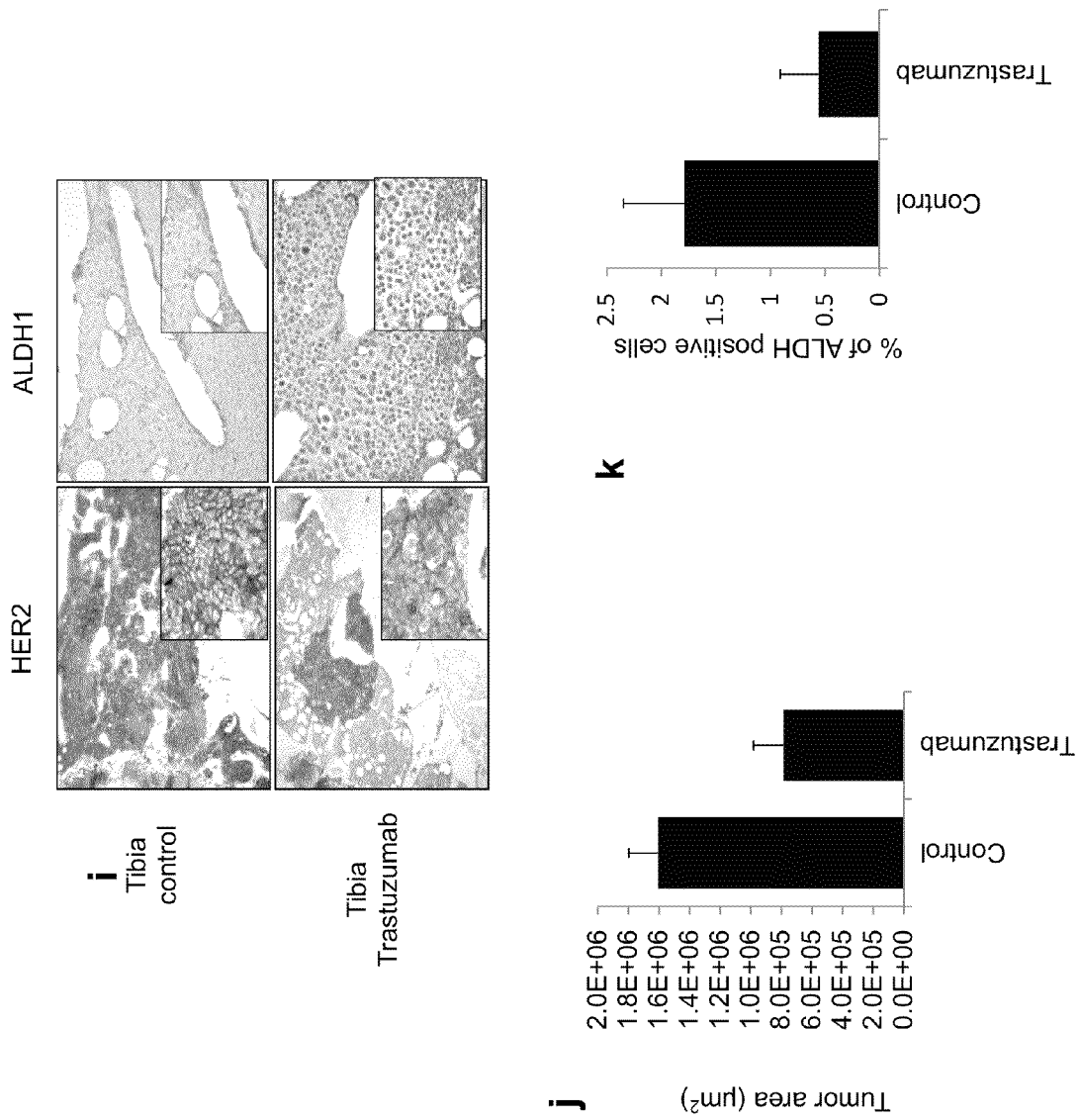

Bone represents the most frequent site for metastasis of human breast cancer and luminal breast cancers are the most frequent subtype that metastasizes to bone[23]. Although a number of factors have been postulated to play a role in facilitating the metastasis and growth of breast cancers in the bone microenvironment, the role of HER2 in this setting is poorly understood. In order to determine the role of HER2 in breast cancer bone metastasis this Example utilized a model in which luciferase-labeled MCF7 breast cancer cells were directly injected into a mouse tibia and tumor growth assessed by light emission. Whereas the growth of MCF7 cells in the mouse mammary fat pad required estrogen supplementation for tumor growth, MCF7 cells introduced directly into the tibia grew in an estrogen-independent manner and, in fact, were inhibited by estrogen pellet supplementation. As assessed by immunochemistry, HER2 expression was significantly increased in MCF7 cells grown within the bone microenvironment compared to the same cells grown in the mammary fat pad (FIG. 4a, 4b). Furthermore, as assessed by fluorescence in situ hybridization FISH, this increased expression was not due to gene amplification. This increase in HER2 expression was accompanied by an increase in the percent of cells expressing the stem cell marker ALDH1 (FIG. 4a, c).

To simulate the bone microenvironment in vitro, co-culture experiments were performed utilizing MCF7, DsRed labeled with osteocytes generated from human bone mesenchymal stem cells. Co-culture of MCF7 cells with human osteocytes resulted in greater than 3-fold induction of HER2 expression in the MCF7 cells (FIG. 4d). A number of biological effects of the bone microenvironment and mediated by RANK-ligand. The RANK-L inhibitor, denosumab partially blocked HER2 induction by osteocyte co-cultures. Together, these results suggest that RANK-L present in the bone microenvironment is able to induce HER2 expression in luminal breast cancers.

HER2 Drives the CSC Population and is Necessary for Maintaining Tumor Growth in the Bone Microenvironment To provide direct functional evidence for a role in HER2 in bone growth, the effects of HER2 knockdown were determined on the capacity of MCF7 cells to initiate bone tumor growth. The efficacy of HER2 knockdown via a siRNA lentivirus was demonstrated by Western blotting (FIG. 4b). Knockdown of HER2 in MCF7 cells significantly reduced their ability to form tumors in bone as assessed by tumor area (FIG. 4e). In addition to significantly reducing HER2 expression and tumor growth, the small tumors that grew expressed significantly lower levels of ALDH-1 than control tumors (FIG. 4f). It was next determined the effects of systematically administered trastuzumab on tumor growth in the tibia model. As was the case in the mammary fat pad, the effects of trastuzumab on MCF7 growth in mouse tibias was dependent on the time of administration. When trastuzumab administration was initiated immediately after tumor inoculation (early) tumor growth, tumor growth was almost completely blocked. In contrast, trastuzumab had little effect on the growth of established (late) tumors (FIGS. 4g, 4h and 4j). Trastuzumab treatment also reduced the percent of ALDH-1 expressing cells (FIGS. 4i and 4k).

HER2 Expression is Increased in Bone Metastasis Compared to Primary Tumors in Matched Patient Samples To demonstrate the clinical relevance of the mouse models, the expression of HER2 was determined in a series of breast cancer patients in which the primary tumor and a matched bone metastasis were obtained. Importantly, in tumors that were classified as "HER2-negative" by classical criteria in the primary tumor, HER2 was significantly higher in bone metastasis compared to the primary tumor. Furthermore, the increased expression of HER2 in the bone marrow metastasis was not due to gene amplification as demonstrated by FISH analysis. Thus, as was the case in mouse models, bone metastasis of luminal breast cancers is associated with increased expression of HER2.

EXAMPLE 2

Resistance to HER2 targeting mediated by IL6 Inflammatory Loop

HER2-targeting antibody (e.g., trastuzumab) resistant cells were developed during development of embodiments of the present invention by knocking down PTEN expression in HER2 overexpressing breast cancer cell lines. Experiments were conducted during using such cells that demonstrated that development of trastuzumab resistance in these cells is mediated by activation of an IL6 inflammatory feedback loop leading to expansion of the cancer stem cell (CSC) population. Long term trastuzumab treatment generates highly enriched CSCs which display an EMT phenotype secreting over 100-fold more IL6 than parental cells. An IL6 receptor antibody interrupted this inflammatory feedback loop reducing the cancer stem cell population resulting in decreased tumor growth and metastasis in mouse xenographs. These results indicate that trastuzumab resistance is mediated by an IL6 inflammatory loop, and indicate that blocking this loop provides alternative strategy to overcome trastuzumab resistance.

Experimental Procedures

Cell Lines and Reagents

MCF7, BT474, SKBR3, and HCC1954 cell lines were maintained by ATCC guidelines. The SUM159 cell line was maintained in Ham's F12 medium supplemented (with 5% fetal bovine serum, 5 mg/ml insulin, 1 mg/ml hydrocortisone and antibiotic/antimycotic 10,000 U/ml penicillin G sodium, 10,000 mg/ml streptomycin sulfate, and 25 mg/ml amphotericin B). Perifosine, Akt inhibitor was obtained from Keryx Biopharmaceuticals Inc., and docetaxel (Taxotere) was from Sanofi Aventis (Bridgewater, N.J.). Anti-IL6R antibody (Tocilizumab) was obtained from Chugai Pharmaceuticals Co. Ltd. (Shizuoka, Japan). Trastuzumab was purchased from the University of Michigan Cancer Center Pharmacy. NF-kB inhibitor, Bay11-7082, and Stat3 Inhibitor VII were purchased from EMD Chemicals (Gibbstown, N.J.).

The PTEN antibody was purchased from Cell Signaling Technology Inc., the α-Tubulin antibody was from Santa Cruz Biotechnology Inc., and the phospho-NF-kB (p65) antibody was from Cell Applications. Fluorescent-conjugated antibodies to CD44, CD24, CD49f, and EpCAM are from BD Biosciences (San Jose, Calif.).

Cytokine Antibody Array and ELISA

Equal numbers of cells were plated and cultured for 3 days. Subsequently, conditioned media from these cell cultures were collected and analyzed by the RayBio Human Cytokine Antibody Array 5 (RayBiotech, Inc. Norcross, Ga.).

ELISA assay was performed using the conditioned medium collected from two day cultures of cells seeded at 200,000 cells/plate. Blood samples were drawn through orbital vein just before sacrificing the mice. Plasma separated from whole blood by centrifugation at 14,000 rpm at 4° C. Plasma from tumor bearing mice and the conditioned medium from in vitro cultures were then analyzed for the indicated cytokines by UM Cytokine Core facility.

Tumorsphere Assay

Single cells were plated on ultra-low attachment plates at a density of $1\times10^5$/ml and grown for 7 days in a mammocult medium (Stem Cell Technologies). After the treatment of primary spheres, they were dissociated into single-cell suspension and plated at a density of $5\times10^3$-$1\times10^4$/ml for the subsequent passages. Secondary spheres were counted after 5-7 days in culture.

Lentiviral Constructs and Infection of NMECs and Breast Cancer Cell Lines

The construction of lentiviral shRNA, pLL3.7-shPTEN targeting the human PTEN gene and pLenti-RSV-HER2 overexpressing HER2 gene were previously described (Korkaya et al., 2008; Korkaya et al., 2009; herein incorporated by reference in their entireties). Using both pLL3.7-shPTEN and pLenti-RSV-HER2, cell lines were coinfected with SUM159 and MCF7 to generate MCF7–HER2$^+$PTEN$^-$ and Sum159–HER2$^+$PTEN$^-$ cells. Stable clones of MCF7HER2$^+$, Sum159$^-$HER2$^+$, MCF7$^-$PTEN-, and Sum159$^-$PTEN$^-$ cells were previously generated (Korkaya et al., 2008; Korkaya et al., 2009; herein incorporated by reference in their entireties).

Aldefluor Assay and Flow Cytometry

To measure ALDH activity, the Aldefluor assay was carried out according to manufacturer's guidelines (StemCell Technologies, Inc., Durham, N.C.). Indicated cells were incubated with fluorophore-conjugated CD44 or CD24 antibodies alone or in combination on ice for 30 min, washed with Hank's balanced salt solution (HBSS), and resuspended in DAPI containing HBSS buffer for flow cytometry analyses.

Implantation of Cells in NOD/SCID Mice and Drug Treatments

In mouse xenografts, luciferase-expressing breast cancer cell lines we utilized for in vivo bioluminescence imaging using the Caliper IVIS imaging systems. Breast cancer cells expressing the luciferase gene were implanted into the fat pads of 5-week-old NOD/SCID mice. These mice were imaged the following day to ensure the implantation of tumor cells.

Early drug treatments were started right after the implantation of cells in mice; trastuzumab was given at 20 mg/kg dose i.p. once per week, docetaxel was given at 10 mg/kg dose i.p. once per week, anti-IL6R antibody was given at 10 mg/kg once a week, and perifosine was given at 20 mg/kg twice per week. Treatments for all early settings were 8 weeks long. Late treatments were started after the establishment of primary tumors (roughly when they reached 0.4 cm in size). Drug doses were as described in early setting.

All mice were housed in the AAALAC (Association for Assessment and Accreditation of Laboratory Animal Care International)-accredited specific pathogen-free rodent facilities at the University of Michigan. Mice were housed on sterilized, ventilated racks and supplied with commercial chow and sterile water, both previously autoclaved. All experimentations involving live mice were conducted in accordance with standard operating procedures approved by the University Committee on the Use and Care of Animals at the University of Michigan.

Results

PTEN Downregulation in HER2-Overexpressing Breast Cancer Cells Increases the Proportion of Invasive CSCs PTEN inactivation frequently occurs in the context of HER2 amplification, a phenotype associated with trastuzumab resistance. The effect of PTEN knockdown on CSC-like populations in HER2 overexpressing breast cancer cell lines was examined in experiments conducted during development of embodiments of the present invention. The efficiency of HER2 overexpression and PTEN knockdown utilizing lentiviral shRNAs or control vector is demonstrated (SEE FIGS. 11A and 11F). First, the effect of these molecular alterations on CSCs were assessed by tumorsphere assay, which was shown to enrich for CSCs (Singh et al., 2003; herein incorporated by reference in its entirety). PTEN deletion and HER2 overexpression resulted in a significant increase in tumorsphere formation (SEE FIGS. 11B and 11G). PTEN knockdown in HER2-overexpressing cells resulted in a 2- to 3-fold increase in sphere formation and a 6-fold increase over the parental cells. To confirm and extend these observations, the effect of PTEN knockdown and HER2 overexpression on the CSC markers, such as the expression of aldehyde dehydrogenase (ALDH) or the CD44+/CD24− phenotype (Al-Hajj et al., 2003; Ginestier et al., 2007; herein incorporated by reference in their entireties), was examined There was a stepwise increase in the Aldefluor-positive and CD44+/CD24− populations in parental MCF7–DsRed, MCF7−PTEN−, MCF7− HER2+, and MCF7−HER2+PTEN− cells, respectively, when they were analyzed by the Aldefluor assay or CD44+/CD24− expression (SEE FIGS. 11C and 11E). SUM159 cells are composed of over 90% CD44+/CD24− cells, precluding the use of these markers to identify CSC in this cell line. However, there was a 2-fold increase in the Aldefluor-positive population in SUM159−HER2+PTEN− cells as compared to SUM159−HER2+ cells (SEE FIG. 11H). Together, these results demonstrate that the increase in the CSC population induced by HER2 overexpression is further enhanced by PTEN deletion.

Figure 11:
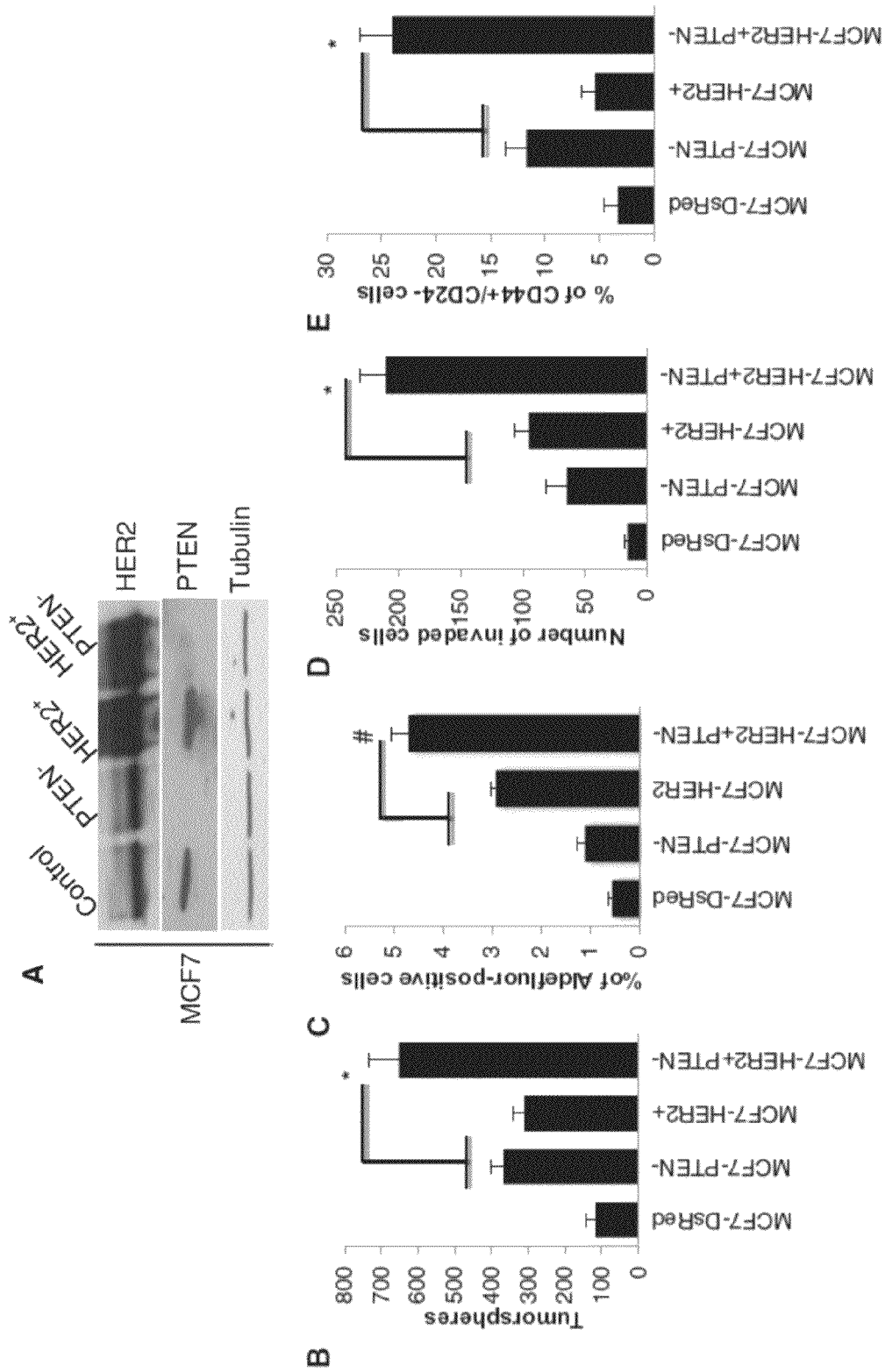
FIGS. 11A-G show Western blots and graph demonstrating that PTEN downregulation and HER2 overexpression snergize to increase the CSC population in vitro. (A-G) Downregulation of PTEN and/or overexpression of HER2 in MCF7 or Sum159 cells is demonstrated by western blotting in (A) and (F). PTEN downregulation in HER2-overexpressing cells increased the tumorsphere formation (B and G), Aldefluor-positive cell populations (C and H), as well as invasion compared to either HER2 overexpression or PTEN downregulation in vitro (D and I). MCF7–HER2$^+$PTEN$^-$ cells showed a significant increase in the proportion of CD44$^+$/CD24$^-$ cells as compared to the MCF7–HER2+ or MCF7–PTEN$^-$ cells (E).
Figure 11:
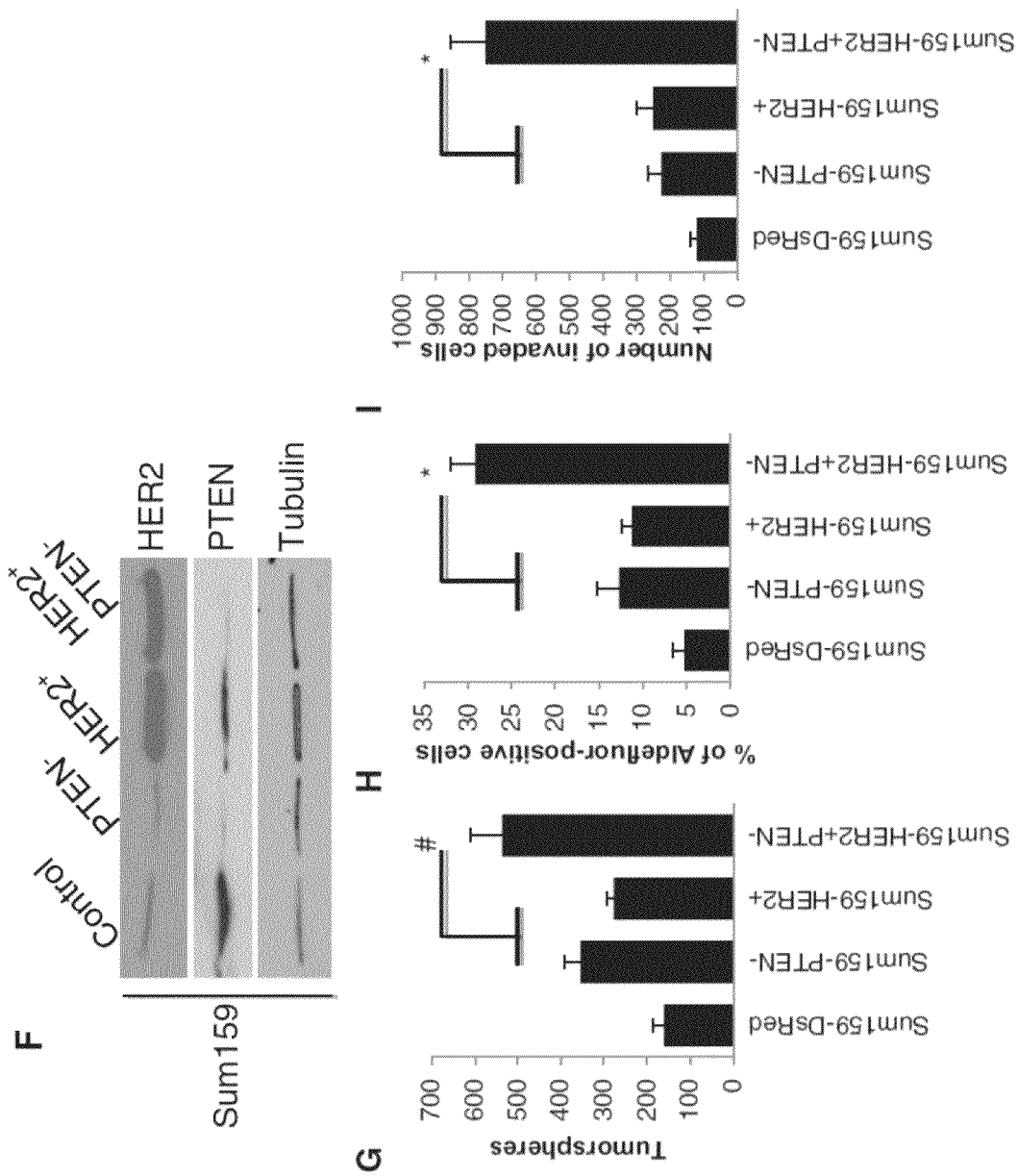

The effect of HER2 overexpression and PTEN deletion on invasion of tumor cells through matrigel was assessed. As shown in FIGS. 11D and 11I, PTEN deletion in HER2-overexpressing MCF7 or SUM159 cells enhanced in vitro invasive capacity, as compared to cells with either HER2 overexpression or PTEN deletion alone.

PTEN Downregulation Generates a Trastuzumab-Resistant CSC Population

The effect of the HER2 blockade was determined using the HER2-targeting antibody trastuzumab on CSC populations as assessed by tumorsphere formation or by ALDH expression. Primary tumorspheres for each indicated cell line were treated with trastuzumab during the course of 5-7 days, and the effects of this treatment on the ability to form secondary tumorspheres was assessed. There was no significant effect of trastuzumab on tumorsphere formation in parental cells. However, HER2 overexpression rendered the tumorsphere-forming population sensitive to trastuzumab as reflected by a 50% reduction in tumorsphere formation in MCF7–HER2+ and SUM159–HER2+ cells upon trastuzumab treatment. In contrast, trastuzumab had no significant effect on secondary tumorsphere formation in MCF7–HER2+PTEN− and SUM159–HER2+PTEN− cells (SEE FIGS. 12A and 12D). In addition, trastuzumab reduced the Aldefluor-positive population by 75% and 50% in MCF7–HER2+ and SUM159HER2+ cells, respectively (SEE FIGS. 12B and 12E). In contrast, there was a non-significant change in the Aldefluor-positive population in both MCF7–HER+PTEN− and SUM159–HER2+PTEN− cells (SEE FIGS. 12B and 12E) upon trastuzumab treatment.

PTEN Downregulation in HER2-Overexpressing Cells Generates Trastuzumab-Resistant Metastatic Tumors in NOD/SCID Mice Experiments were conducted during development of embodiments of the present invention to examine the biological consequences of increased CSC populations generated by HER2 overexpression and PTEN knockdown by implanting these cells into the mammary fat pads of NOD/SCID mice. Although parental MCF7 and SUM159 xenografts were able to grow in the mammary fat pads of these mice, they failed to generate metastasis in distant organs. In contrast, MCFTHER2+PTEN− and SUM159−HER2+PTEN− cells generated larger, primary tumors that extensively metastasized to lymph nodes, liver, and lung when compared to MCFTHER2+ and SUM159−HER2+ cells, which displayed only occasional metastasis to lung and liver (SEE FIGS. 12C and 12F). Furthermore, while MCF7−HER2+ xenografts in mice were responsive to trastuzumab treatment leading to reduced tumor size (SEE FIG. 12H), MCFTHER2+PTEN− xenografts demonstrated de novo resistance to trastuzumab (SEE FIG. 12H). The effects of trastuzumab on tumor weight were paralleled by effects on the CSC populations as assessed by the Aldefluor assay. The percentage of Aldefluor-positive tumor cells was reduced by over 50% by trastuzumab treatment in MCFTHER2+ cells (SEE FIG. 12I). In contrast, trastuzumab actually caused a slight increase in the Aldefluor-positive populations in MCFTHER2+PTEN− cells, demonstrating that PTEN deletion in HER2-overexpressing breast cancer cells generates a trastuzumab-resistant CSC population (SEE FIG. 12I).

PTEN Downregulation and HER2 Overexpression Synergize to Increase Expression of the Cytokines IL6, IL8, and CCL5/RANTES A number of cytokines, including IL6, IL8, and CCL5/RANTES, play a role in CSC regulation as well as in invasion and metastasis (Korkaya et al., 2011; herein incorporated by reference in its entirety). An antibody cytokine array was utilized in experiments conducted during development of embodiments of the present invention to determine the effects of HER2 overexpression, PTEN deletion, or the combination on levels of cytokine expression in MCF7 cells. A stepwise increase in IL6, IL8, and CCL5, as well as platelet-derived growth factor B (PDGF-B) secreted from MCF7−DsRed, MCFTHER2+, MCF7−PTEN−, and MCF7− HER2+PTEN− cells was detected (SEE FIG. 13A). As assessed by densitometry of the cytokine blots and utilizing an ELISA, secretion of these cytokines was increased by 2- to 3-fold in MCFTHER2+ or MCF7−PTEN− cells, compared to parental cells, and by 10- to 20-fold in MCFTHER2+PTEN− cells, compared to parental MCF7−DsRed cells (SEE FIGS. 13B and 13C). This dramatic elevation of cytokines in the MCFTHER2+PTEN− cells suggests a synergistic effect resulting from PTEN deletion and HER2 overexpression. Although parental MCF7−DsRed cells secreted detectable levels of IL8, CCL5, and PDGF-B, which were increased in MCF7−HER2+, MCF7−PTEN−, and MCFTHER2+PTEN− cells, there was no detectable expression of IL6 in parental MCF7 cells. To confirm that PTEN deletion increased cytokine production in HER2-overexpressing cells, PTEN knockdown in BT474, SKBR3, and HCC1954 cells was performed, all of which display endogenous HER2 gene amplification as well as in SUM159−HER2+ cells. The efficiency of PTEN knockdown in these cells is demonstrated by western blotting (FIG. 3D). The PTEN knockdown in these HER2-amplified cell lines and in SUM159−HER2+PTEN− cells increased IL6 production (SEE FIG. 13E).

Figure 13:
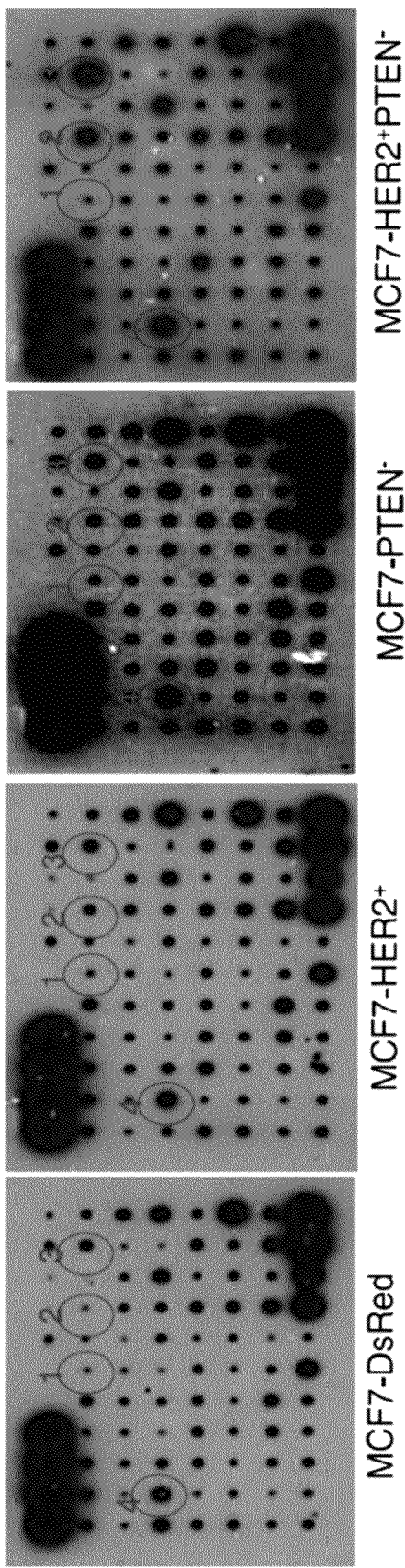
FIGS. 13A-J shows arrays and graphs demonstrating that PTEN downregulation in HER2-overexpressing cells activates an IL6/NF-kB-mediated inflammatory feedback loop. (A-E) MCF7–HER2$^+$PTEN$^-$ cells secreted 3- to 5-fold higher levels of IL6, IL8, and CCL5 compared to MCF7–HER2$^+$ or MCF7–PTEN$^-$ cells as determined by RayBio human cytokine antibody Array 5 (A). The intensity of each blot compared to control was determined by Kodak image analyzer (B) and confirmed by ELISA (C). Downregulation of PTEN in HER2-amplified breast cancer cells, BT474, SKBR3, HCC1954, and Sum159–HER2$^+$ (D) results in increased levels of these cytokines in vitro (E). (F-H) Secretion of all three cytokines in Sum159–HER2$^+$PTEN$^-$ cells were completely inhibited by the NF-kB inhibitor (5 mM Bay11-7082), or combined inhibition of Akt and Stat3, while Akt (5 mM perfosine) or Stat3 (1 mM Stat3 Inhibitor VII) reduced the levels of these cytokines by 50%. Addition of recombinant IL6 to Sum159–HER2$^+$PTEN$^-$ cells stimulated the levels of all three cytokines, while blocking IL6 using the IL6R antibody (at 5 mg/ml) reduced their levels by more than 50%. (I) IL6 activated Akt, Stat3, and NF-kB pathways while suppressing PTEN expression. (J) An IL6 feedback loop is schematically illustrated. Scale bar, 100 mm.
Figure 13:
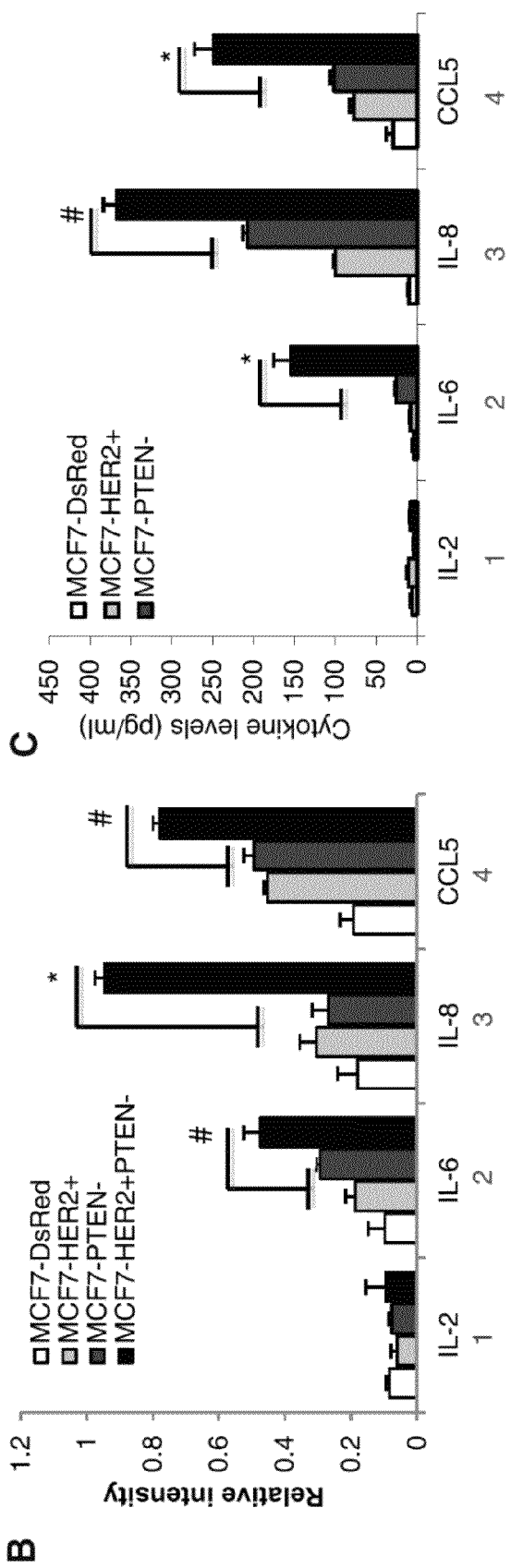
Figure 13:
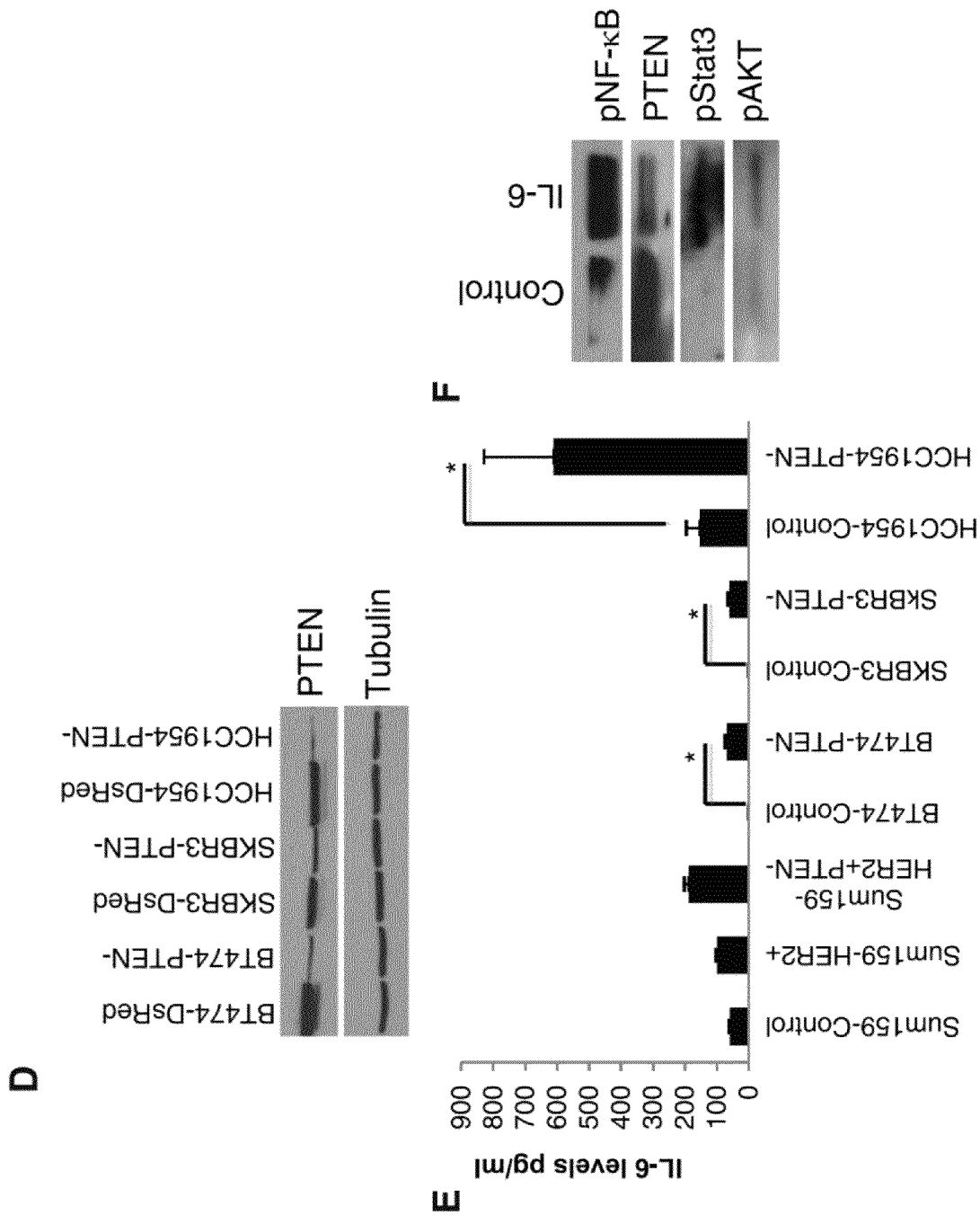
Figure 13:
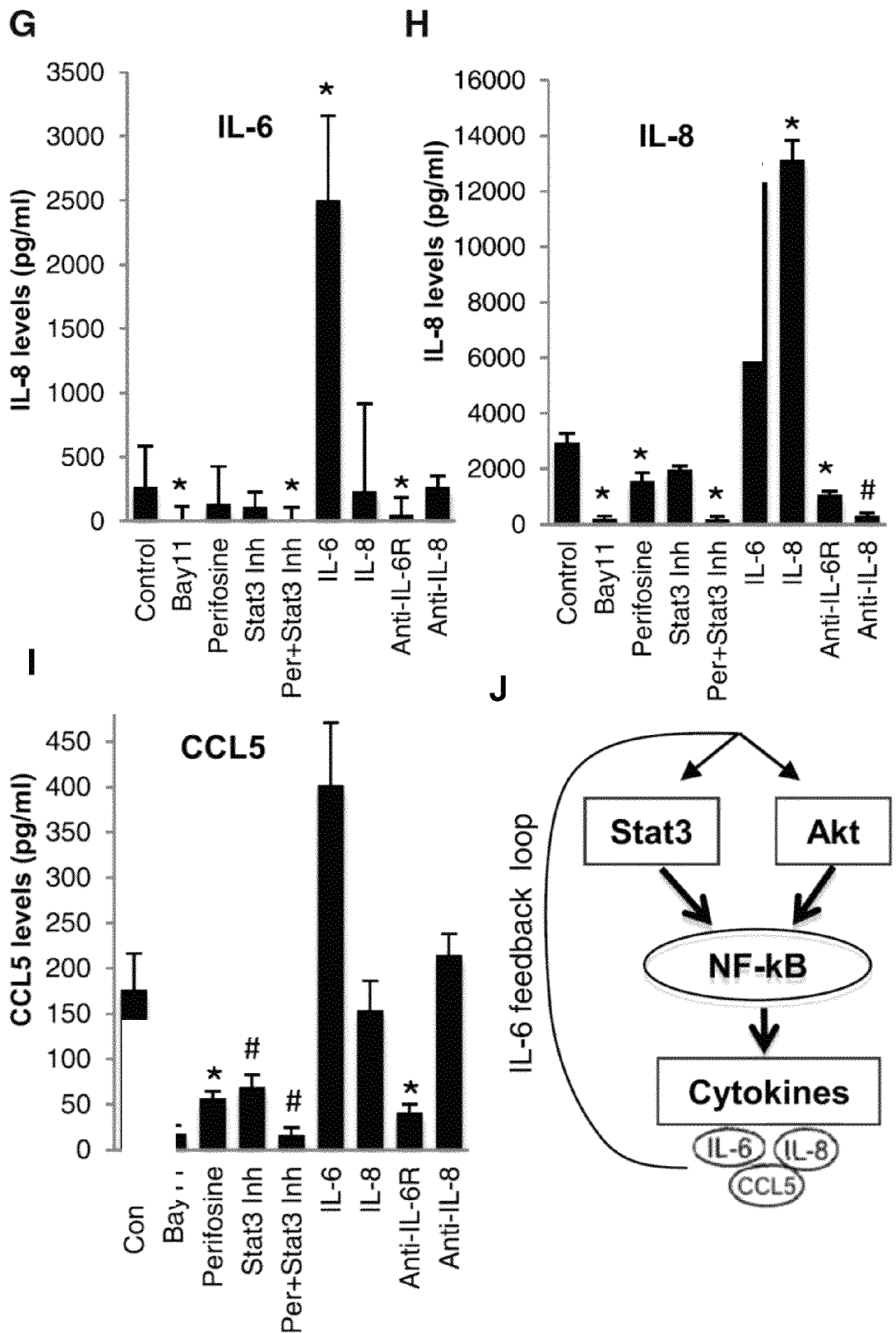

The NF-kB transcription factor is involved in the transcription of a number of cytokine genes including IL6, IL8, and CCL5 (Yu et al., 2010; herein incorporated by reference in its entirety). Furthermore, IL6-activated NF-kB signaling is mediated by Stat3 and Akt signaling pathways (Iliopoulos et al., 2009; herein incorporated by reference in its entirety). Experiments conducted during development of embodiments of the present invention demonstrate that recombinant IL6 activated Akt, Stat3, and NF-kB pathways while suppressing PTEN expression as shown by western blotting (SEE FIG. 13F) Inhibitors of NF-kB, Akt, and Stat3 were used to determine their effects on cytokine production in HER2+PTEN− cells. A Stat3 inhibitor or the Akt inhibitor perifosine only partially inhibited secretion of all three cytokines (SEE FIGS. 13G-13I). In contrast, inhibition of NF-kB using Bay11 or combined inhibition of Akt and Stat3 pathways completely suppressed secretion of these cytokines (SEE FIGS. 13G-13I). The effect of recombinant cytokines or cytokine-blocking antibodies on cytokine production was determined. IL6, but not IL8, increased the production of all three cytokines, an effect that was completely inhibited by anti-IL6R antibody. In contrast, addition of recombinant IL8, or an IL8 blocking antibody, had no significant effect on production of the other cytokines (SEE FIGS. 13G-13I). Together, these results indicate that Stat3 and Akt signaling through NF-kB increases the production of cytokines including IL6, a cytokine whose production is necessary to maintain a positive feedback loop as illustrated in FIG. 13J.

Figure 14:
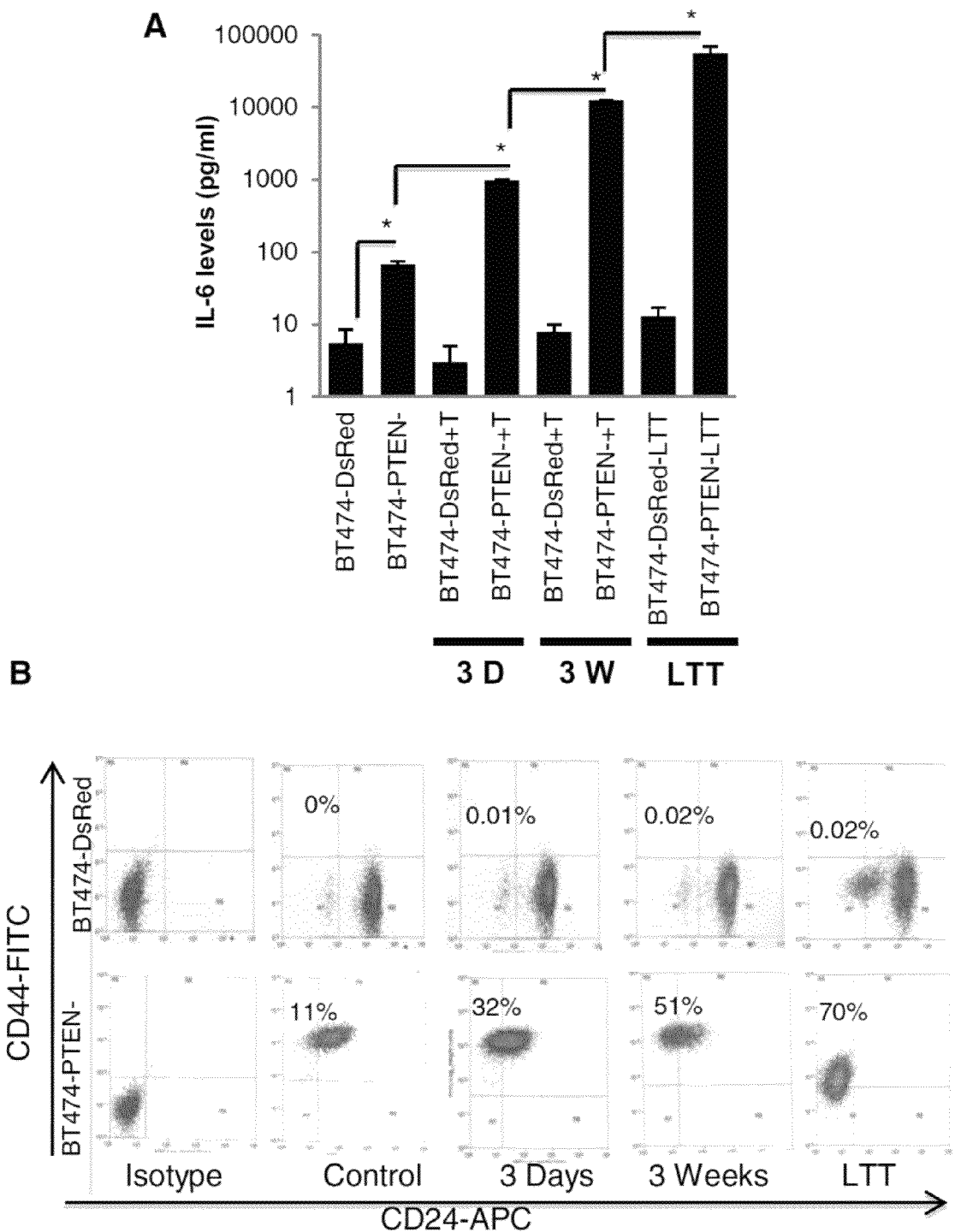
FIGS. 14A-G show experiments demonstrating that an IL6 mediated inflammatory loop expands the CSC population that displays characteristics of EMT. (A) Parental BT474-DsRed cells demonstrated a modest decrease in IL6 levels after 3 days of trastuzumab treatment with a 2-fold increase after LTT (more than 3 weeks); however, treatment of BT474-PTEN$^-$ cells resulted in an increase of more than 10-fold in IL6 levels after 3 days and more than 100-fold after 3 weeks, reaching to an increase of several 100-fold in LTT cells. (B) Trastuzumab treatment gradually increased the percentage of cells expressing the CD44$^+$CD24$^-$ markers in BT474-PTEN$^-$ cells compared to parental BT474-DsRed cells that are predominantly CD44$^-$ CD24$^+$. (C) Blocking IL6R in early stage inhibited this process.
Figure 14:
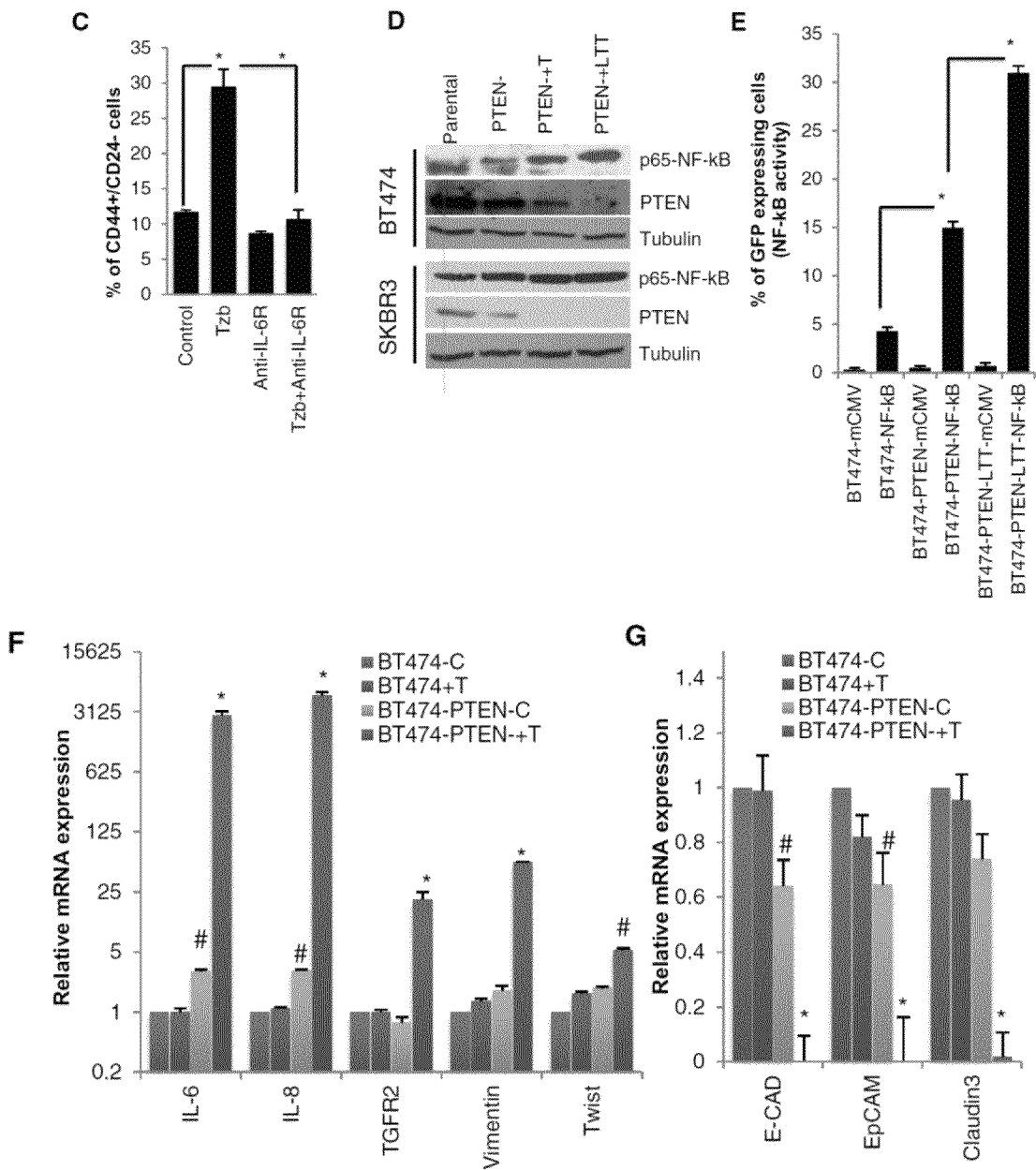

Trastuzumab Treatment of PTEN-Deleted Cells Activates an IL6 Inflammatory Loop Expanding the CSC Population Experiments were conducted during development of embodiments of the present invention to determine the effects of trastuzumab treatment on secretion of cytokines in trastuzumab-sensitive and trastuzumab-resistant cells. Trastuzumab-sensitive BT474-DsRed cells showed a modest decrease in IL6 levels after 3 days of trastuzumab treatment. However, there was approximately a 2-fold increase in IL6 secretion when cells were treated for 3 weeks or longer (SEE FIG. 14A). In contrast, trastuzumab treatment of resistant BT474-PTEN cells resulted in greater than 10-fold increase in IL6 after 3 days and several 100-fold after 3 weeks of trastuzumab treatment (SEE FIG. 14A). The effects of trastuzumab-mediated IL6 production on CSCs were also tested. Parental BT474-DsRed cells contain no detectable CD44−/CD24− cells, a situation that was not significantly altered after trastuzumab treatment. In contrast, downregulation of PTEN in these cells generated a population that contained approximately 10% CD44$^+$/CD24$^-$ cells (FIG. 14B). Furthermore, culture of BT474-PTEN cells in the presence of trastuzumab further increased the proportion of CD44$^+$/CD24$^-$ cells to 32% after 3 days, 51% after 3 weeks, and 70% when these cells were cultured for a month in the presence of trastuzumab (long-term treatment [LTT]) (SEE FIG. 14B). I BT474-PTEN LTT cells maintained this phenotype even in the absence of trastuzumab in subsequent passages. To determine whether induction of the CSC phenotype was dependent on IL6 production, the effect of addition of IL6 receptor antibody on induction of the CSC phenotype was assessed. Addition of this antibody not only reduced the CD44$^+$/CD24$^-$ CSC population in BT474-PTEN$^-$ cells, but also completely blocked the increase in this population induced by trastuzumab (SEE FIG. 14C). The ability of the anti-IL6R antibody to affect the CD44$^+$/CD24$^-$ population in Sum159 cells, which lack the expression of the luminal CD24 marker, was examined. Anti-IL6R antibody treatment of these cells for 5 days resulted in generation of CD24+ cells (11%) and substantial growth arrest. The effect of IL6 in different cell lines (MCF7, Sum159, BT474, and SKBR3) representing different breast cancer subtypes was further demonstrated by analyzing both Aldefluor and CD44$^+$/CD24$^-$ phenotypes. Although IL6 induced the CD44$^+$/CD24$^-$ phenotype in all cell lines, it only increased the Aldefluor-positive population in MCF7 and Sum159 cells while slightly reducing in HER2-amplified BT474 and SKBR3 cell lines. This discrepancy may be explained by the existence of different stem cell populations in different breast cancer subtypes.

To determine whether NF-kB activation was involved in these processes, p65 NF-kB phosphorylation was assessed. Increased NF-kB phosphorylation was observed following the trastuzumab treatment in BT474-PTEN$^-$ and SKBR3-PTEN$^-$ cells, compared to parental cells, which was further enhanced in trastuzumab LTT cells (SEE FIG. 14D). Stepwise activation of NF-kB over time of trastuzumab treatment was also confirmed utilizing an NFkB reporter assay (SEE FIG. 14E).

EMT has been linked to the CSC phenotype (Mani et al., 2008; herein incorporated by reference in its entirety), a population known to be regulated by IL6. In addition to a several 1,000-fold increase in the IL6 and IL8 transcripts, mRNA expression of EMT markers, TGFR, Vimentin, and Twist were upregulated by 5- to 25-fold in BT474-PTEN$^-$ cells but not in parental BT474 cells upon trastuzumab treatment (SEE FIG. 14F). Furthermore, trastuzumab treatment of BT474-PTEN$^-$ cells resulted in downregulation of epithelial-associated genes including E-cadherin, EpCAM, and Claudin (SEE FIG. 14G).

Figure 5:
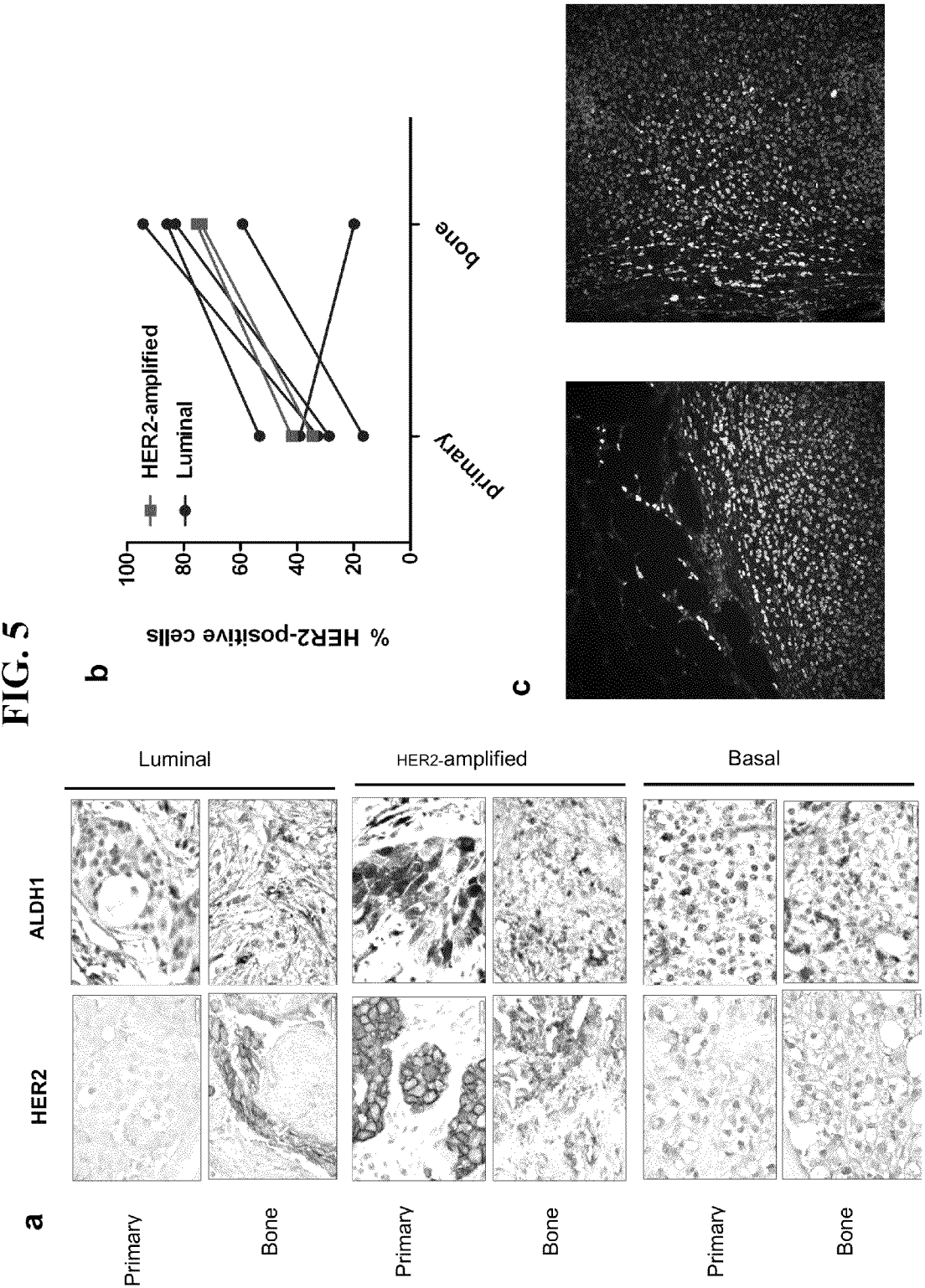
FIG. 5 shows expression of HER2 and ALDH1 in matched primary and bone metastasis in various breast cancer patients tumor (a). There was greater HER2 expression demonstrated by immunohistochemistry in matched bone metastatic tumor compared to primary tumor in patient with luminal breast cancer. (b) Dot plot of HER2 by AQUA in primary tumor and bone met. (C) Representative pictures of a luminal tumor shows overlapping of HER2 and ALDH expression, especially at the edge of tumor
Figure 6A:
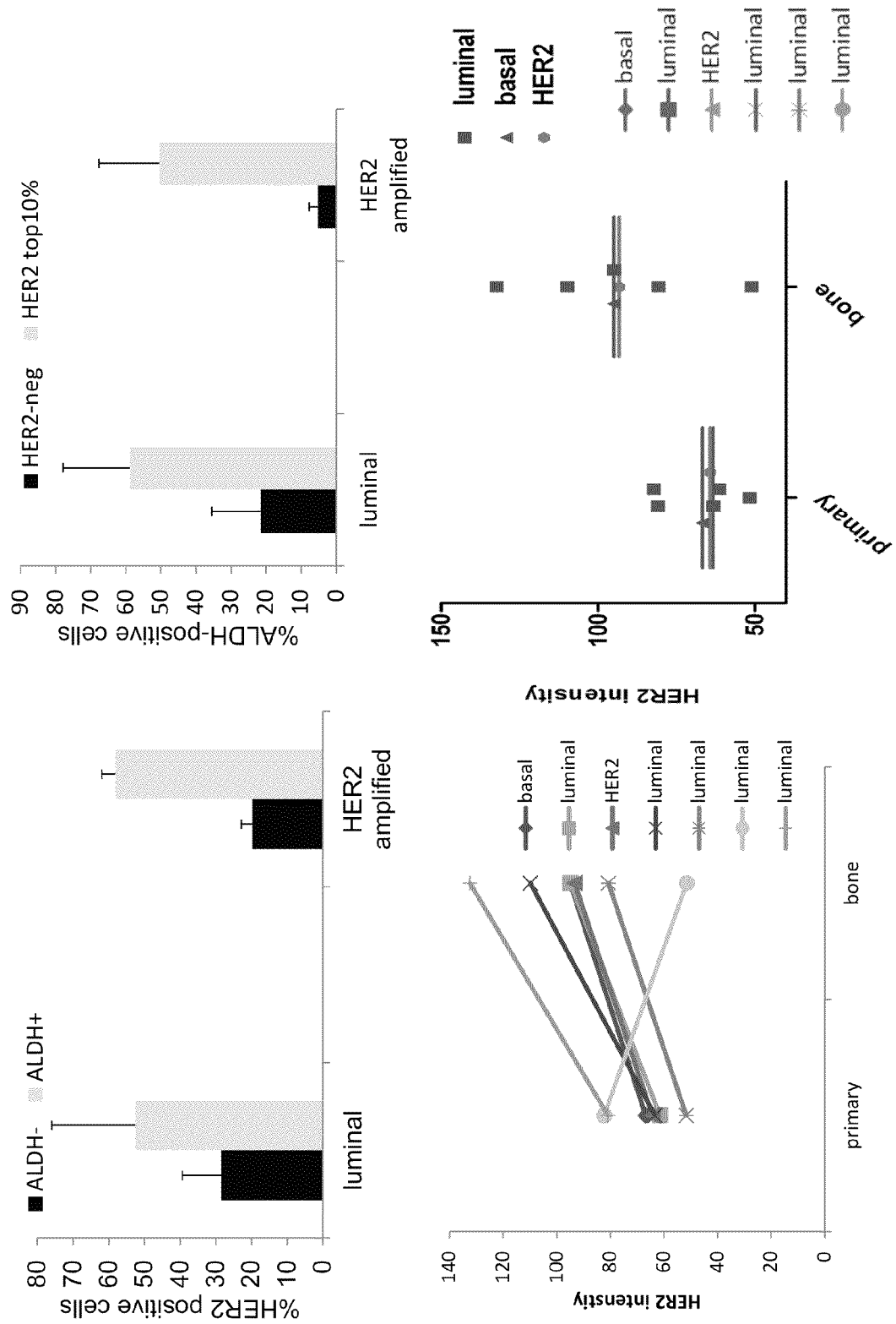
FIGS. 6a and 6b show overlapping of HER2 and ALDH in different tumor subtypes quantitated by AQUA.
Figure 6B:
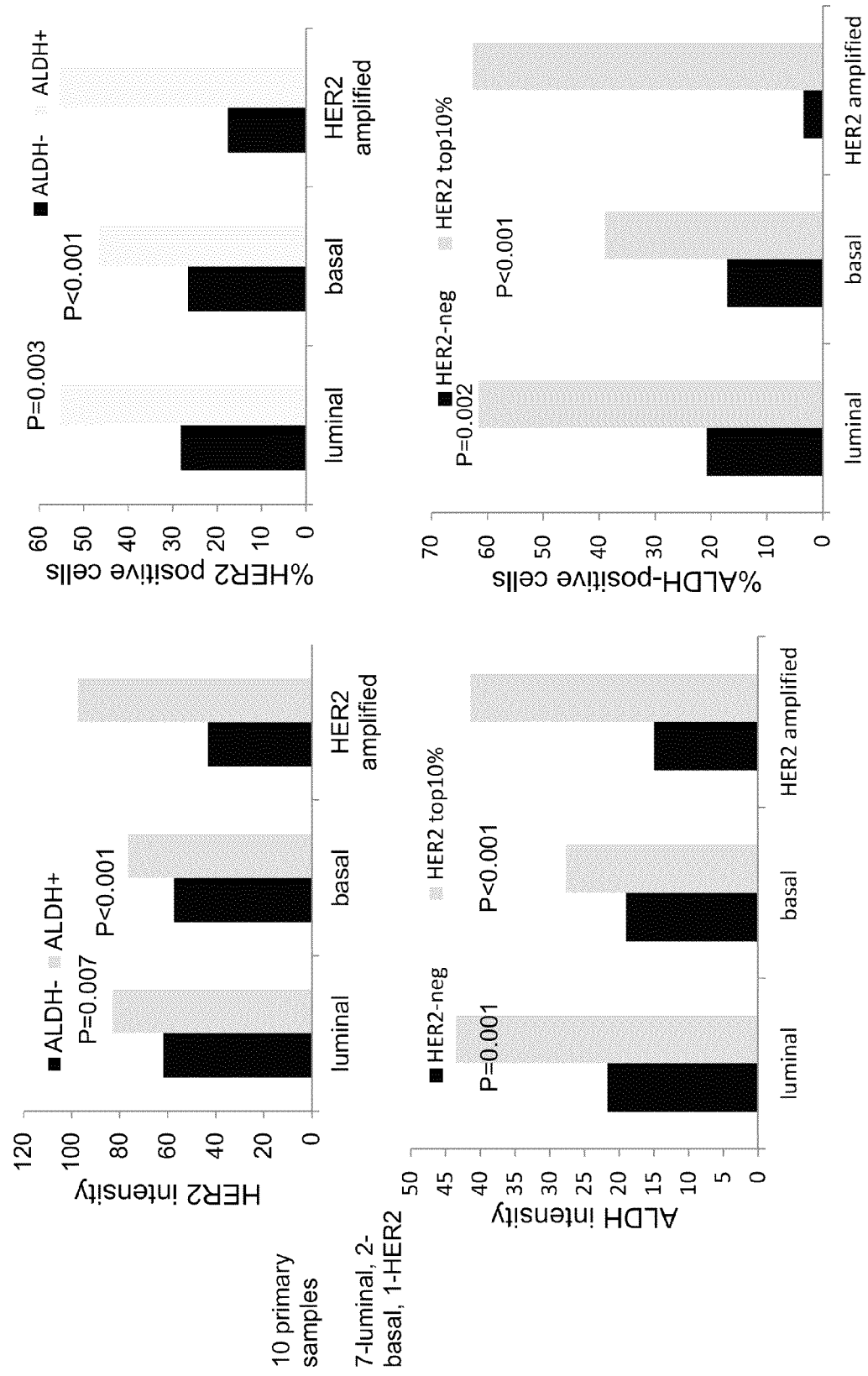
Figure 15:
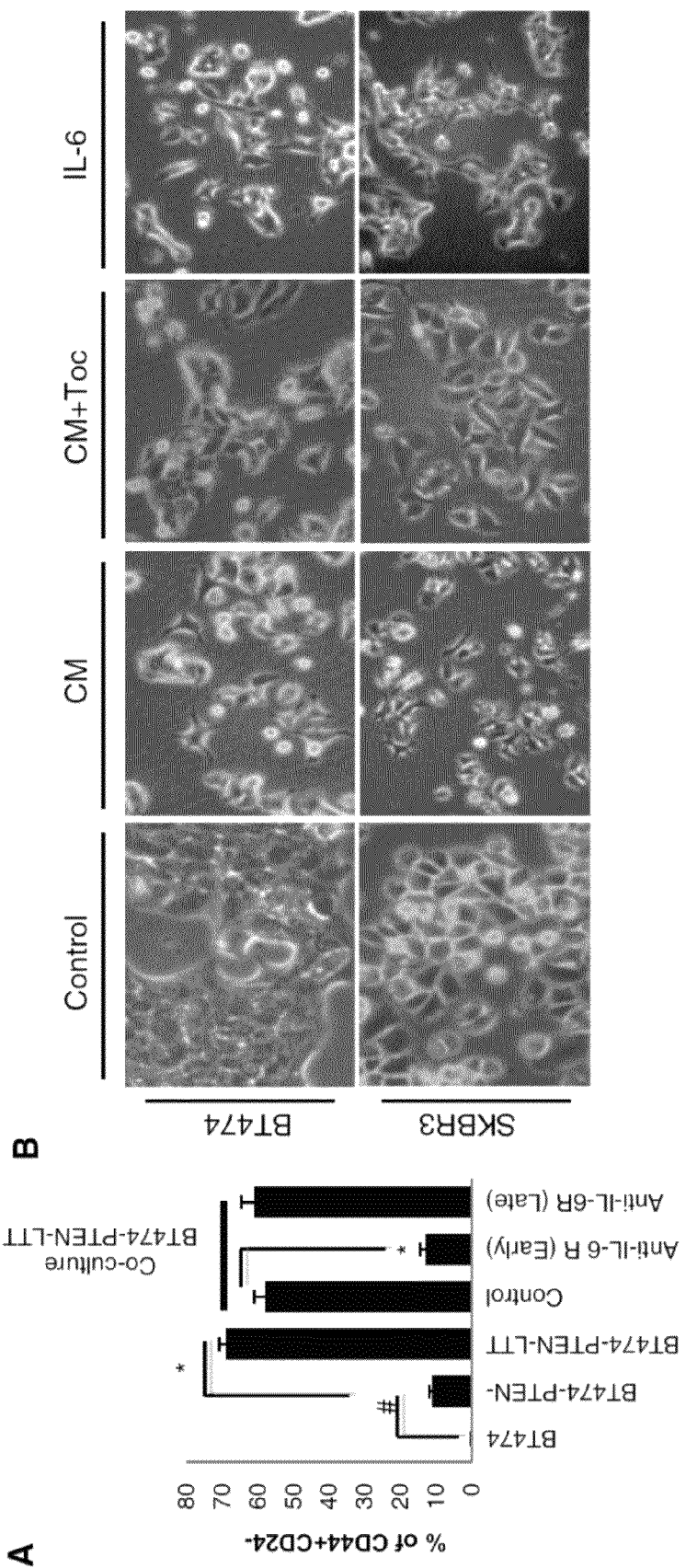
FIGS. 15A-E show experiments demonstrating that an IL6 inflammatory loop mediates Trastuzumab resistance through autocrine and paracrine mechanisms. (A-C) When co-cultured with BT474-PTEN$^-$LTT cells for 2 weeks, parental BT474-DsRed cells acquired a CD44$^+$CD24$^-$ phenotype, a transition that was inhibited by the addition of anti-IL6R antibody at the beginning of co-culture (A and B). However, once cells acquired the CD44$^+$/CD24$^-$ phenotype, they became resistant to anti-IL6R antibody (late). CM from BT474-PTEN$^-$LTT cells or recombinant IL6 was able to induce mesenchymal phenotype and CD44 expression in both parental BT474-DsRed and SKBR3-DsRed cells (B and C). (D) CM from BT474-PTEN$^-$LTT cells or recombinant human IL6 increased the sphere formation of BT474-DsRed cells providing resistance to trastuzumab an effect that was reversed by anti-IL6R antibody. (E) Trastuzumab reduced the number of viable BT474-DsRed cells by 50%, while it had no effect on the viability of BT474-PTEN$^-$ cells or BT474-DsRed cells when they were grown in the presence of CM or IL6, an effect reversed by anti-IL6R antibody.
Figure 15:
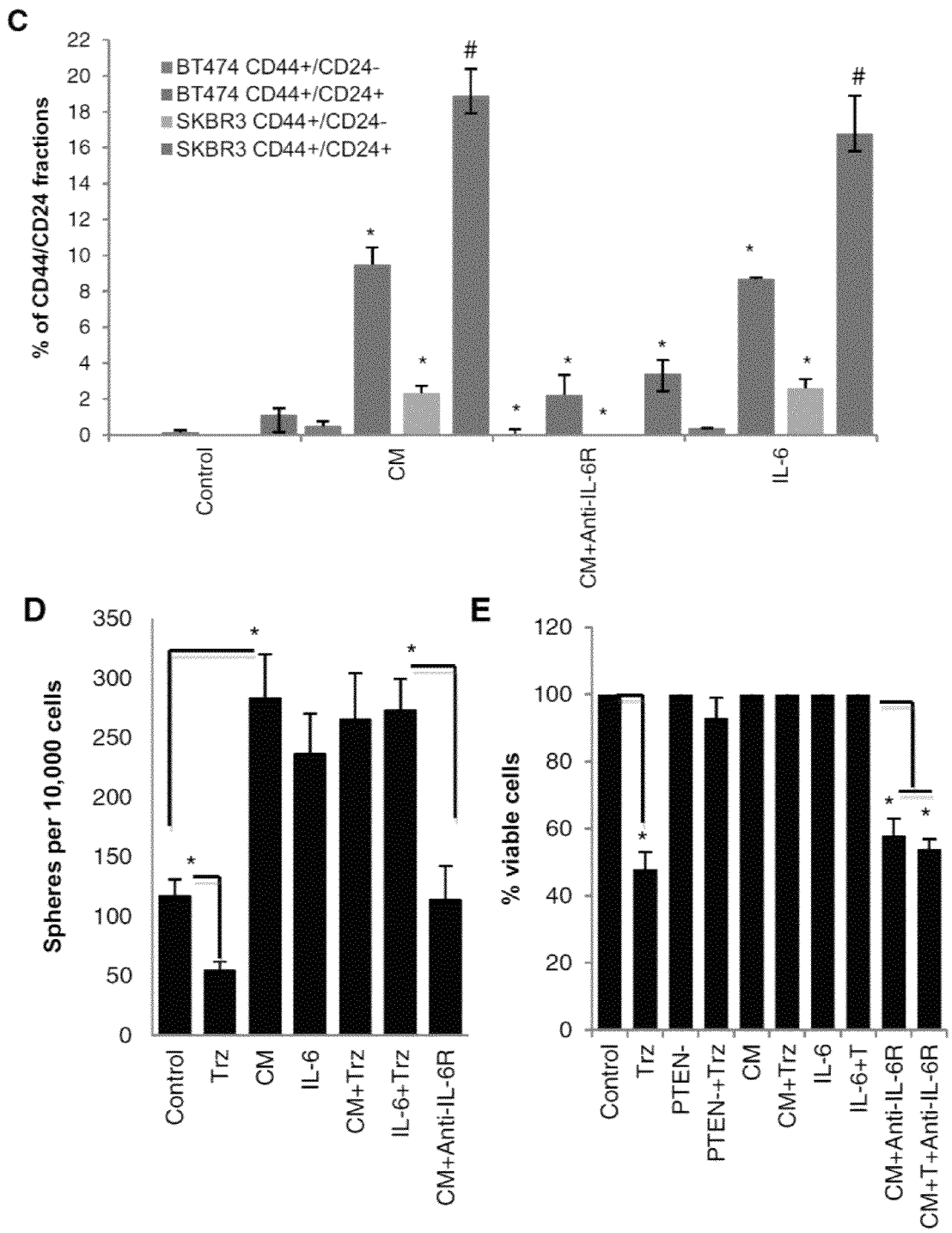

Paracrine Induction of a Trastuzumab-Resistant CSC Phenotype in Parental BT474 Cells To determine whether paracrine factors could also act upon PTEN wild-type (BT474 cells), parental BT474 cells were co-cultured with BT474-PTEN$^-$LTT cells that had been cultured for 4 weeks in the presence of trastuzumab. The green fluorescent protein (GFP) label in the parental (PTEN wild-type) cells allowed separation by flow cytometry of cell populations following co-culture. Co-culture of parental BT474-GFP cells with BT474-PTEN$^-$LTT cells increased the percentage of CD44$^+$/CD24$^-$ CSCs from 0.1% to 60% in parental cells (SEE FIG. 15A). Single GFP-expressing parental BT474 cells were sorted after 3 weeks of co-culture with BT474-PTEN$^-$LTT and generated multiple colonies. Although colonies of parental BT474 cells did not maintain the CD44$^+$/CD24$^-$ phenotype, they were primarily CD44$^+$/CD24$^+$, which is distinctly different from the control BT474 cells. Furthermore, addition of anti-IL6R antibody at the time of co-culture inhibited the induction of the CD44$^+$/CD24$^-$ phenotype while late treatment with anti-IL6R antibody had no effect in parental cells (SEE FIG. 5A). To examine the direct role of IL6 in these processes, parental BT474 or SKBR cells were stimulated with recombinant IL6 or conditioned medium (CM) from BT474-PTEN$^-$LTT cells in the presence or absence of anti-IL6R antibody. Either IL6 or CM treatment of cells for 5 days induced a mesenchymal phenotype associated with a 10-fold increase in the expression of the CD44 marker, while the anti-IL6R antibody was able to reverse these phenotypic changes (SEE FIGS. 5B and 5C). Longer exposure of these cells to CM or IL6 (10 days) further increased the CD44$^+$/CD24$^-$ and CD44$^+$/CD24$^-$ populations, suggesting that, over time, these populations are enriched.

Experiments were conducted during development of embodiments of the present invention to examine whether the IL6 renders the CSC population resistant to trastuzumab in parental BT474 cells in vitro. While IL6 or CM significantly increased the number tumorspheres in suspension cultures of BT474 cells, trastuzumab treatment reduced the sphere forming cells by more than 50% (SEE FIG. 5D). In contrast, trastuzumab failed to inhibit sphere formation in the presence of IL6 or CM, while addition of anti-IL6R antibody reduced the number of tumorspheres induced by CM in BT474 cells (SEE FIG. 5D).

BT474 cells were stimulated by CM or IL6 in the presence or absence of trastuzumab and/or anti-IL6R antibody. While parental BT474 cell growth was reduced by 50% following 48 hr of trastuzumab treatment, BT474-PTEN$^-$ cells were unaffected (SEE FIG. 5E). Addition of CM from BT474-PTEN$^-$LTT cells or recombinant IL6 rendered parental BT474 cells resistant to trastuzumab, an effect that was blocked by anti-IL6R antibody (SEE FIG. 5E).

Figure 12:
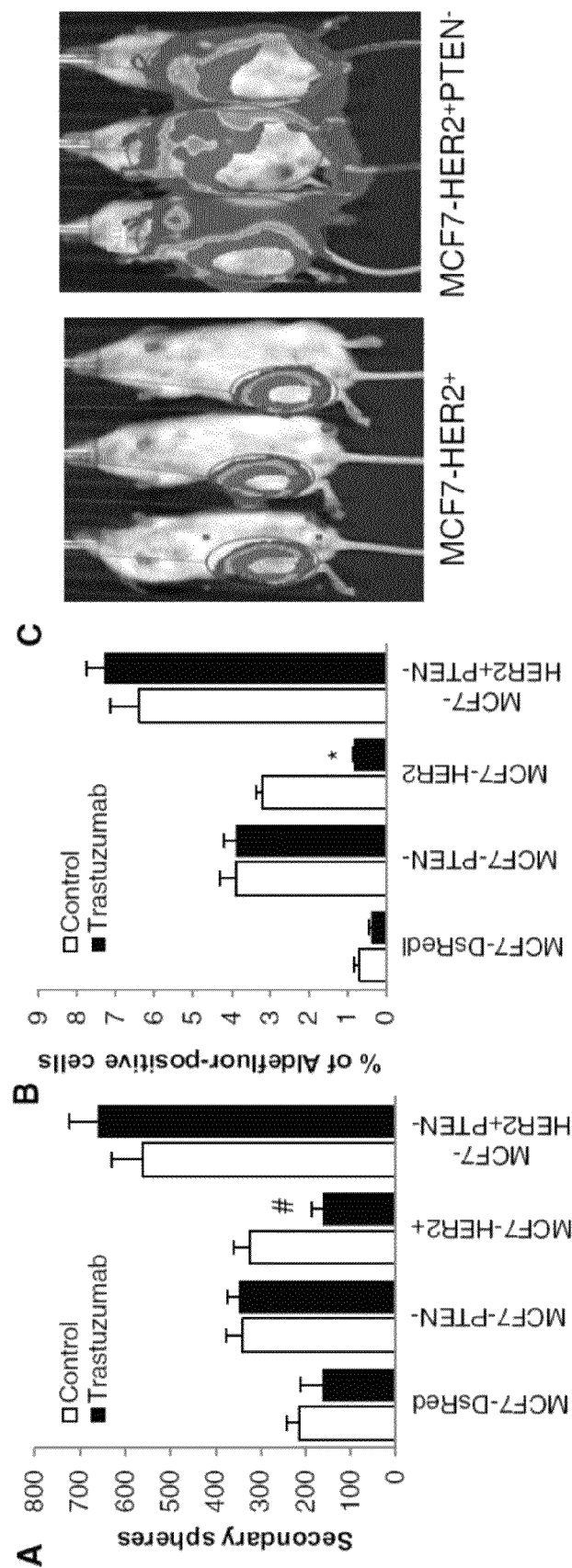
FIGS. 12A-I show images and graphs demonstrating PTEN downregulation and HER2 overexpression generate trastuzumab-resistant tumors in NOD/SCID mice. (A-I) Trastuzumab treatment of primary spheres of MCF7–HER2$^+$ and Sum159–HER2$^+$ reduced the formation of secondary spheres by 50%, while the secondary spheres from MCF7–PTEN$^-$, Sum159–PTEN$^-$, MCF7–HER2$^-$PTEN$^-$, and Sum159–HER2$^+$PTEN$^-$ cells were not affected by trastuzumab (A and D). Trastuzumab treatment had no effect on the Aldefluor-positive cell population in MCF7–HER2$^+$PTEN$^-$ and Sum159–HER2$^+$PTEN$^-$ cells, while it reduced this population by more than 50% in MCF7–HER2$^+$ and Sum159–HER$^2$+ cells (B and E). MCF7–HER2$^+$PTEN$^-$ and Sum159–HER2$^+$PTEN$^-$ cells, compared to MCF7–HER2$^+$ and Sum159–HER2$^+$ cells, generated rapidly growing tumors (C and F) with metastasis to liver and lung (G). MCF7–HER2$^+$ tumors responded to trastuzumab treatment in mice leading to inhibition of tumor growth and decrease in Aldefluor-positive population in mice, while MCF7–HER2+ PTEN$^-$ tumors were resistant to trastuzumab (H and I).
Figure 12:
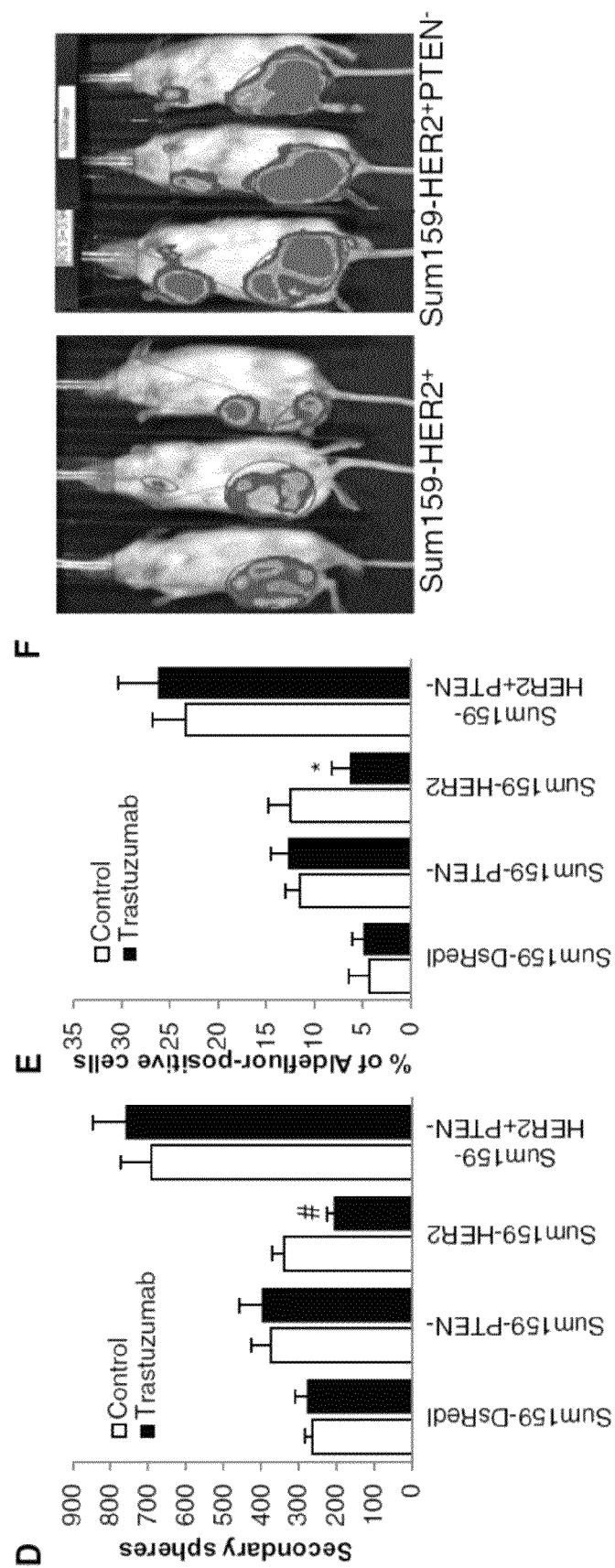
Figure 12:
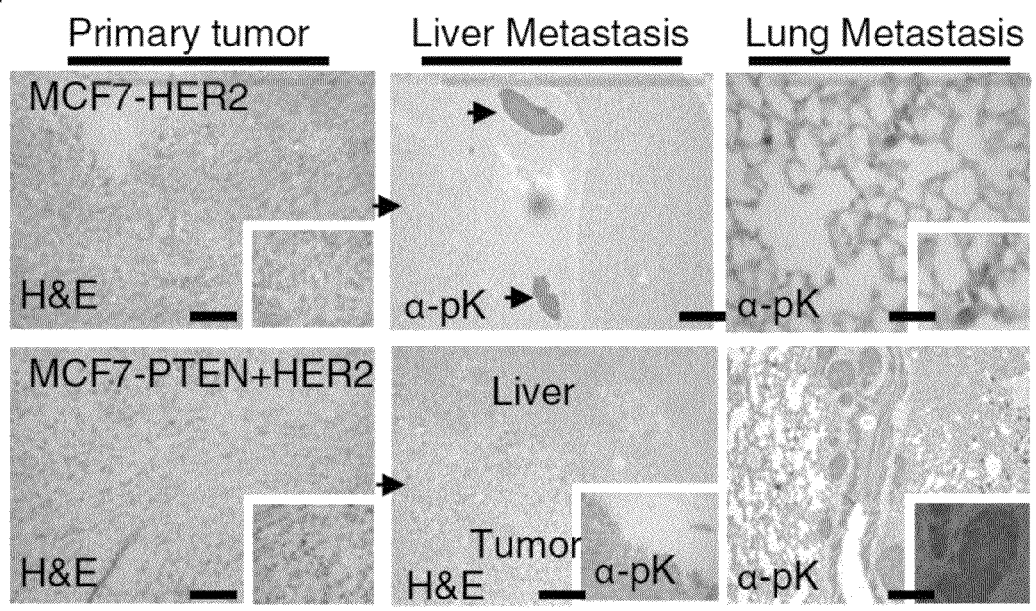
Figure 12:
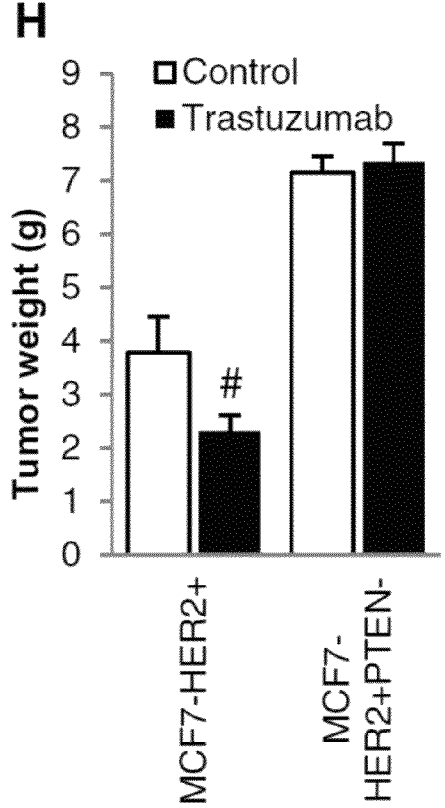
Figure 12:
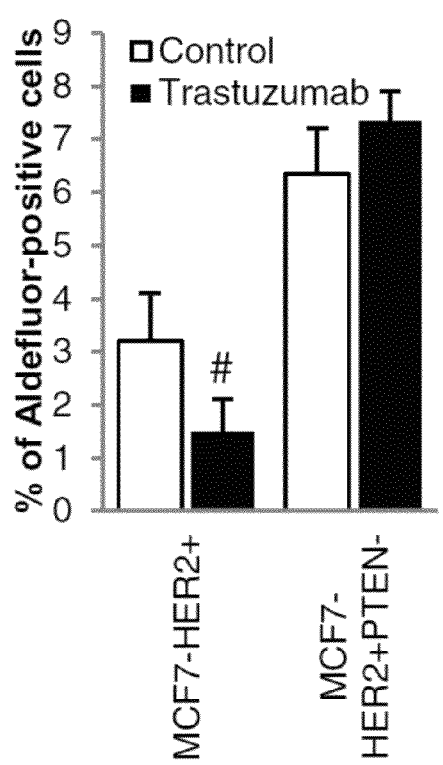
Figure 16:
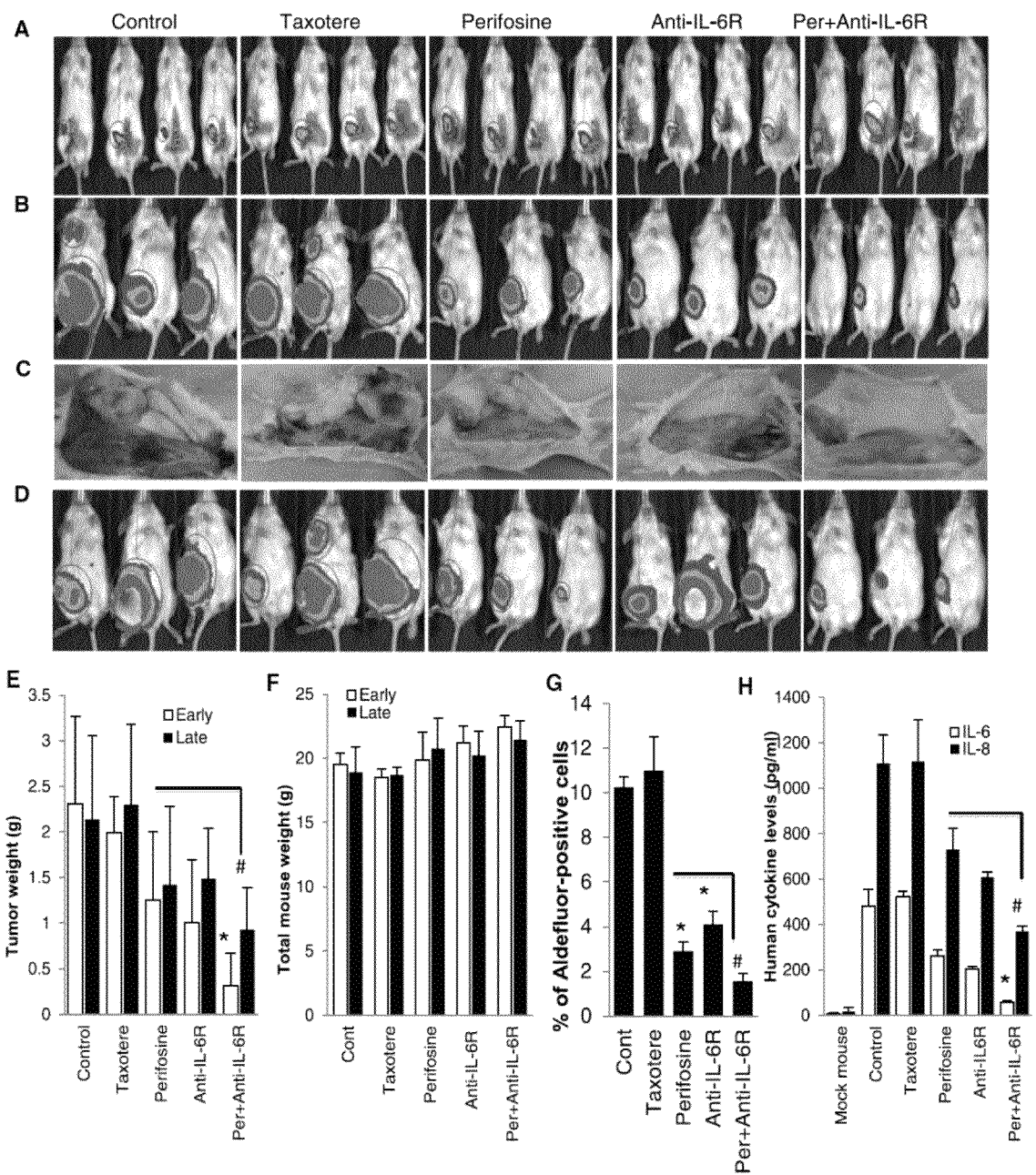
FIGS. 16A-H show targeting of the IL6 pathway reduces the CSC population, inhibiting tumor growth and metastasis in mouse xenografts. (A and B) Metastatic Sum159–HER2$^+$ PTEN$^-$ cells were implanted into the fat pads of NOD-SCID mice (A). In early treatment (started on the day of implantation) settings, docetaxel (10 mg/kg) once a week, perifosine (20 mg/kg) twice a week and anti-IL6R (10 mg/kg) once a week were administered for 8 weeks (B). (C) Representative pictures of mice for each early treatment group. (D and E) In late treatment (started after the establishment of tumor ~0.4 cm), drugs were administered as in the early treatment. Tumors were measured following 8 weeks of treatment. There was an 80% and 50% reduction in tumor size in early and late perifosine+anti-IL6R antibody combination treatments, respectively. (F) Mice treated with perifosine, anti-IL6R antibody, or the combination showed less body weight loss than those treated with docetaxel alone. (G) Tumors from mice treated with perifosine or anti-IL6R antibody alone or the combination showed substantial reduction in Aldefluor-positive cell population. In contrast, tumors from control or docetaxel-treated mice, showed no reduction. (H) Serum levels of human IL6 and IL8, measured by ELISA in control and docetaxel-treated mice were 2-fold higher than in perifosine, anti-IL6R antibody, alone or in combination-treated mice.

Blocking the IL6 Receptor Inhibits the CSC Population Reducing Tumor Growth and Metastasis in Trastuzumab-Resistant Mouse Xenografts The effects of inhibition of IL6 signaling was assessed in vivo utilizing anti-IL6R antibody, and Akt signaling using perifosine in SUM159–HER2$^+$PTEN$^-$ luciferase labeled trastuzumab-resistant xenografts (SEE FIGS. 12E and 12F). The effects of these treatments on tumor growth were assessed by luminescent imaging or by weighing tumors after mice were sacrificed. Treatments were started on the day of tumor inoculation (early) (SEE FIG. 16B) or delayed until palpable tumors were established, at approximately 0.4 cm in size (late). The effects of the chemotherapy agent docetaxel (TAXOTERE), the Akt inhibitor perifosine, anti-IL6R antibody, or perifosine plus anti-IL6R antibody were assessed after 8 weeks of treatment (SEE FIGS. 16B, 16D, and 16E). In contrast to the chemotherapeutic agent docetaxel, perfosine, or anti-IL6R antibody significantly inhibited tumor growth while the combination of perifosine and anti-IL6R antibody showed greatest inhibition of tumor growth with complete inhibition of tumors in 50% of animals in which treatments were begun early (SEE FIGS. 16B-16E). Furthermore, while control and docetaxel-treated mice lost body weight, those treated with anti-IL6R antibody alone or in combination with perifosine maintained normal body weight (SEE FIG. 16F). The effects of these treatments on the CSC populations were assessed by the Aldefluor assay. Although docetaxel had no significant effect on the percent of Aldefluorpositive cells, both perifosine and anti-IL6R antibody significantly reduced this population. Furthermore, the combination of perifosine and anti-IL6R antibody resulted in the greatest reduction in the Aldefluor-positive population with more than 80% reduction compared to control or docetaxel-treated tumors (SEE FIG. 16G). To determine whether these treatments effected tumor cytokine production, the level of human cytokines in the serum of treated mice was determined utilizing a human specific ELISA. Although docetaxel had no significant effect on serum IL6 or IL8 levels, perifosine or anti-IL6R antibody treatment significantly reduced the levels of these cytokines. Furthermore, the combination of perifosine and anti-IL6R antibody produced a reduction greater than 80% in levels of human serum IL6 compared to untreated or docetaxel-treated mice (SEE FIG. 16H).

Figure 17:
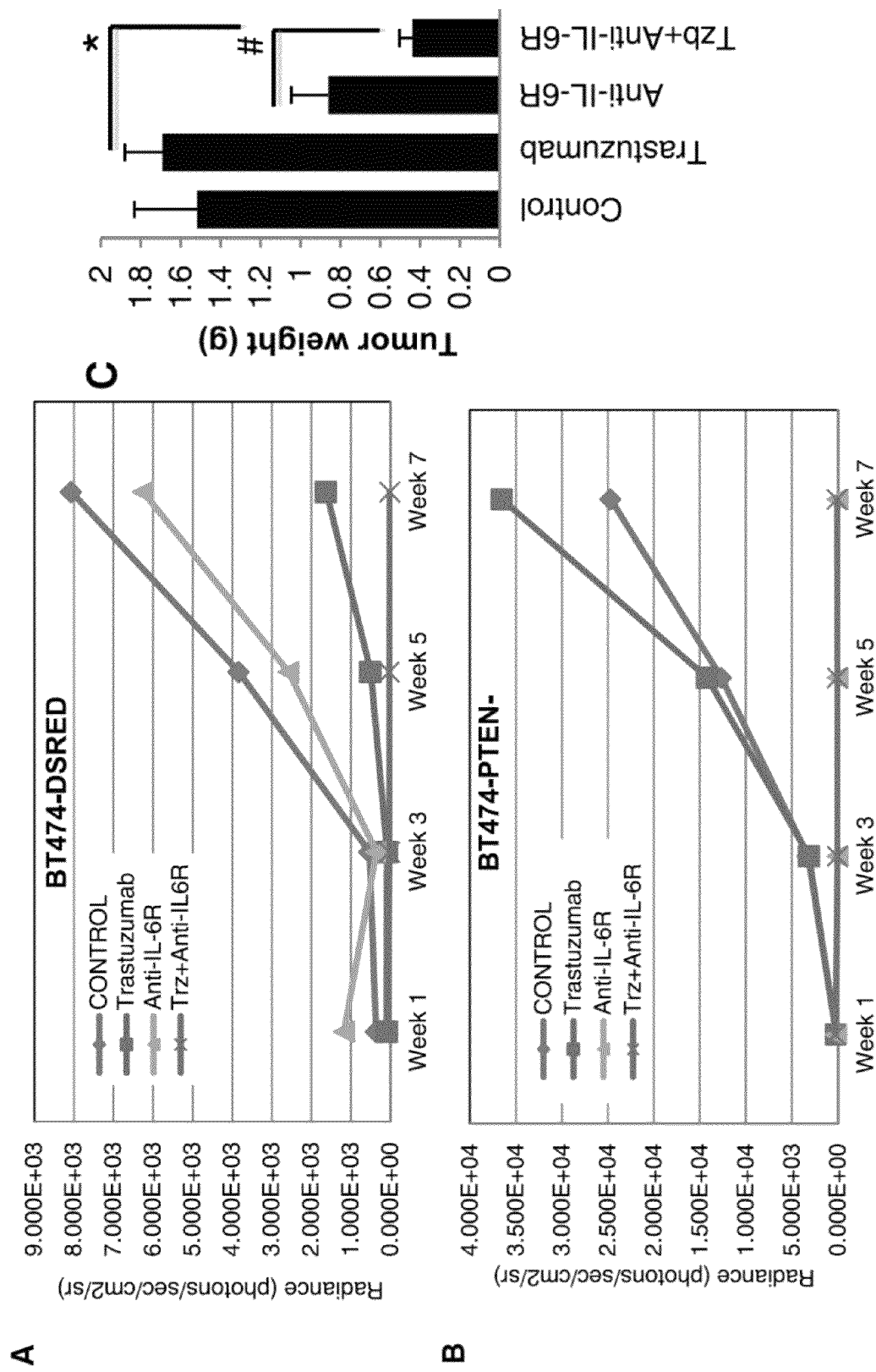
FIGS. 17A-F show that IL6 receptor antibody overcomes de novo and acquired Trastuzumab resistance in mouse xenografts. (A-C) Combining anti-IL6R antibody with trastuzumab completely suppresses tumor growth in mice bearing trastuzumab-sensitive BT474-DsRed tumors (A) and overcomes de novo trastuzumab resistance in BT474-PTEN$^-$ xenografts (B and C). (D) Anti-IL6R antibody completely inhibited the development of secondary metastasis in distant organs after the primary tumors were excised in NOD-SCID mice. (E) Serum IL6 levels were significantly higher in trastuzumab-treated mice while anti-IL6R antibody-treated mice showed the lowest levels of serum IL6. (F) Frequencies of CSC were calculated in serial reimplantation of residual tumors from treated mice, showing significantly lower CSCs in anti-IL6R antibody alone or combination treatments.
Figure 17:
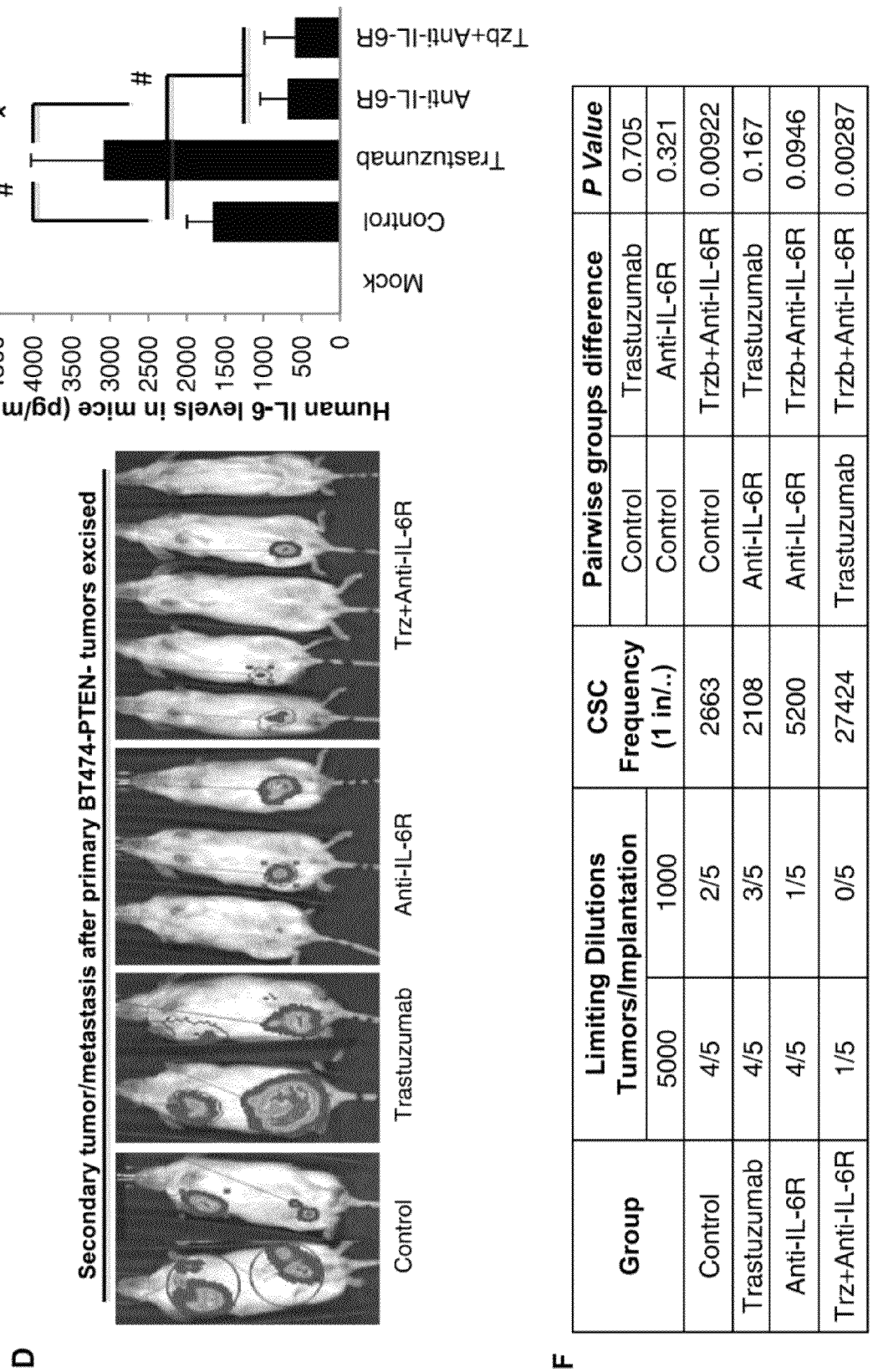

Anti-IL6 Receptor Antibody Overcomes Acquired and De Novo Trastuzumab Resistance Experiments were conducted during development of embodiments of the present invention to examine the effect of anti-IL6R antibody on trastuzumab-sensitive BT474-DsRed and trastuzumab-resistant BT474-PTEN⁻ xenografts. The growth of parental BT474-DsRed xenografts was significantly inhibited by trastuzumab treatment compared to saline treatment over a 7-week period (FIG. 17A). However, tumors in trastuzumab-treated mice began to grow by Week 5, demonstrating acquired trastuzumab resistance. Although the anti-IL6R antibody had little effect on tumor growth on its own, when added to trastuzumab, it completely blocked tumor growth up to Week 7 of follow-up (FIG. 17A). In contrast, trastuzumab had no effect on the growth of BT474-PTEN⁻ xenografts while the anti-IL6R antibody completely blocked tumor growth when given alone or in combination with trastuzumab (FIG. 17B). Addition of anti-IL6R antibody to established tumors (late treatment) completely blocked tumor growth as assessed by tumor weight at sacrifice (FIG. 17C). To determine the effects of these treatments on the development of metastasis, we excised primary BT474-PTEN⁻ tumors after 8 weeks of treatment and assessed subsequent development of local and distant metastasis by luciferase imaging (FIG. 7D). While control or trastuzumab-treated mice quickly developed secondary tumors and distant metastasis requiring euthanization, there were no distant metastasis detected in anti-IL6R antibody-treated mice (FIG. 7D). The effects of these treatments were also reflected in human cytokine levels secreted in the bloodstream of these animals as determined by ELISA (FIG. 7E).

One of the hallmarks of CSC model is their ability to initiate tumors in secondary reimplantation assays (Clarke et al., 2006; herein incorporated by reference in its entirety). We therefore utilized a reimplantation assay to determine the frequency of breast CSCs (tumor-initiating cells) in residual tumors from control mice and mice treated with trastuzumab or anti-IL6R, alone or in combination. Reimplantation of residual tumor cells into secondary mice showed that the frequency of breast CSCs was actually increased by trastuzumab treatment alone (FIG. 17F). However, the frequency of CSCs in anti-IL6R antibody or anti-IL6R antibody+trastuzumab-treated tumors were reduced by more than 50% and 90%, respectively (FIG. 17F), suggesting that anti-IL6R antibody targets the tumorigenic CSC population.

Various modifications and variations of the described method and system of the invention will be apparent to those skilled in the art without departing from the scope and spirit of the invention. Although the invention has been described in connection with specific some embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

REFERENCES

All publications and patents mentioned in the above specification and/or listed below are herein incorporated by reference in their entireties.

1. Slamon, D. J., et al. Science 235, 177-182 (1987).
2. Vogel, C. L., et al. J Clin Oncol 20, 719-726 (2002).
3. Slamon, D. J., et al. N Engl J Med 344, 783-792. (2001).
4. Vogel, C. L., et al. Oncology 61 Suppl 2, 37-42 (2001).
5. Mass, R. D., et al. Clin Breast Cancer 6, 240-246 (2005).
6. Wolff, A. C., et al. J Clin Oncol 25, 118-145 (2007).
7. Mueller, B. M., et al. Mol Cancer Ther 9, 3024-3032 (2010).
8. Fabi, A., et al. Clin Cancer Res 17, 2055-2064 (2011).
9. Lipton, A., et al. Cancer 116, 5168-5178 (2010).
10. Joensuu, H., et al. N Engl J Med 354, 809-820 (2006).
11. Piccart-Gebhart, M. J., et al. N Engl J Med 353, 1659-1672 (2005).
12. Romond, E. H., et al. N Engl J Med 353, 1673-1684 (2005).
13. Smith, I., et al. Lancet 369, 29-36 (2007).
14. Spielmann, M., et al. J Clin Oncol 27, 6129-6134 (2009).
15. Paik, S., Kim, C. & Wolmark, N. N Engl J Med 358, 1409-1411 (2008).
16. Perez, E. A., et al. J Clin Oncol 28, 4307-4315 (2010).
17. Korkaya, H., Paulson, A., Iovino, F. & Wicha, M. S Oncogene 27, 6120-6130 (2008).
18. Korkaya, H. & Wicha, M. S. Clin Cancer Res 15, 1845-1847 (2009).
19. Magnifico, A., et al. Clin Cancer Res 15, 2010-2021 (2009).
20. Ginestier, C., et al. Cell Stem Cell 1, 555-567 (2007).
21. Charafe-Jauffret, E., et al. Cancer Res 69, 1302-1313 (2009).
22. Dontu, G., et al. Genes Dev 17, 1253-1270 (2003).
23. Kennecke, H., et al. J Clin Oncol 28, 3271-3277 (2010).
24. Wicha Dontu, G. Cancer Res 66, 1883-1890; discussion 1895-1886 (2006).
25. Shafee, N., et al. Cancer Res 68, 3243-3250 (2008).
26. Hambardzumyan, D., Squatrito, M. & Holland, E. C. Cancer Cell 10, 454-456 (2006).
27. Korkaya, H., et al. PLoS Biol 7, e1000121 (2009).
28. Diehn, M., et al. Nature 458, 780-783 (2009).
29. Li, X., et al. J Natl Cancer Inst 100, 672-679 (2008).

30. Al-Hajj et al. (2003). Proc. Natl. Acad. Sci. USA 100, 3983-3988.
31. Bachelot et al. (2003). Br. J. Cancer 88, 1721-1726.
32. Berns et al. (2007). Cancer Cell 12, 395-402.
33. Bromberg and Wang. (2009). Cancer Cell 15, 79-80.
34. Cicalese et al. (2009). Cell 138, 1083-1095.
35. Clarke et al. (2006). Cancer Res. 66, 9339-9344.
36. D'Anello et al. (2010). Mol. Cancer 9, 300.
37. Eyler and Rich. (2008). J. Clin. Oncol. 26, 2839-2845.
38. Ginestier et al. (2007). Cell Stem Cell 1, 555-567.
39. Ginestier et al. (2010). J. Clin. Invest. 120, 485-497.
40. Hartman et al. (2011). Cancer Res. 71, 4380-4391.
41. He, et al. (2011). Mol. Oncol. 5, 292-301.
42. Iliopoulos et al. (2009). Cell 139, 693-706.
43. Iliopoulos et al. (2010). Mol. Cell 39, 493-506.
44. Iliopoulos et al. (2011). Proc. Natl. Acad. Sci. USA 108, 1397-1402.
45. Korkaya et al. (2008). Oncogene 27, 6120-6130.
46. Korkaya et al. (2009). PLoS Biol. 7, e1000121.
47. Korkaya, et al. (2011). Clin. Cancer Res. 17, 6125-6129.
48. Lan et al. (2005). Ann. N Y Acad. Sci. 1059, 70-75.
49. Mani et al. (2008). Cell 133, 704-715.
50. Morrison et al. (2011). J. Oncol. 2011, 941876.
51. Nagata et al. (2004). Cancer Cell 6, 117-127.
52. Salgado et al. (2003). Int. J. Cancer 103, 642-646.
53. Weissenberger, et al. (2004) Oncogene 23, 3308-3316.
54. Yao et al. (2010). Proc. Natl. Acad. Sci. USA 107, 15535-15540.
55. Yu et al. (2010). Neuro Oncol. 12, 580-594.

We claim:

1. A method comprising:
   (a) identifying a population of cancer stem cells expressing HER2 and one or more of CD44, CD24, ESA, CD20, CD105, CD90, CD326 (EpCAM), CD34, CD133, CD117, Sca-1, HES6, ALDH1, CD166, CEACAM6, CD59, and CD49f in a subject that suffers from a Stage 1 non-HER2 amplified cancer; and
   (b) treating the subject having the identified population of cancer stem cells with a HER2 targeting agent.
2. The method of claim 1, further comprising, prior to said treating, receiving information that said subject, or a sample from said subject, has been identified as having: 1) said non-HER2-amplified cancer, and 2) said cancer stem cells that express HER2 and/or a HER2 indicator marker.
3. The method of claim 2, wherein said HER2 indicator marker comprises ALDH1.
4. The method of claim 1, wherein subject is treated with said HER2 targeting agent as adjuvant therapy.
5. The method of claim 1, wherein said subject has had any discernable tumors removed by surgery prior to said treating.
6. The method of claim 1, wherein said non-HER2-amplified cancer comprises non-HER2-amplified breast cancer.
7. The method of claim 1, wherein said cancer stem cells are breast cancer stem cells or gastric cancer stem cells.
8. The method of claim 1, further comprising testing a cancer sample from said subject and detecting expression of HER2 and/or a HER2 indicator marker by cancer stem cells in said sample.
9. The method of claim 8, further comprising isolating said cancer stem cells from said non-HER2-amplified cancer sample prior to said detecting.
10. The method of claim 1, further comprising testing a cancer sample from said subject and determining that said cancer sample is a non-HER2-amplified cancer sample.
11. The method of claim 1, wherein said HER2 targeting agent comprises an anti-HER2 antibody.
12. The method of claim 11, wherein said anti-HER2 antibody comprises Trastuzumab.
13. A method comprising:
   (a) identifying a population of cancer stem cells expressing HER2 and one or more of CD44, CD24, ESA, CD20, CD105, CD90, CD326 (EpCAM), CD34, CD133, CD117, Sca-1, HES6, ALDH1, CD166, CEACAM6, CD59, and CD49f in a subject that suffers from a Stage 1 non-HER2 amplified gastric cancer; and
   (b) treating the subject having the identified population of cancer stem cells with a HER2 targeting agent.
14. A method comprising:
   (a) identifying a population of cancer stem cells expressing HER2 and one or more of CD44, CD24, ESA, CD20, CD105, CD90, CD326 (EpCAM), CD34, CD133, CD117, Sca-1, HES6, ALDH1, CD166, CEACAM6, CD59, and CD49f in a subject that suffers from a Stage 1 non-HER2 amplified cancer; and
   (b) treating the subject having the identified population of cancer stem cells with a HER2 targeting agent and an additional agent to prevent resistance to said HER2.
15. The method of claim 14, wherein said additional agent blocks and/or deactivates an IL6 inflammatory loop that expands cancer stem cell populations.
16. The method of claim 15, wherein said additional agent comprises an anti-IL6R antibody.
17. A method of treating and/or preventing resistance of cancer cells or cancer stem cells to a HER2 targeting agent comprising co-administering to a subject suffering from cancer a IL6R targeting agent and said HER2 targeting agent.

* * * * *